(12) United States Patent
Walters et al.

(10) Patent No.: US 10,485,524 B2
(45) Date of Patent: *Nov. 26, 2019

(54) INSTRUMENT AND METHODS FOR SURGICALLY CLOSING PERCUTANEOUS PUNCTURES

(75) Inventors: Greg Walters, Exton, PA (US); Gary Roubin, New York, NY (US); Michael Nispel, Malvern, PA (US); Mike Dotsey, Chester Springs, PA (US); Piyush Arora, Philadelphia, PA (US)

(73) Assignee: Essential Medical, Inc., Exton, PA (US)

( * ) Notice: Subject to any disclaimer, the term of this patent is extended or adjusted under 35 U.S.C. 154(b) by 1425 days.

This patent is subject to a terminal disclaimer.

(21) Appl. No.: 13/605,720

(22) Filed: Sep. 6, 2012

(65) Prior Publication Data

US 2013/0178895 A1 Jul. 11, 2013

Related U.S. Application Data

(60) Provisional application No. 61/551,251, filed on Oct. 25, 2011, provisional application No. 61/621,409, filed on Apr. 6, 2012.

(51) Int. Cl.
*A61B 17/00* (2006.01)
*A61B 17/04* (2006.01)
*A61B 17/22* (2006.01)

(52) U.S. Cl.
CPC ...... *A61B 17/0057* (2013.01); *A61B 17/0401* (2013.01); *A61B 2017/00592* (2013.01);
(Continued)

(58) Field of Classification Search
CPC ............ A61B 17/0057; A61B 17/0401; A61B 2017/0409; A61B 2017/0459;
(Continued)

(56) References Cited

U.S. PATENT DOCUMENTS

| | | |
|---|---|---|
| 3,125,095 A | 3/1964 | Kaufman et al. |
| 4,665,918 A | 5/1987 | Garza et al. |

(Continued)

FOREIGN PATENT DOCUMENTS

| | | |
|---|---|---|
| EP | 0474752 B1 | 6/1995 |
| EP | 0766947 A2 | 4/1997 |

(Continued)

OTHER PUBLICATIONS

International Search Report and Written Opinion for International Application No. PCT/US2012/061855 dated Jan. 22, 2013 (21 pages).

*Primary Examiner* — Sarah W Aleman
*Assistant Examiner* — Rachel S Highland
(74) *Attorney, Agent, or Firm* — Offit Kurman, P.C.; Gregory A. Grissett

(57) ABSTRACT

A closure device for sealing a percutaneous puncture in a wall of a body passageway, the closure device including at least one of a toggle configured to engage an interior surface of the body passageway or a plug configured to engage an exterior surface of the body passageway and a guide wire configured to extend from an outside of the body to inside the body passageway, wherein at least one of the toggle and the plug is associated with the guide wire.

27 Claims, 44 Drawing Sheets

(52) U.S. Cl.
CPC ............ *A61B 2017/00606* (2013.01); *A61B 2017/00615* (2013.01); *A61B 2017/00619* (2013.01); *A61B 2017/00623* (2013.01); *A61B 2017/00628* (2013.01); *A61B 2017/00659* (2013.01); *A61B 2017/00663* (2013.01); *A61B 2017/0406* (2013.01); *A61B 2017/0409* (2013.01); *A61B 2017/0414* (2013.01); *A61B 2017/0419* (2013.01); *A61B 2017/0448* (2013.01); *A61B 2017/0459* (2013.01); *A61B 2017/22054* (2013.01); *A61B 2017/22069* (2013.01)

(58) Field of Classification Search
CPC .... A61B 2017/0448; A61B 2017/0419; A61B 2017/0406; A61B 2017/0414; A61B 2017/00615; A61B 2017/00628; A61B 2017/00659; A61B 2017/00623; A61B 2017/00663; A61B 2017/22069; A61B 2017/00592; A61B 2017/00619; A61B 2017/22054; A61B 2017/00606
See application file for complete search history.

(56) References Cited

U.S. PATENT DOCUMENTS

| | | |
|---|---|---|
| 4,760,847 A | 8/1988 | Vaillancourt |
| 4,990,151 A | 2/1991 | Wallstén |
| 5,021,059 A | 6/1991 | Kensey et al. |
| 5,026,377 A | 6/1991 | Burton et al. |
| 5,222,974 A | 6/1993 | Kensey et al. |
| 5,282,827 A | 2/1994 | Kensey et al. |
| 5,292,309 A | 3/1994 | Van Tassel et al. |
| 5,306,254 A | 4/1994 | Nash et al. |
| 5,324,306 A | 6/1994 | Makower et al. |
| 5,411,520 A | 5/1995 | Nash et al. |
| 5,531,759 A | 7/1996 | Kensey et al. |
| 5,545,178 A | 8/1996 | Kensey et al. |
| 5,643,318 A | 7/1997 | Tsukernik et al. |
| 5,662,681 A | 9/1997 | Nash et al. |
| 5,700,277 A | 12/1997 | Nash et al. |
| 6,090,130 A | 7/2000 | Nash et al. |
| 6,425,911 B1 | 7/2002 | Akerfeldt et al. |
| 6,494,848 B1 | 12/2002 | Sommercorn et al. |
| 6,682,489 B2 | 1/2004 | Tenerz et al. |
| 7,044,916 B2 | 5/2006 | Tenerz et al. |
| 7,073,509 B2 | 7/2006 | Tenerz et al. |
| 7,285,097 B2 | 10/2007 | Tenerz et al. |
| 7,618,436 B2 | 11/2009 | Forsberg |
| 7,648,493 B2 | 1/2010 | Forsberg et al. |
| 7,850,654 B2 | 12/2010 | Belhe et al. |
| 7,905,902 B2 | 3/2011 | Huitema et al. |
| 8,273,094 B2 | 9/2012 | Belhe et al. |
| 8,337,522 B2 | 12/2012 | Ditter |
| 8,382,793 B2 | 2/2013 | Egnelöv et al. |
| 8,540,750 B2 | 9/2013 | Tegels |
| 8,974,476 B2 | 3/2015 | Tegels |
| 2001/0044639 A1 | 11/2001 | Levinson |
| 2003/0078616 A1 | 4/2003 | Ginn et al. |
| 2005/0107820 A1 | 5/2005 | Forsberg et al. |
| 2005/0125030 A1 | 6/2005 | Forsberg et al. |
| 2005/0277961 A1* | 12/2005 | Stone ................ A61B 17/0401 606/151 |
| 2006/0058844 A1 | 3/2006 | White et al. |
| 2007/0123936 A1 | 5/2007 | Goldin et al. |
| 2008/0306509 A1 | 12/2008 | Osborne |
| 2010/0016887 A1* | 1/2010 | Inderbitzi .................... 606/213 |
| 2010/0179589 A1 | 7/2010 | Roorda et al. |
| 2011/0054456 A1 | 3/2011 | Thompson et al. |
| 2011/0301619 A1 | 12/2011 | Walters |
| 2012/0010634 A1 | 1/2012 | Crabb et al. |
| 2012/0022585 A1 | 1/2012 | Atanasoska et al. |
| 2012/0065668 A1 | 3/2012 | Ginn et al. |
| 2012/0071919 A1 | 3/2012 | Pipenhagen et al. |
| 2012/0083829 A1 | 4/2012 | Ginn et al. |
| 2012/0109192 A1 | 5/2012 | Egnelov et al. |
| 2012/0116446 A1 | 5/2012 | Green et al. |
| 2012/0143245 A1 | 6/2012 | Tegels |
| 2012/0158044 A1 | 6/2012 | Jenson et al. |
| 2012/0245517 A1 | 9/2012 | Tegels |
| 2012/0245597 A1 | 9/2012 | Tegels |
| 2012/0245624 A1 | 9/2012 | Glazier et al. |
| 2012/0283770 A1 | 11/2012 | Kramer et al. |
| 2012/0296275 A1 | 11/2012 | Martin et al. |
| 2013/0006298 A1 | 1/2013 | Terwey |
| 2013/0035719 A1 | 2/2013 | Hill et al. |
| 2013/0072949 A1 | 3/2013 | Halac et al. |
| 2013/0079802 A1 | 3/2013 | Halac et al. |
| 2013/0103077 A1 | 4/2013 | Ditter |
| 2013/0144316 A1 | 6/2013 | McCrea et al. |
| 2013/0150884 A1 | 6/2013 | Belhe et al. |
| 2014/0046217 A1 | 2/2014 | Lim |
| 2014/0046220 A1 | 2/2014 | Nelson |
| 2014/0094846 A1 | 4/2014 | Lim |
| 2014/0188160 A1 | 7/2014 | Tegels |
| 2015/0068009 A1 | 3/2015 | Walters |

FOREIGN PATENT DOCUMENTS

| | | |
|---|---|---|
| EP | 0797953 A2 | 10/1997 |
| EP | 1169968 A1 | 1/2002 |
| EP | 1222896 A2 | 7/2002 |
| EP | 1254634 A1 | 11/2002 |
| EP | 0664687 B2 | 8/2003 |
| EP | 1371333 A1 | 12/2003 |
| EP | 1413255 A1 | 4/2004 |
| EP | 1440661 A1 | 7/2004 |
| EP | 1532929 A1 | 5/2005 |
| EP | 1658811 A1 | 5/2006 |
| EP | 1695667 A1 | 8/2006 |
| EP | 1836967 A1 | 9/2007 |
| EP | 1836968 A1 | 9/2007 |
| EP | 2055236 A1 | 5/2009 |
| EP | 2064999 A2 | 6/2009 |
| EP | 2213247 A1 | 8/2010 |
| EP | 2215974 A2 | 8/2010 |
| EP | 1919367 B1 | 10/2011 |
| EP | 1874195 B1 | 1/2012 |
| EP | 1893100 B1 | 3/2012 |
| EP | 2227148 B1 | 4/2012 |
| EP | 1893099 B1 | 6/2012 |
| EP | 1893098 B1 | 1/2014 |
| EP | 2611366 B1 | 7/2014 |
| EP | 2605707 B1 | 10/2014 |
| WO | WO8911301 A1 | 11/1989 |
| WO | WO9014796 A1 | 12/1990 |
| WO | WO9308743 A1 | 5/1993 |
| WO | WO9308746 A2 | 5/1993 |
| WO | WO 94/07421 | 4/1994 |
| WO | WO9805259 A1 | 2/1998 |
| WO | WO9922646 A1 | 5/1999 |
| WO | WO2000078226 | 12/2000 |
| WO | WO2003094740 A1 | 11/2003 |
| WO | WO2004096056 A2 | 11/2004 |
| WO | WO2005002451 A1 | 1/2005 |
| WO | WO2005039387 A2 | 5/2005 |
| WO | WO2005060514 A2 | 7/2005 |
| WO | WO2006075228 A1 | 7/2006 |
| WO | WO2006110615 A2 | 10/2006 |
| WO | WO2007035187 A2 | 3/2007 |
| WO | WO2008036634 A1 | 3/2008 |
| WO | WO2009005722 A1 | 1/2009 |
| WO | WO2009025836 A1 | 2/2009 |
| WO | WO2009035921 A2 | 3/2009 |
| WO | WO2009088440 A1 | 7/2009 |
| WO | WO2009088441 A1 | 7/2009 |
| WO | WO2009112930 A2 | 9/2009 |
| WO | WO2010129042 A1 | 11/2010 |
| WO | WO2011014244 A1 | 2/2011 |
| WO | WO2011019374 WO | 2/2011 |
| WO | WO2011025529 A1 | 3/2011 |
| WO | WO2011025543 A2 | 3/2011 |
| WO | WO2011037635 A1 | 3/2011 |

(56) References Cited

FOREIGN PATENT DOCUMENTS

| | | |
|---|---|---|
| WO | WO2011146729 A2 | 11/2011 |
| WO | WO2011156498 A1 | 12/2011 |
| WO | WO2012009007 A1 | 1/2012 |
| WO | WO2012012641 A1 | 1/2012 |
| WO | WO2012045356 A1 | 4/2012 |
| WO | WO2012061486 A2 | 5/2012 |
| WO | WO2012064888 A2 | 5/2012 |
| WO | WO2012083045 A1 | 6/2012 |
| WO | WO2012145356 A1 | 10/2012 |
| WO | WO2012145362 A1 | 10/2012 |
| WO | WO2012148745 A1 | 11/2012 |
| WO | WO2012148747 A1 | 11/2012 |
| WO | WO2012158662 A1 | 11/2012 |
| WO | WO2012158737 A1 | 11/2012 |
| WO | WO2012158738 A1 | 11/2012 |
| WO | WO2012158740 A1 | 11/2012 |
| WO | WO2012158931 A1 | 11/2012 |
| WO | WO 2013/063227 A1 | 5/2013 |
| WO | WO2013081659 A1 | 6/2013 |

\* cited by examiner

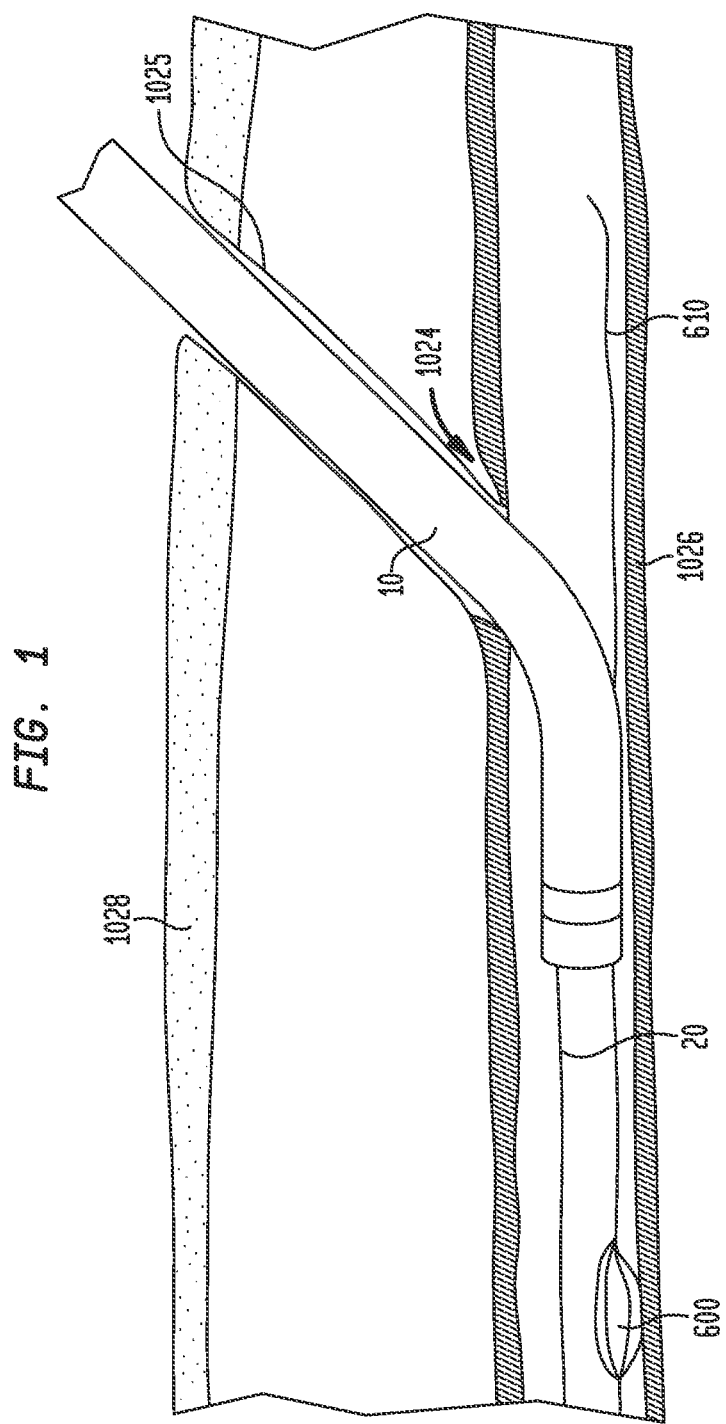

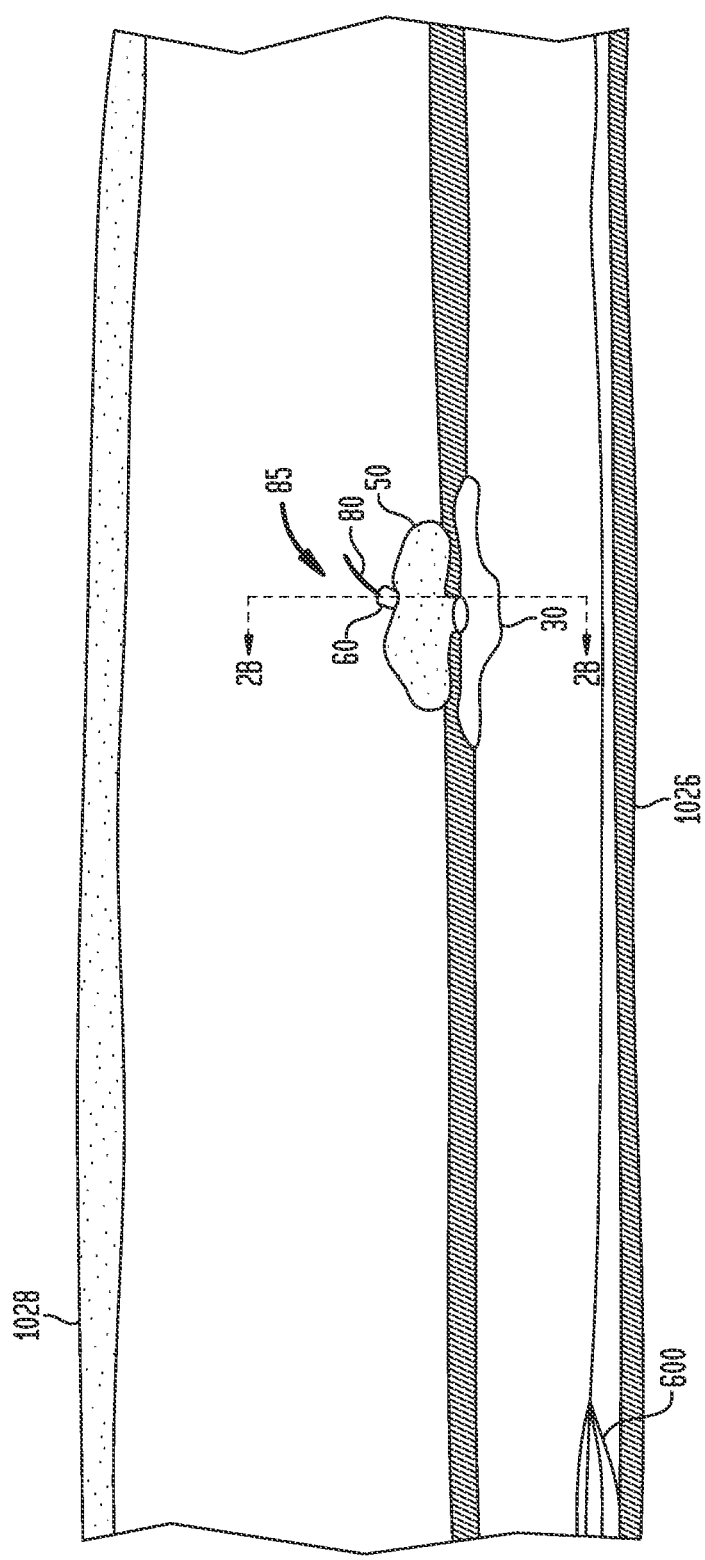

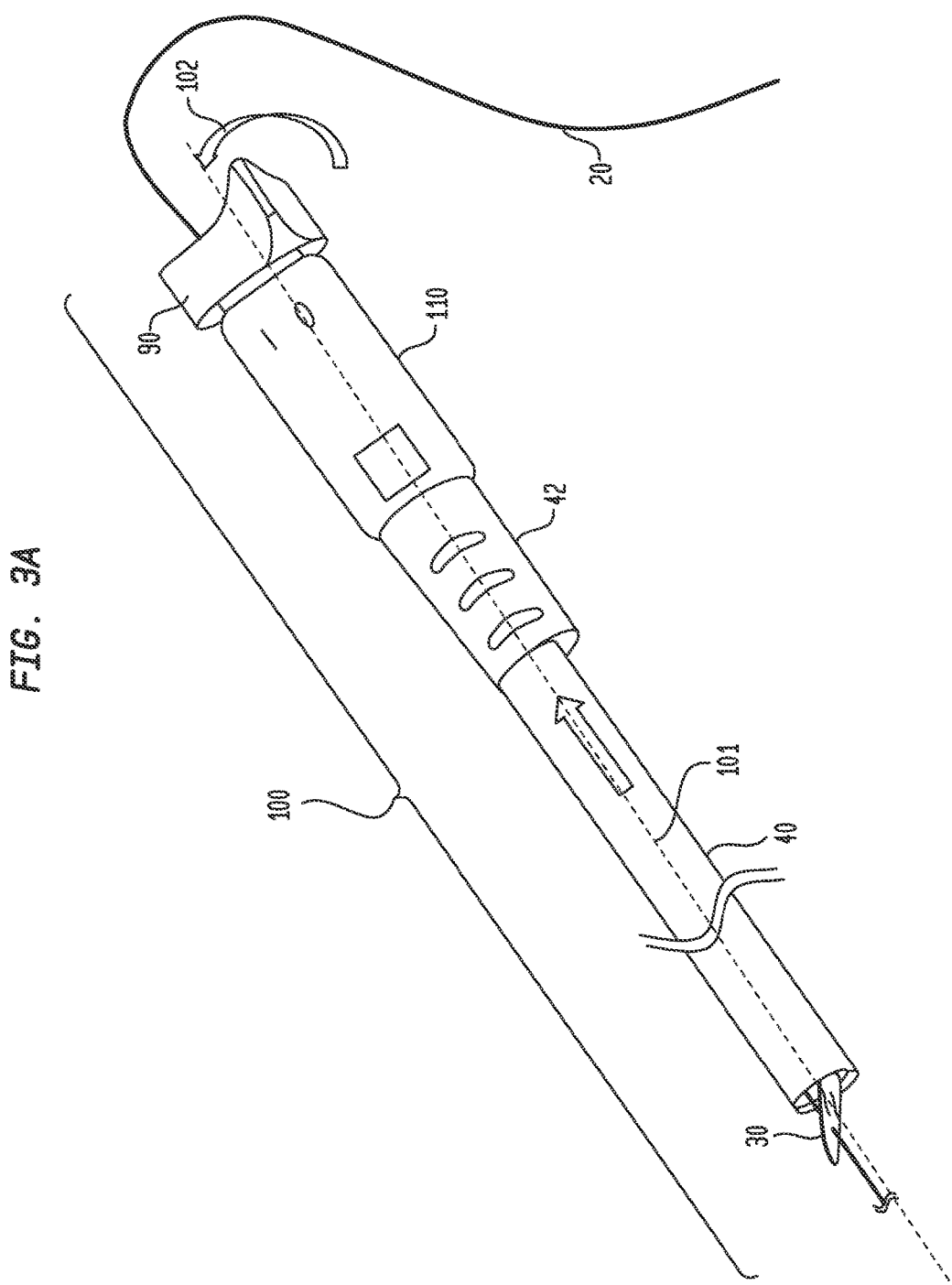

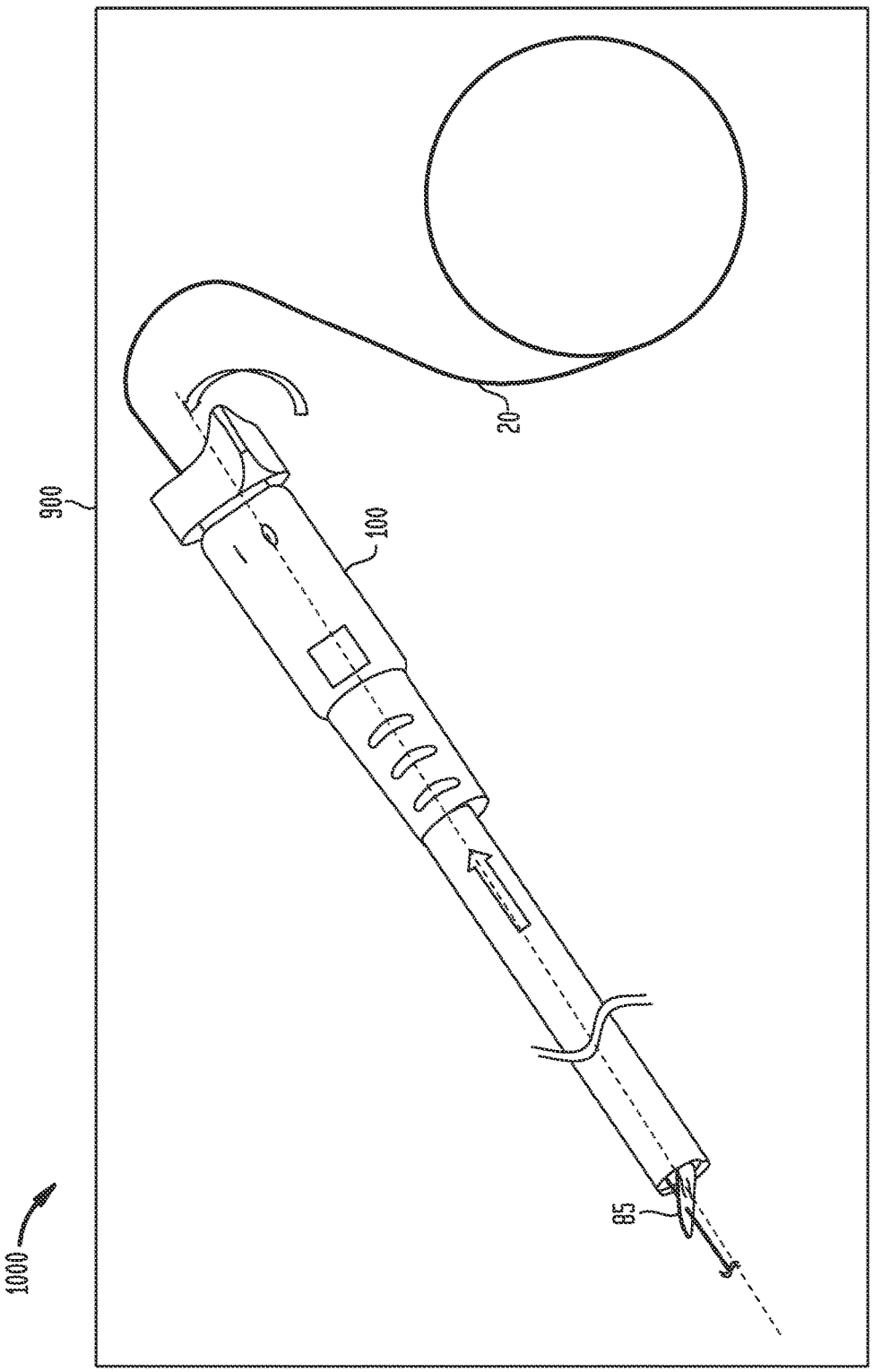

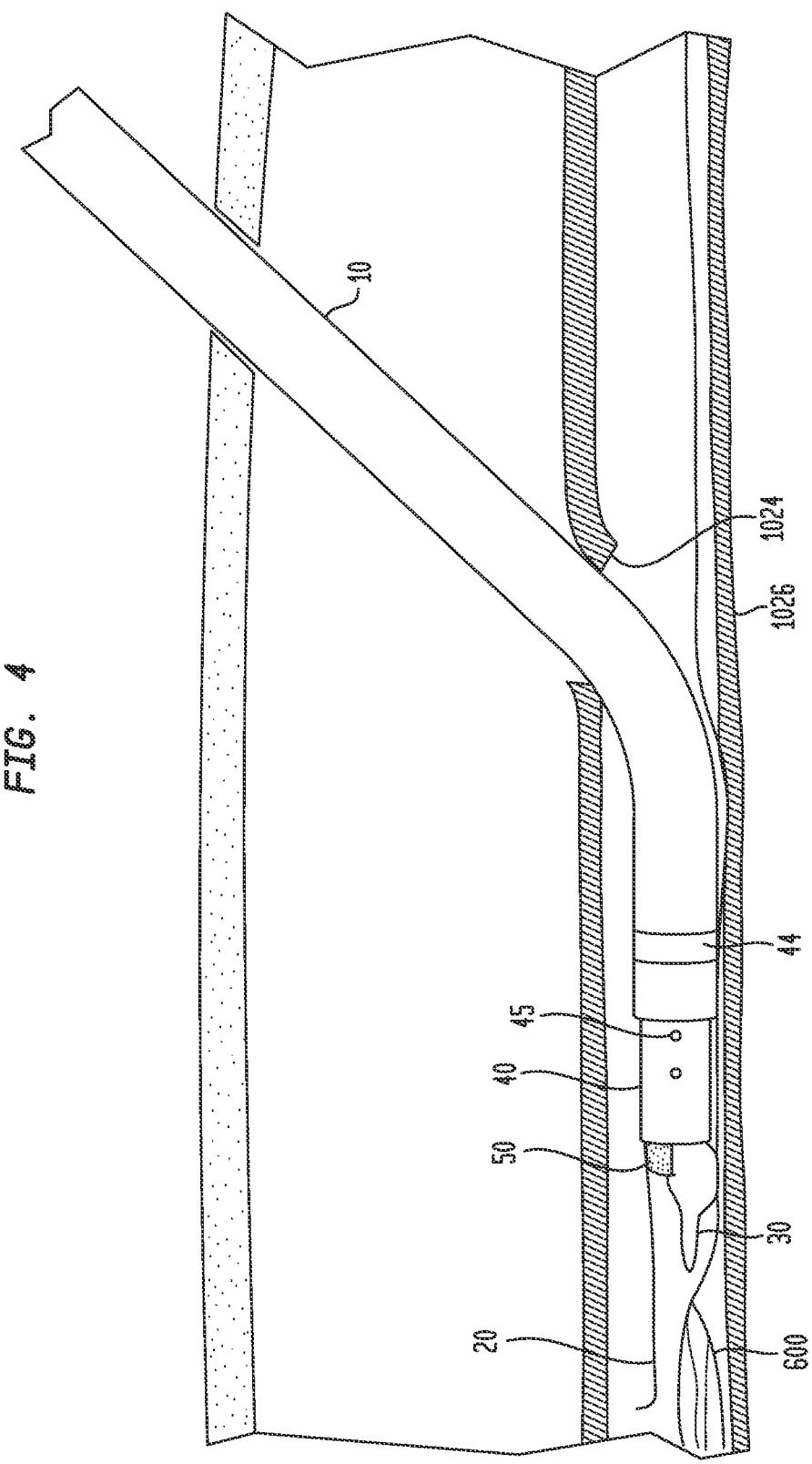

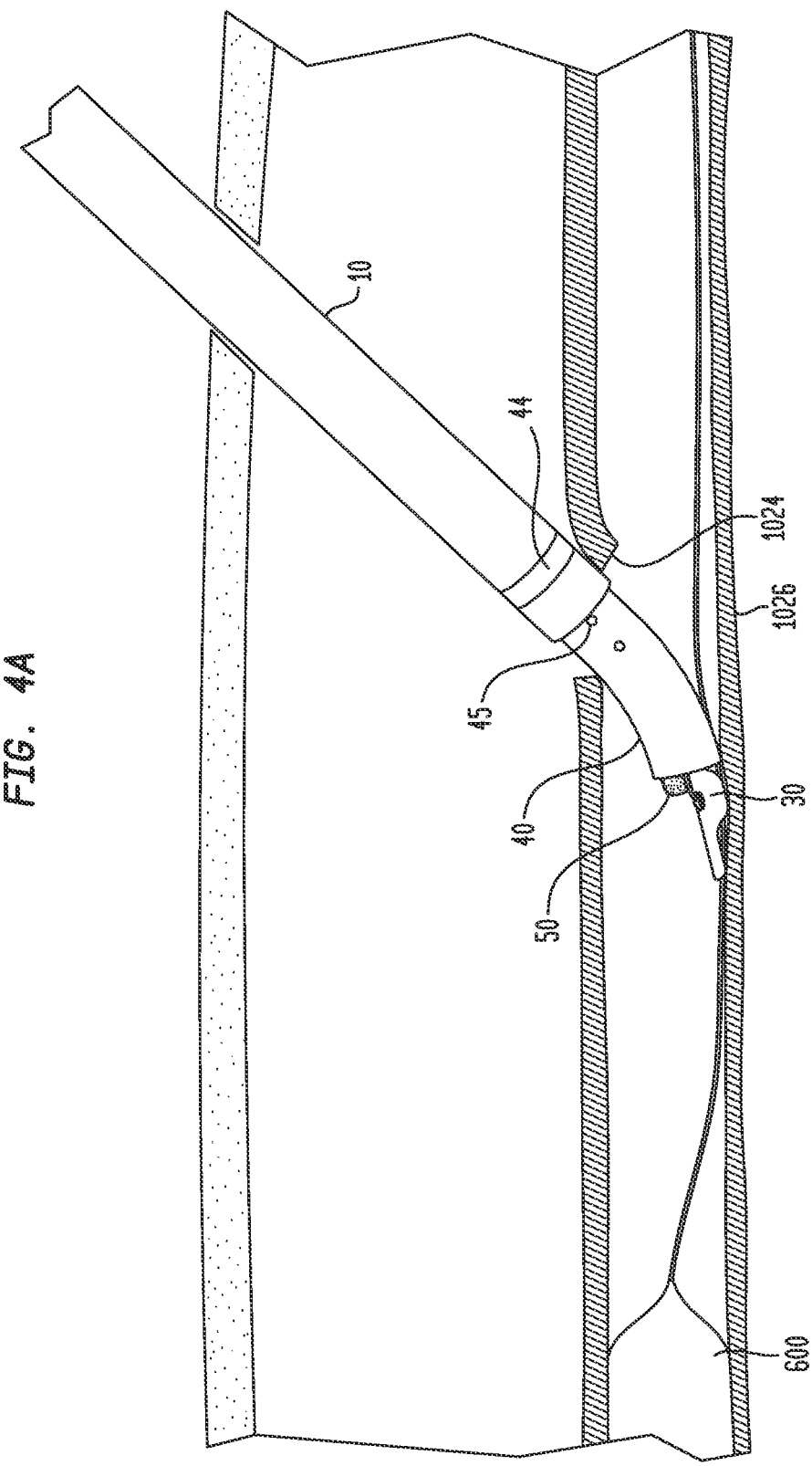

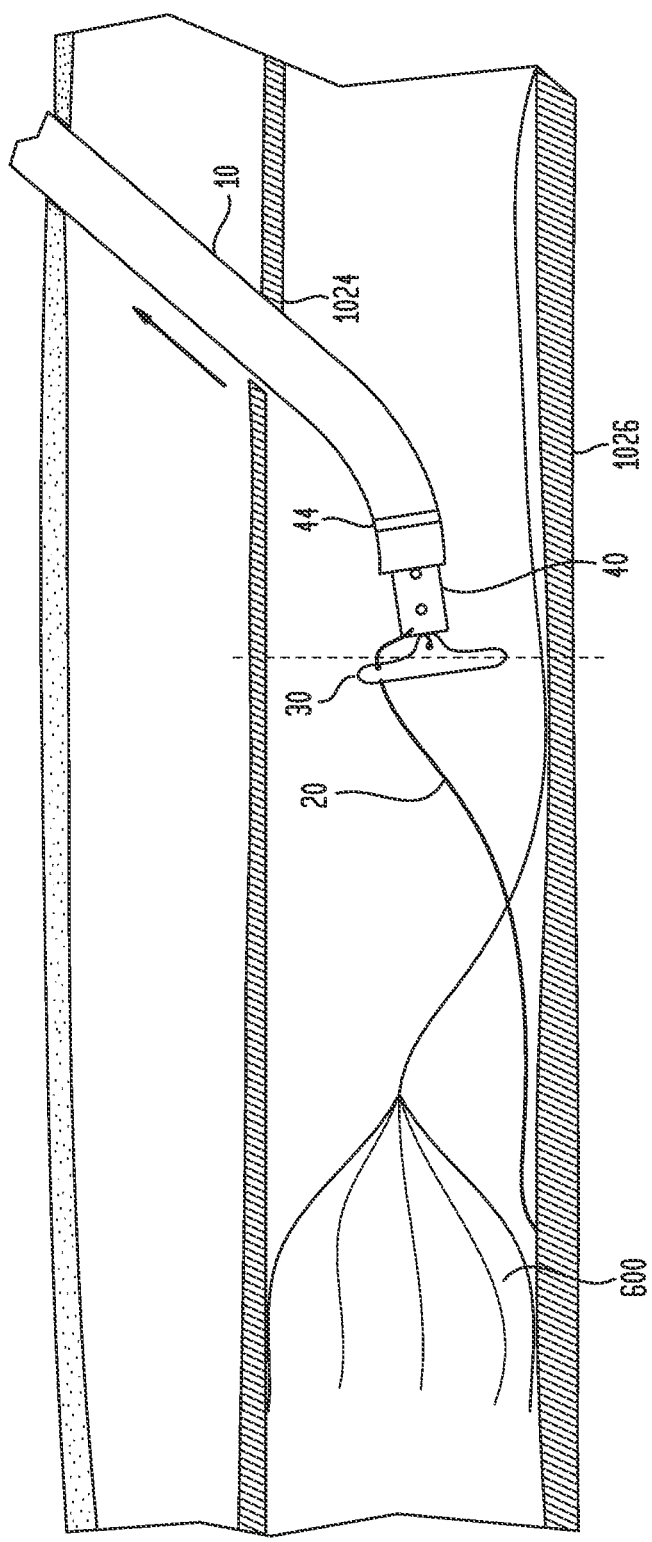

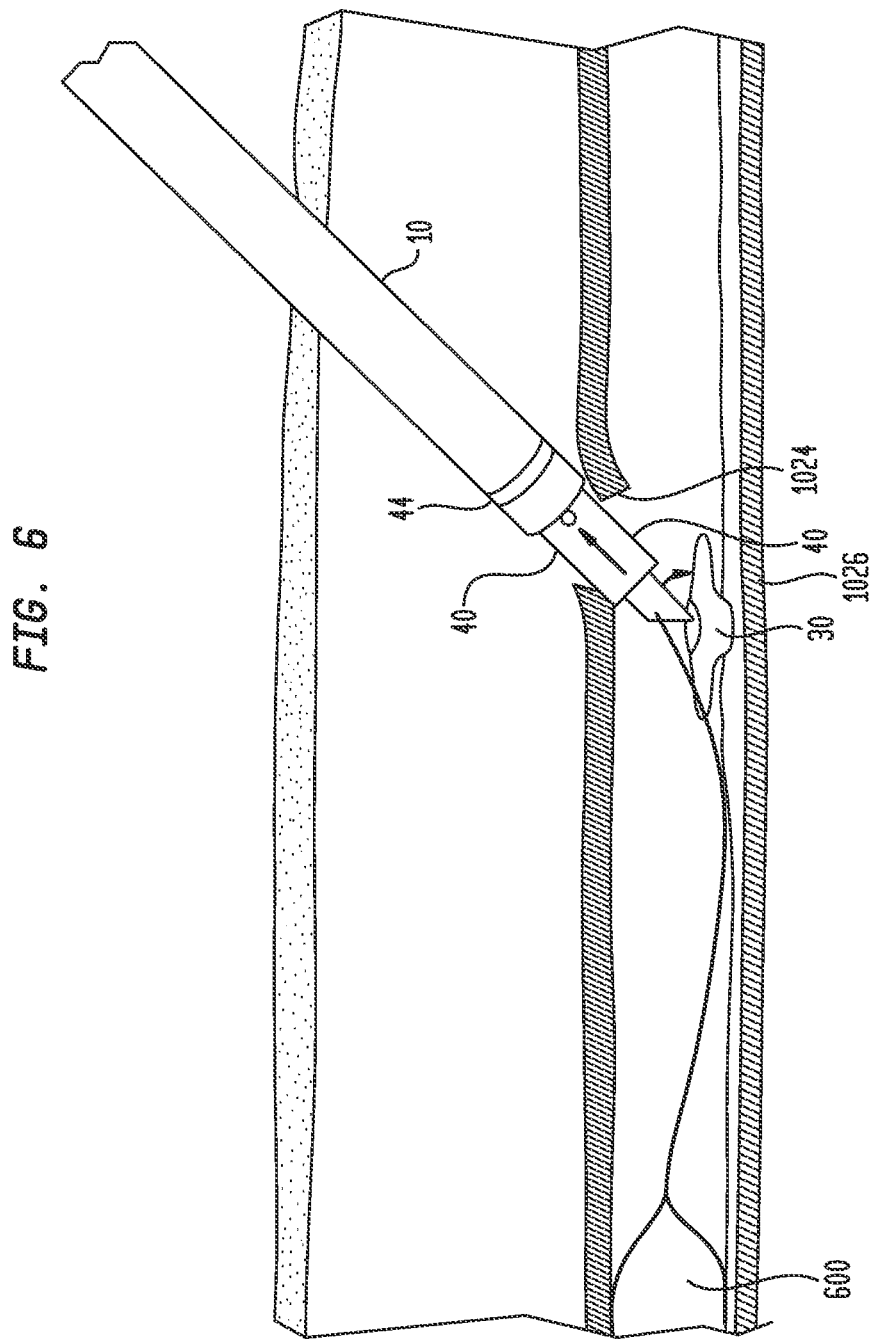

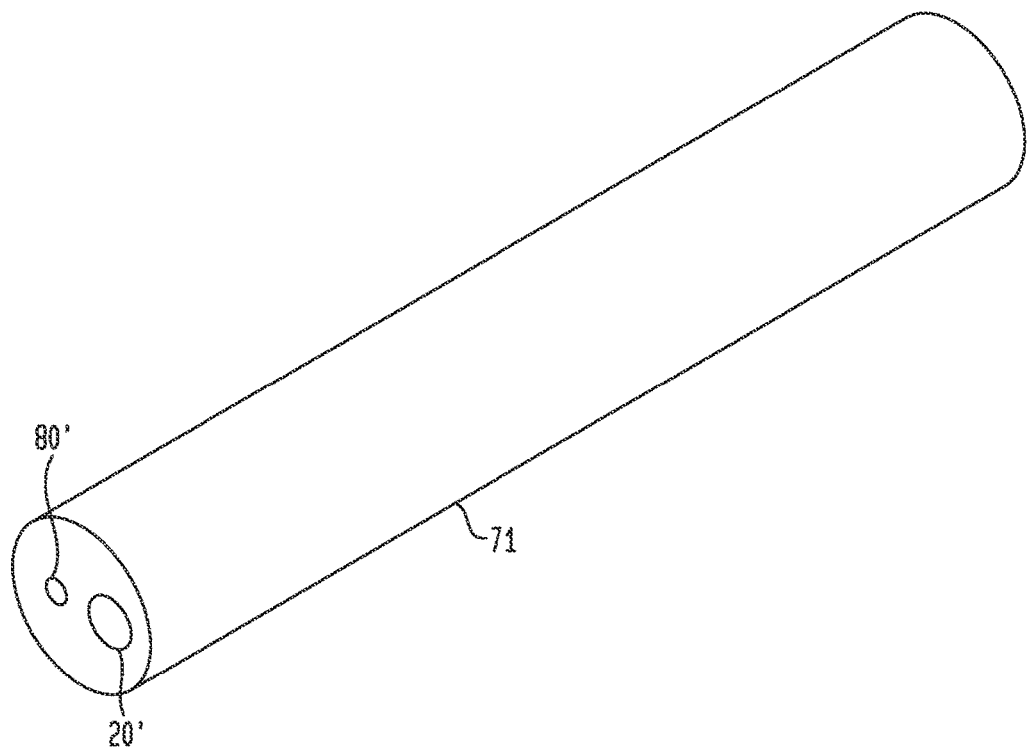

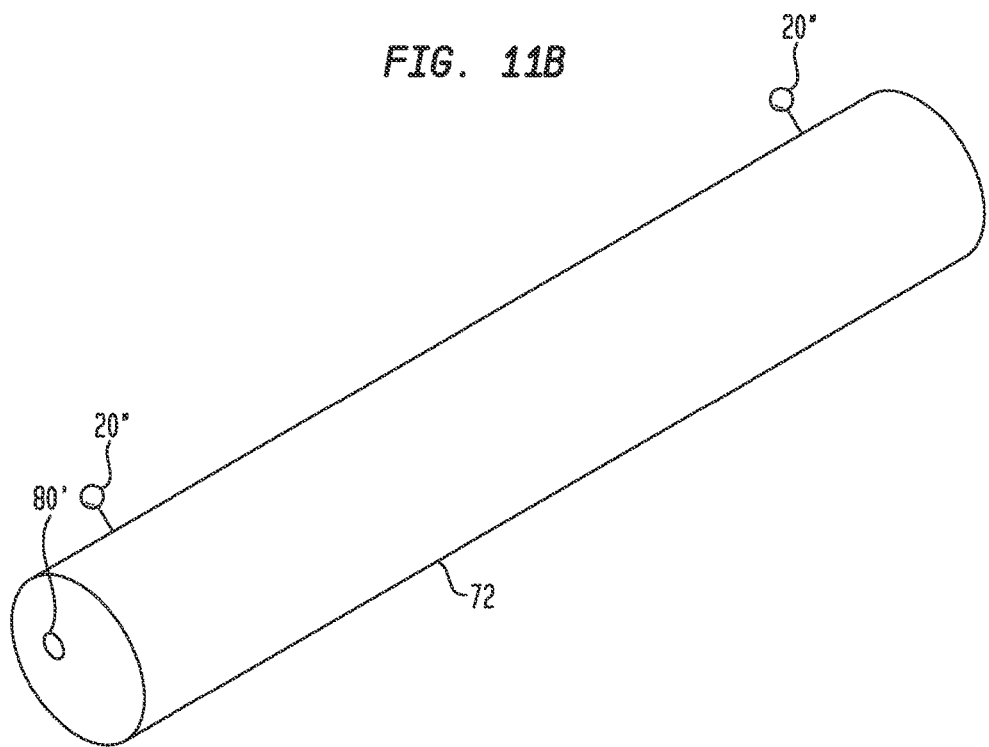

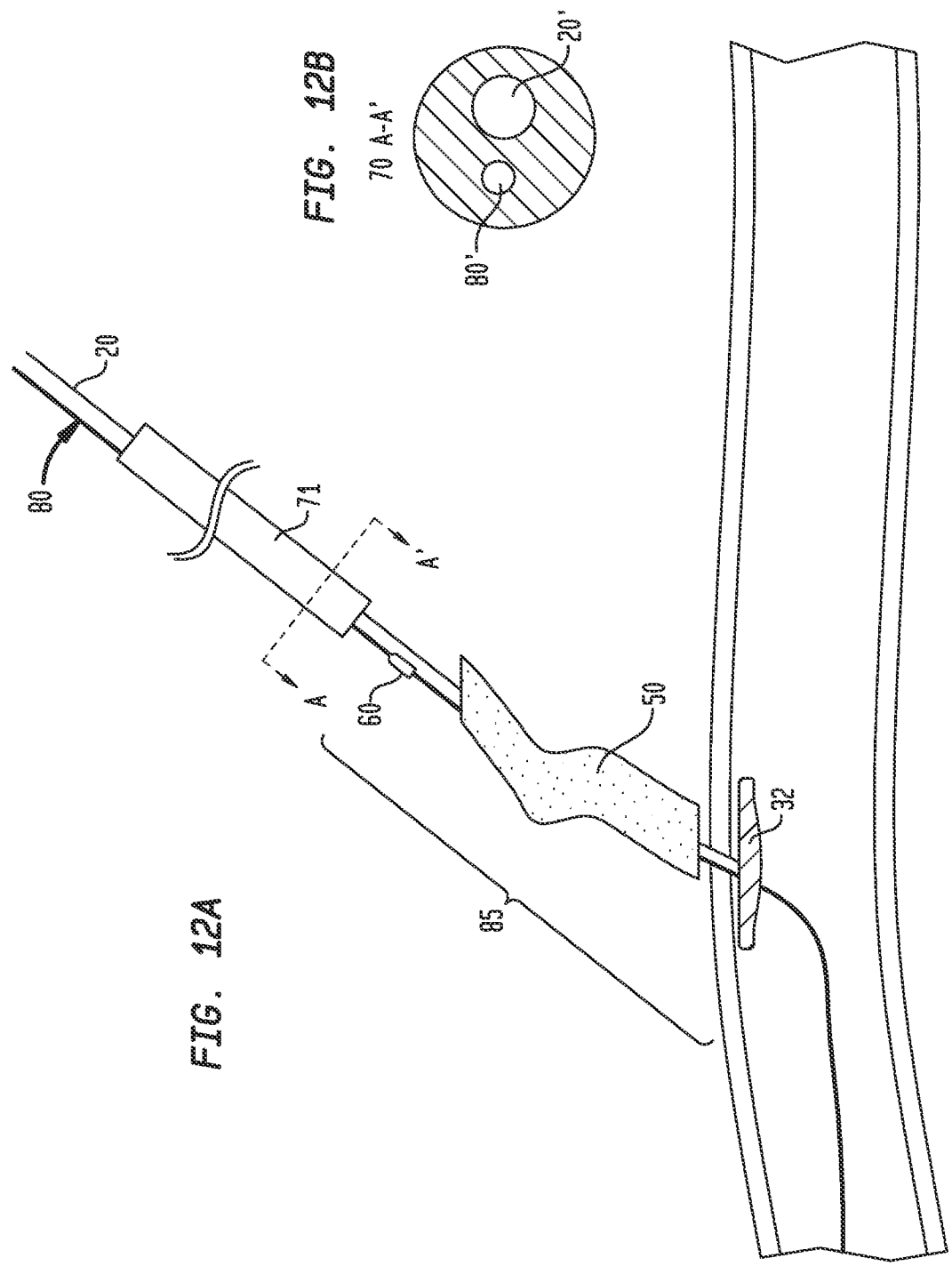

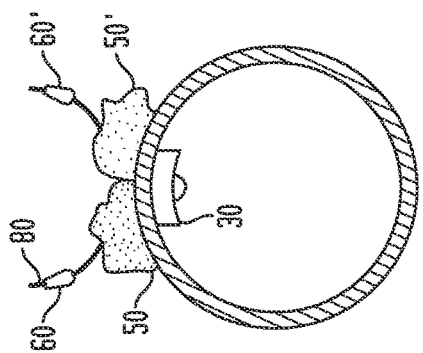
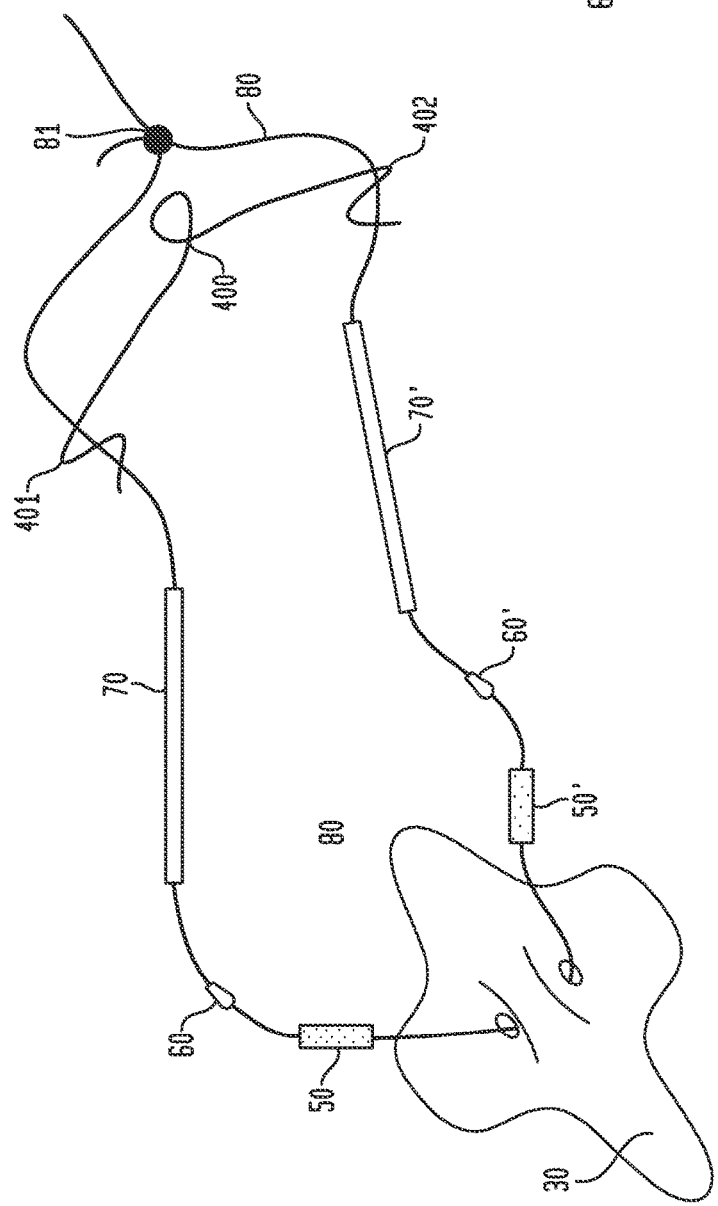

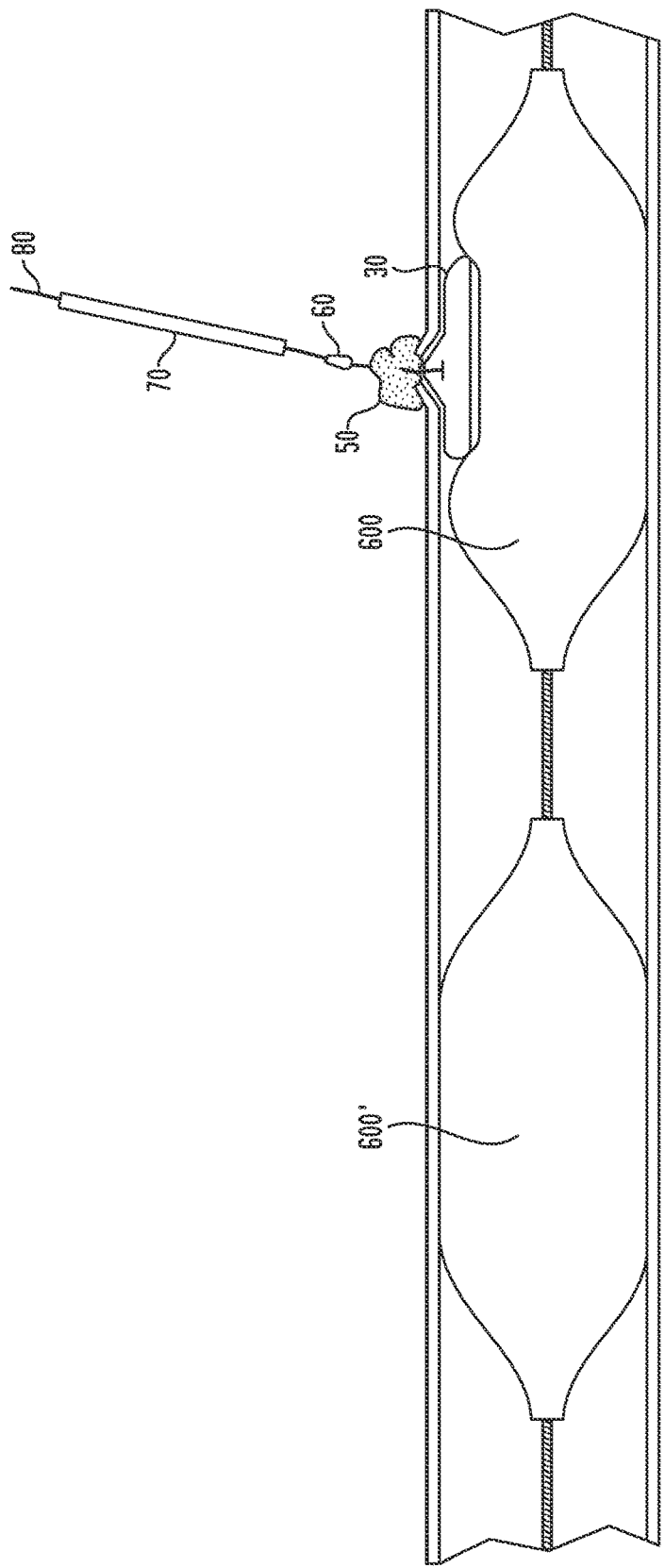

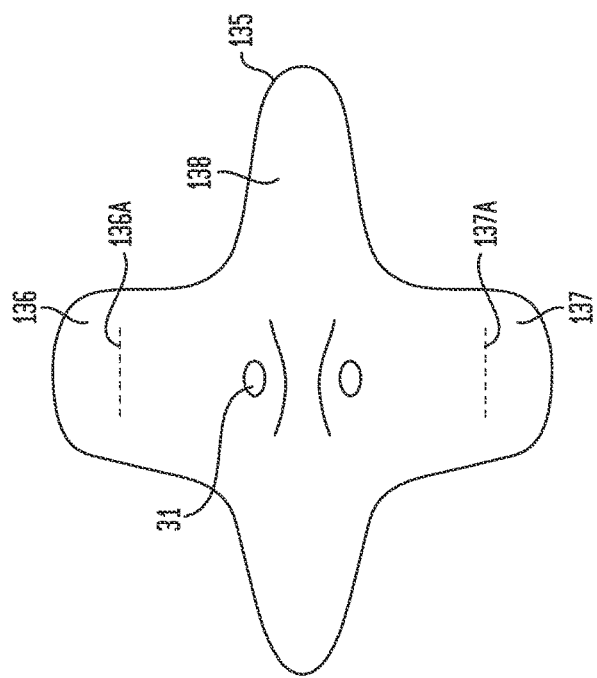
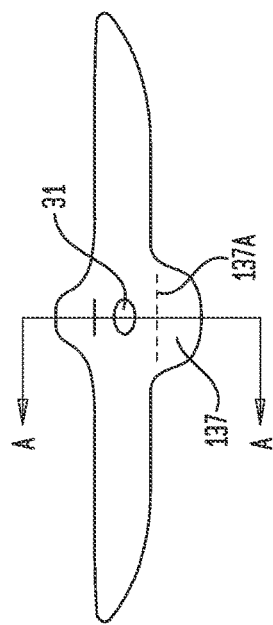
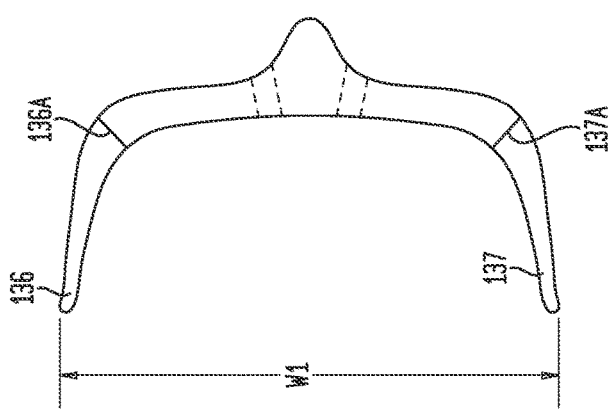

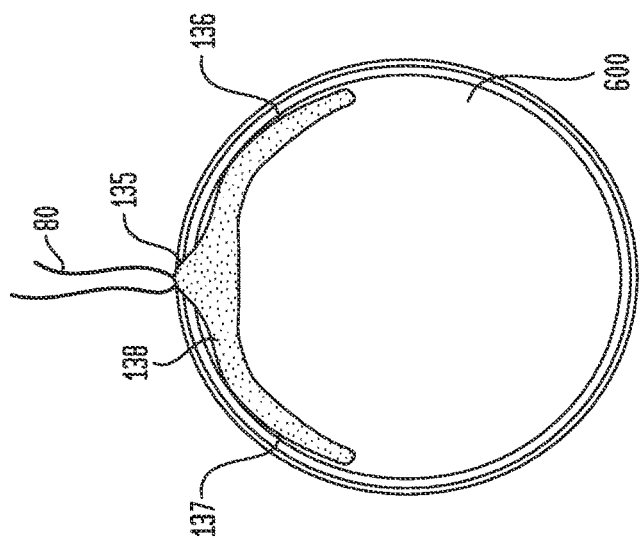
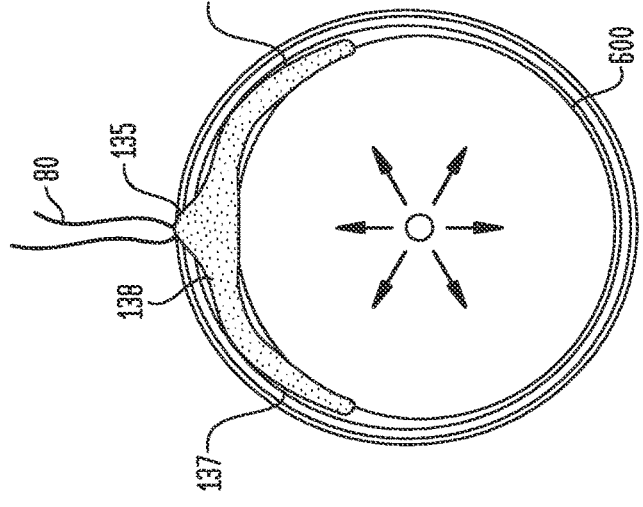
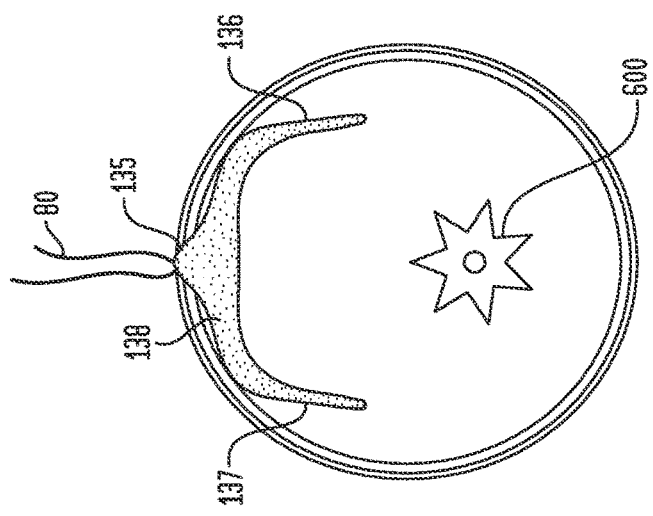

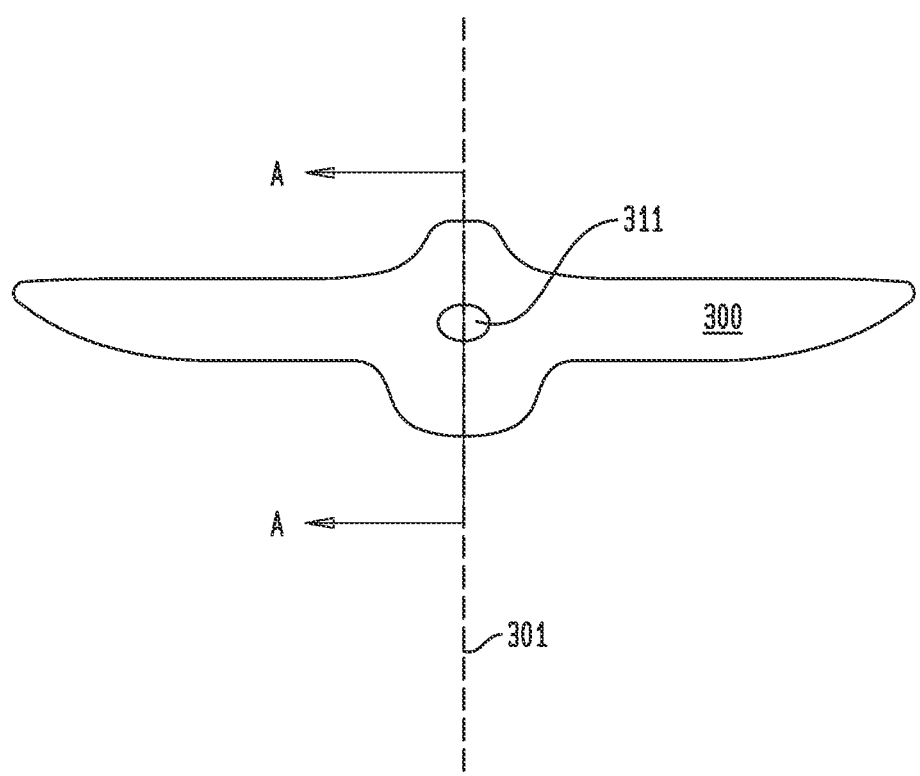

INSTRUMENT AND METHODS FOR SURGICALLY CLOSING PERCUTANEOUS PUNCTURES

CROSS-REFERENCE TO RELATED APPLICATION(S)

The present application claims priority to U.S. Provisional Patent Application No. 61/551,251, filed on Oct. 25, 2011, entitled "LARGE BORE VASCULAR SEALING DEVICE AND METHOD," and U.S. Provisional Patent Application No. 61/621,409, filed on Apr. 6, 2012, entitled "GUIDE WIRE THROUGH TOGGLE," the contents of these applications being incorporated herein by reference in their entirety.

BACKGROUND

Field of the Invention

The present invention relates generally to closing percutaneous punctures.

Related Art

U.S. Pat. No. 5,282,827 (hereinafter, the '827 patent), entitled Hemostatic Puncture Closure System and Method of Use, discloses systems for sealing a percutaneous incision or puncture in a blood vessel. The systems of the '827 patent comprise a closure device, an introducer, and a deployment instrument including a carrier for the closure device. The closure device has three basic components, namely, a sealing member, an intra-arterial anchor, and a positioning member.

The sealing member is in the form of an elongate, rod-like plug, e.g., a compressed hemostatic, resorbable collagen sponge or foam. This plug member is arranged for sealing the puncture. The anchor is an elongate, stiff, low-profile member which is arranged to be seated inside the artery against the artery wall contiguous with the puncture. The anchor is molded of non-hemostatic resorbable polymer similar to conventional resorbable sutures.

The positioning member comprises a filament, e.g., a resorbable suture. The filament connects the anchor and the collagen plug (sealing member) in a pulley-like arrangement, and includes a portion extending outside the patient's body. The outwardly located filament portion is arranged to be pulled, i.e., tension applied thereto, after the anchor is located within the interior of the artery and in engagement with the inner wall of the artery contiguous with the incision or puncture. The pulling on the filament causes its pulley arrangement to move the plug in the puncture tract toward the anchor. A tamper forming a portion of the deployment instrument is slid down the filament while the filament is maintained in tension to gently tamp the plug in the puncture tract to cause the plug to deform so that its diameter increases. Tension is maintained on the filament by use of an externally located spring during the tamping procedure.

The expansion of the plug within the tract is enhanced by the fact that it is formed of a compressed collagen so that it expands in the presence of blood within the puncture tract. The expansion of the plug within the puncture tract serves to hold it in place. Moreover, the closure device quickly becomes locked in place through the clotting of the hemostatic collagen plug within the puncture tract. The spring serves to hold the plug in its deformed state until such time that the plug is locked in place by the hemostatic clotting action. Once this has occurred, so that the plug is effectively locked within the puncture tract, the externally located spring can be removed. This typically occurs after approximately 30 minutes. After the spring is removed, the filament is severed at the top of the tamper. The tamper is then removed and the remaining portion of the filament is cut subcutaneously prior to the discharge of the patient. The portion of the filament connecting the anchor to the plug remains in tension, thereby holding the closure device permanently in place until it is eventually absorbed by the patient's body.

U.S. Pat. No. 5,662,681 (hereinafter, the '681 patent), entitled Self-locking Closure for Sealing Percutaneous Punctures, also teaches systems for sealing a percutaneous incision or puncture in a blood vessel.

SUMMARY

According to one aspect there is a closure device for sealing a percutaneous puncture in a wall of a body passageway, the closure device comprising at least one of an anchor configured to engage an interior surface of the body passageway or a plug configured to engage an exterior surface of the body passageway and a guide wire configured to extend from an outside of the body to inside the body passageway, wherein at least one of the anchor and the plug is associated with the guide wire.

According to another aspect, there is a deployment instrument for deploying a closure device for sealing a percutaneous puncture in a wall of a body passageway, the deployment instrument comprising the closure device a carrier device, wherein the carrier device is configured to hold the closure device in a pre-deployment state and a guide wire, the guide wire passing through at least a portion of the closure device.

According to another aspect, there is a deployment instrument for deploying a closure device for sealing a percutaneous puncture in a wall of an artery, the deployment instrument comprising the closure device, wherein the closure device includes a toggle and a plug connected to the toggle and an actuatable assembly having a portion configured to extend into the artery such that the toggle is located in the artery while, in a first state, effectively maintaining a relative position of the toggle with respect to an actuatable component of the deployment instrument.

BRIEF DESCRIPTION OF THE DRAWINGS

Embodiments of the present invention are described herein with reference to the attached drawing sheets in which:

FIG. 1 is a diagram showing the clinical setting of a large bore sheath and a guide wire;

FIG. 2A is a diagram depicting a closure device;

FIG. 3A is diagram of an exemplary deployment instrument according to an exemplary embodiment;

FIG. 3G depicts an exemplary kit according to an exemplary embodiment;

FIGS. 4 and 4A are diagrams showing how an exemplary closure device is inserted into and removed from the artery;

FIG. 5 is a diagram showing how the sheath and the closure device are positioned in the large arteriotomy;

FIG. 6 a diagram showing how the toggle is released in preparation for deployment;

FIGS. 11A-C depict exemplary tampers;

FIG. 12A-B depict exemplary features of a tamper;

FIGS. 20A-B depict an embodiment utilizing a plurality of plugs;

FIG. 22-23 depict use of an occlusion balloon to hold a toggle against an artery wall;

FIGS. 24A-D depict an alternate embodiment of a toggle;

FIGS. 25A-C depict an end view of use of a balloon to hold a toggle against an artery;

FIGS. 26A-B depict an alternate embodiment of a toggle;

DETAILED DESCRIPTION

Figure 2B:
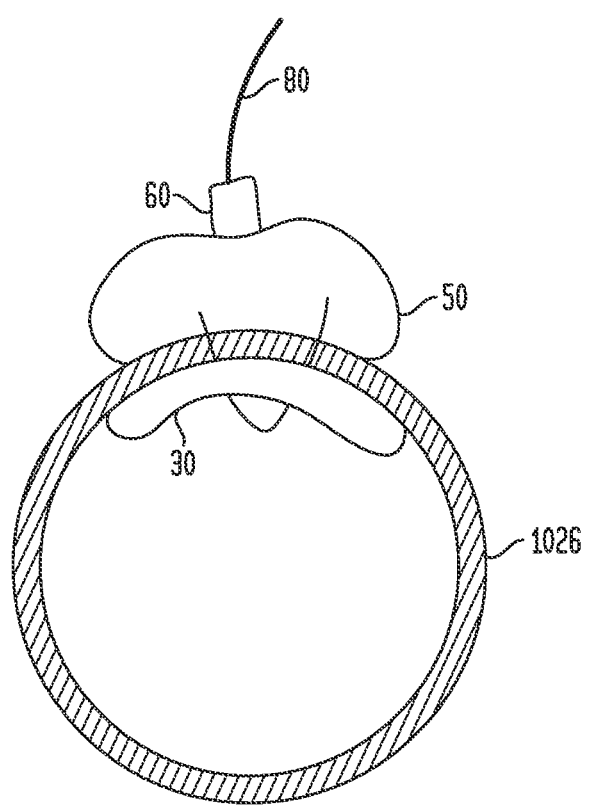
FIG. 2B is a cross-sectional view of the closure device of FIG. 2A.

Some exemplary embodiments are directed towards wound (puncture) closure devices, systems and methods, and wound (puncture) closure device deployment instruments and methods and systems of utilization thereof, associated with closing a relatively large puncture (wound) of an artery, such as by way of example, a femoral artery. Such a large puncture may exist as a result of a balloon aortic valvulopasty (BAV) and/or percutaneous aortic valve replacement (PAVR) procedure and/or a related procedure, which utilize access sheaths from the 18 to 24F size. Hereinafter, these procedures (BAV, PAVR and related procedures) may be referred to as the "referenced vascular treatment procedures."

An exemplary embodiment of the wound closure system detailed below and some variations thereof interface with an intravascular guide wire. Accordingly, some exemplary embodiments of use of thereof will first be detailed, followed by a discussion of some specific features to the wound closure system of some exemplary embodiments.

In an exemplary embodiment, a needle cannula usable in a valvulopasty and/or percutaneous aortic valve replacement procedure is inserted into an artery. Such a needle may correspond to, by way of example and not by way of limitation, a needle usable in the Seldinger method.

While the needle cannula is in place (extending into the artery), a guide wire is passed through the cannula of the needle a desired distance into the artery (sufficient for the teachings detailed herein and/or variations thereof to be practiced, and/or other procedures to be practiced). In an exemplary embodiment, the guide wire is a so-called thirty-five thousandths of an inch guide wire. In an exemplary embodiment, the guide wire is an access guide wire). Once the guide wire is in place, the needle cannula is removed by pulling the needle away from the artery over the guide wire. This leaves the guide wire in place, with a portion thereof extending the desired distance (or thereabouts) into the artery. This further leaves an incision through which the guide wire extends. As will be detailed below, in an exemplary embodiment, the guide wire is part of a wound closure device deployment instrument, although in other exemplary embodiments, the guide wire is a separate element.

An introducer sheath, such as a large bore sheath, is passed over the guidewire, through the incision and into the artery, as depicted in FIG. 1, where element 10 is a large bore sheath, element 20 is a guide wire, element 1026 is a femoral artery (depicted in cross-sectional view), element 1024 is the puncture in the artery (wound in the artery), element 1025 is the tract leading to the puncture 1024 and element 1028 is the skin. By tract it is meant the passageway in the tissue located between the artery 1026 and the skin 1028 of the being, and which is formed when the artery is punctured percutaneously.

It is noted that the scene depicted in FIG. 1 may be achieved through other steps than those just depicted by way of example. Any method or methods that result in the human tissue-medical device interface regime depicted in FIG. 1 and/or variations thereof, which enable the teachings herein and/or variations thereof and/or result in the utility of the teachings detailed herein and/or variations thereof, may be used in some embodiments. Indeed, the aforementioned actions may be part of or be substituted by actions that are part of the referenced vascular treatment procedures. In any event, after executing such actions, a large bore sheath 10 remains in a vessel, such as the common femoral artery, as depicted by FIG. 1 and/or a variation thereof.

As can be understood by the diagram of FIG. 1 and attention to the sizing (unless otherwise noted, the drawings herein are drawn to scale), the sheath 10 is relatively large in relation to the inner diameter of the vessel (e.g., it has an inner diameter and/or an outer diameter of about 0.4, 0.5, 0.6, 0.7 and/or 0.8 or more times the size of the inner diameter of the artery, as measured on a plane lying normal to the longitudinal axes of these tubular structures). In this regard, the sheath 10, as it is a large bore sheath, requires a transverse slit (i.e., a slit extending axially) in the artery which will be relatively large (sufficient to receive the sheath 10 therethrough, after the elastic nature of the artery is taken into account).

In an exemplary embodiment, the guidwire 20 is utilized for advancement of a wound closure device deployment instrument through the sheath 10 in general, and movement of a wound closure device in particular along the guide wire. It is noted that some exemplary details of the deployment instrument and closure device are provided below. However, in some embodiments, the deployment instrument and/or closure device may correspond to the deployment instrument and/or wound closure device of any of the above referenced applications as modified to interface with the large bore sheath 10 and/or closure device and/or deployment instrument detailed below, wherein the closure device may correspond to the closure device of any of the above referenced applications as modified to close such a large opening in the artery (e.g., an opening large enough to permit a sheath of 18F to fit through as depicted in the FIGS.).

Also shown in FIG. 1 is a PTA balloon 600 inserted proximally or from a contralateral puncture site. This balloon is utilized to block blood flow proximal to the large bore puncture site (i.e., the site depicted in FIG. 1), and as an entry for contrast dye. Balloon 600 is depicted in an uninflated or semi-inflated state coupled to guidewire 610. In use, inflation fluid is pumped to the balloon, to inflate the balloon 600. It is noted that some embodiments may not include the balloon 600/may not utilize the balloon 600.

An exemplary embodiment of a closure device will now be briefly described in the context of the environment of FIG. 1, with some additional details of the closure device being provided further below.

At some point during the aforementioned procedure, the incision in the artery is utilized for whatever medical purposes associated with the utility of the incision. After such utilization, there is utilitarian value in closing the incision. An exemplary embodiment of a closure device for closing the incision will now be described in the context of the artery 1026.

FIG. 2A depicts an exemplary closure device 85 closing puncture 1024. The closure device 85 includes toggle 30, plug 50 (often referred to in the art and herein as a sealing member or collagen pad, or simply collagen), lock 60, and suture (also referred to in the art and herein as filament) 80, in the fully deployed state with the suture 80 cut below the skin level 1028 (the occlusion balloon is depicted in the uninflated/deflated condition. FIG. 2B depicts a cross-sectional view of the artery 1026, which details the fit of the toggle 30 to the internal diameter of the artery, and also depicts the profile of the toggle 30 with respect to the longitudinal axis of the artery 1026.

FIGS. 2A and 2B depict by way of example the closure unit 85 (comprising toggle 30, collagen 50, lock 60, and suture 80) in the fully deployed state with the suture 80 cut below the skin level, and the occlusion balloon deflated to re-establish blood flow in the vessel and depict the fit of the toggle 30 to the internal diameter of the vessel, highlighting the low profile of the toggle design, as seen along the longitudinal axis of the vessel.

In an exemplary embodiment, the closure device 85 can correspond to any of the above referenced applications as modified to close such a large opening in the artery (e.g., an opening large enough to permit a sheath of 18F to fit through as depicted in the FIGS.) and/or to provide an alternate access pathway if needed during the procedure in which the method is executed.

For example, suture (filament) 80 can correspond to filament 34 of U.S. patent application Ser. No. 13/111,653 (hereinafter, the '653 application) filed on May 19, 2011, entitled DEPLOYMENT INSTRUMENT FOR CLOSURE DEVICE FOR PERCUTANEOUSLY SEALING PUNCTURES, the teachings of the '653 application relating to the construction and features of the filament being incorporated by reference herein for use in an embodiment herein. Lock 60 can correspond to lock 36 of the aforementioned '653 application (or any other lock detailed therein and variations thereof), the teachings of the '653 application relating to the construction and features of the lock being incorporated by reference herein for use in some embodiments herein. Collagen 50 can correspond to plug 30 of the aforementioned '653 application, although it is noted that the size of plug 30 may vary from that disclosed in the '653 application, the teachings of the '653 application relating to the construction and features of the plug 30 being incorporated by reference herein for use in an embodiment herein.

While the toggle 30 is different in size and geometry from that explicitly disclosed in the '653 application with respect to that anchor 32 detailed therein, in an exemplary embodiment, the toggle 30 corresponds to the anchor 32 of the '653 application in a modified form in accordance with the teachings detailed herein and/or variations thereof, the applicable teachings of the '653 application relating to the construction and features of the anchor 32 being incorporated by reference herein for use in an embodiment herein.

In an embodiment, the suture 80 is a braided multifilament size 2-0 PLLA suture. The suture 80 can be made from any synthetic absorbable plastic material that degrades as needed.

The plug 50 comprises a strip of a compressible, resorbable, collagen foam which includes one or more apertures through which portions of the suture 80 extend. In an embodiment, the plug 50 is a collagen pad made of a fibrous collagen mix of insoluble and soluble collagen that is cross linked for strength. In an embodiment, the collagen may be obtained from the connective tissue of animals. The collagen may be purified from the subdermal layer of cowhide.

The lock 60 comprises a cylindrical piece of resorbable iron and/or stainless steel crimped in a manner to provide a limited amount of resistance to movement along the suture 80.

An embodiment of the toggle 30 is constructed of a 50/50 polylactic-cogycolic acid or other synthetic absorbable polymer that degrades in the presence of water into naturally occurring metabolites (e.g., water and $CO_2$). In an embodiment, the toggle 30 is a monolithic structure formed by a bio-absorbable polymer.

It is noted that the aforementioned closure device 85 is an exemplary closure device, and alternate embodiments of such may be used in some embodiments. By way of example only and not by way of limitation, the aforementioned crimped lock may not be present, and instead, the filament is looped and/or suturing is utilized to hold the relative locations of the elements of the closure device 85 (e.g., plug 30 and toggle 30). By way of example and not by way of limitation, the closure device may correspond to, scaled for application with large bore application or unscaled, that detailed in U.S. Pat. No. 5,282,827 (hereinafter, the '827 patent) and/or variations thereof, the contents of which are incorporated herein by reference in their entirety with respect to the closure device taught therein. Further by way of example and not by way of limitation, the closure device may correspond to, scaled for application with large bore application or unscaled, that detailed in U.S. Pat. No. 5,662,681 (hereinafter, the '681 patent) and/or variations thereof, the contents of which are incorporated herein by reference in their entirety with respect to the closure device taught therein. Any device, system and/or method of closing the puncture that utilizes a component that fits into the artery to provide a reaction element (e.g., toggle 30) against a force applied thereto associated with closing the puncture and/or any device, system and/or method of closing the puncture that utilizes a plug (e.g., collagen plug 50) may be used in some embodiments. In some other embodiments, any device, system and/or method of closing the puncture may be utilized.

An exemplary puncture (wound) of which the teachings detailed herein and/or variations thereof can be utilized to close or otherwise be associated with is a puncture in an artery having a diameter (inner or outer) of about 10 mm, although such teachings can also be applicable to such having a diameter (inner or outer) of about 5, 6, 7, 8, 9, 10, 11, 12 and/or about 13 mm or more, or any value in between these values and/or any ranges encompassing some or all of these values (including ranges being bounded by the in between values). In an exemplary embodiment, the puncture extends over an arc, transverse to a longitudinal axis of the artery (about the circumference normal to the longitudinal axis) of about 90 degrees, although in some embodiments, the arc extends 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 and/or about 180 degrees, or any value in between these values and/or any ranges encompassing some or all of these values (including ranges being bounded by the in between values). By way of example, the puncture may extend along an arc having a length of 8 mm, although in some embodiments, the length is about 3, 4, 5, 6, 7, 8, 9, 10, 11, 12, 13, 14 and/or about 15 mm or any value in between these values and/or any ranges encompassing some or all of these values (including ranges being bounded by the in between values).

As noted above, some additional exemplary features of the components that make up the closure device 85 are further detailed herein. Prior to that, however, a brief discussion of an exemplary deployment instrument is provided (with additional details pertaining to the deployment instrument being provided further below) for deploying a closure device such as closure device 85 and/or other equivalents thereof and/or variations thereof.

FIG. 3A depicts an exemplary deployment instrument 100 according to an exemplary embodiment, configured to deploy the closure device 85. As described herein, deployment instrument 100 includes a closure device 85 and a guide wire 20. However, in other embodiments, the deployment instrument may not include one or both of these elements.

Briefly, deployment instrument 100 is configured to be inserted into sheath 10. Deployment instrument 100 includes a release tube 40 and a handle 110. Release tube 40 is configured to move relative to handle 110 and release tube support 42 along longitudinal axis 101 via actuation of lever 90 clockwise or counter-clockwise relative to the handle, as depicted by arrow 102. That is, movement of lever 90 moves release tube 40 (sometimes referred to herein as restraining tube 40) inward/proximal to release the toggle 30.

Figure 3B:
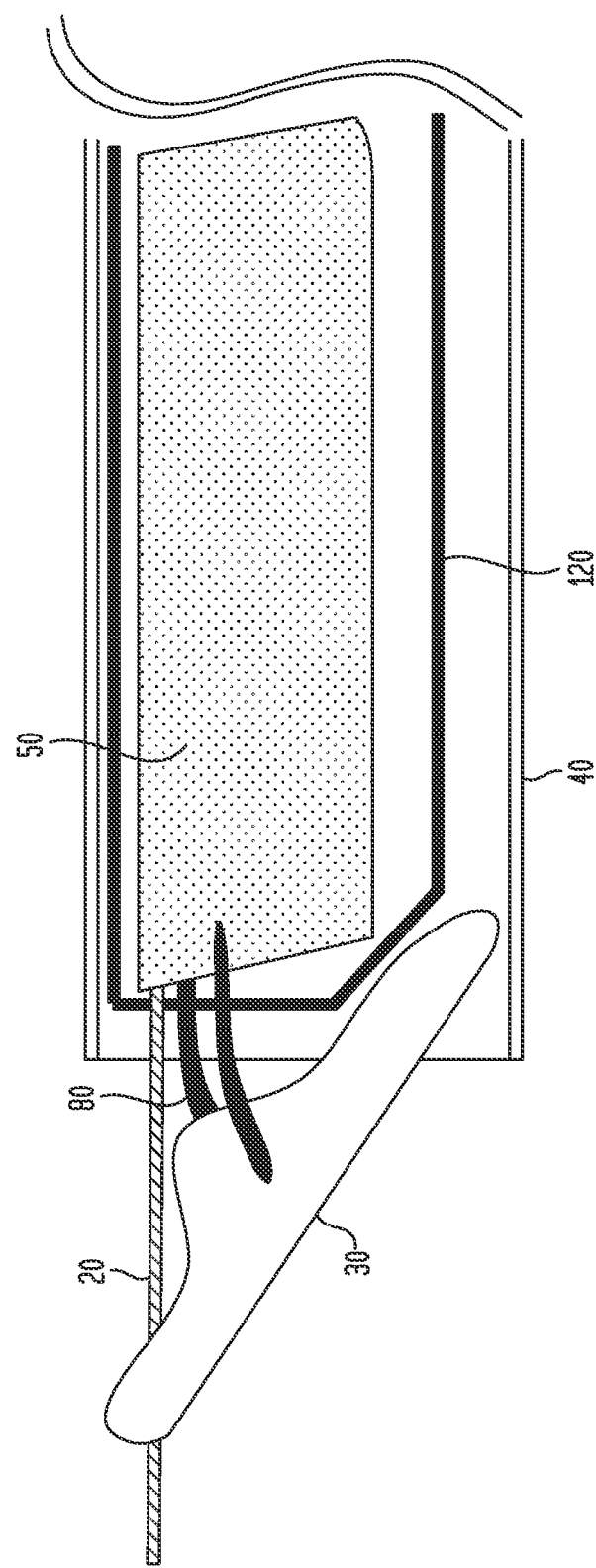
FIGS. 3B-3F depicts additional details of the deployment instrument of FIG. 3A.

More particularly, FIG. 3B depicts a cross-sectional view of the distal end of the deployment instrument 100, depicting additional components of the deployment instrument 100. As may be seen, deployment instrument 100 includes a delivery tube 120 that is located within release tube 40. The plug 50 of closure device 85 is located in the delivery tube 120, with filament 80 extending past plug 50 to toggle 30. It is noted that plug 50 may partially extend outside of tube 120. In an exemplary embodiment, delivery tube 120 corresponds to a carrier assembly (which can include only the delivery tube or can include additional components).

Figure 3C:
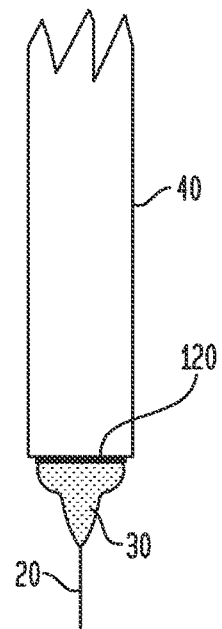
Figure 3D:
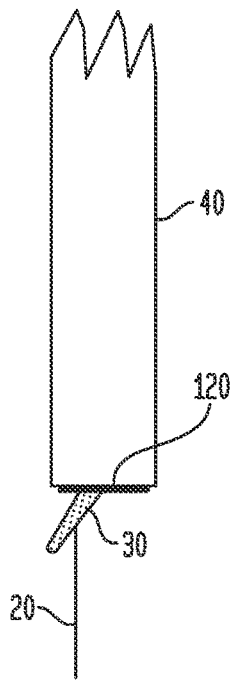

As may be seen, toggle 30 is located such that it is at least partially located in the release tube 40. In some embodiments, it may be fully located in the release tube 40 (i.e., no part of the toggle 30 extends past the distal tip of the tube 40. Toggle 30 is held in place by filament 80. As will be described in more detail below, guide wire 20 extends through delivery tube 120 and release tube 40, as well as through toggle 30 and/or plug 50. In this regard, FIG. 3C depicts a top view of the distal end of deployment instrument 100, with FIG. 3D depicting a side view thereof for comparison purposes. As may be clearly seen in FIG. 3C, the guide wire 20 extends through toggle 30 (through the longitudinal center of the toggle 30). In an exemplary embodiment, the association of the guide wire 20 with the toggle 30 as detailed herein and/or variations thereof can have utility in that such may ensure or otherwise effectively and/or substantially increase the statistical probability (at least with respect to that in the absence of the guide wire association) that the toggle is at least generally if not substantially or about perfectly centered relative to the incision in the artery.

In an exemplary embodiment, irrespective of the presence or absence of the guide wire 20, the plug 50 is held within delivery tube 120 in a manner that is similar to and/or a manner that is the same as that associated with the plug 30 tubular carrier 102 of the '653 application, the teachings thereof relating to such being incorporated by reference herein for use in an embodiment herein.

Figure 3E:
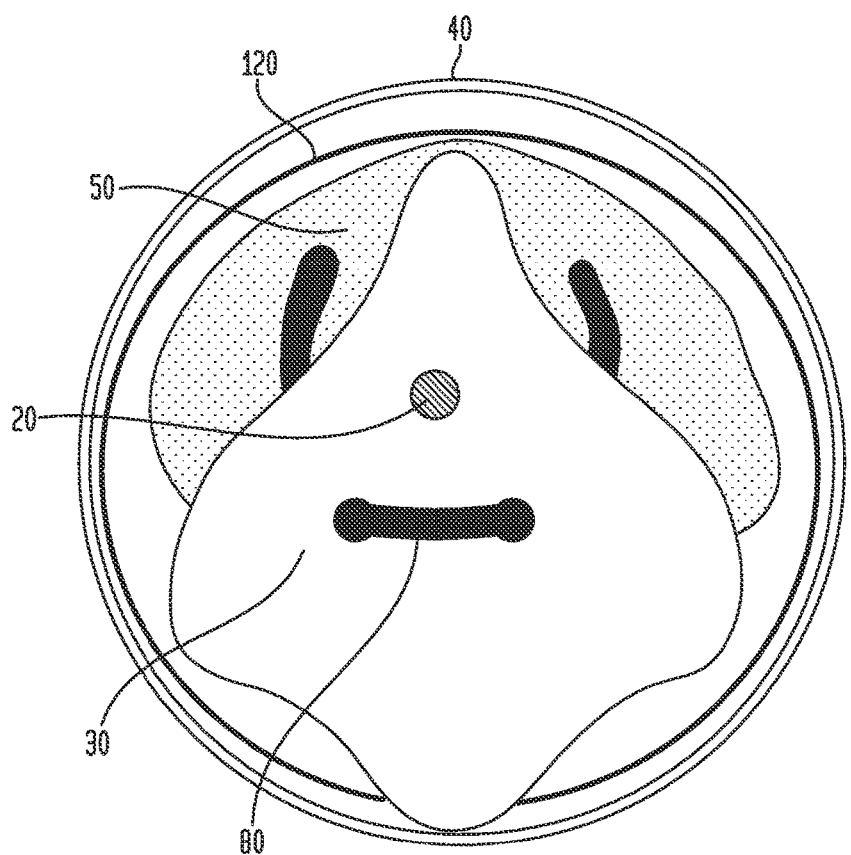

FIG. 3E depicts an end view of the deployment instrument 100 looking at the distal end thereof.

Figure 3F:
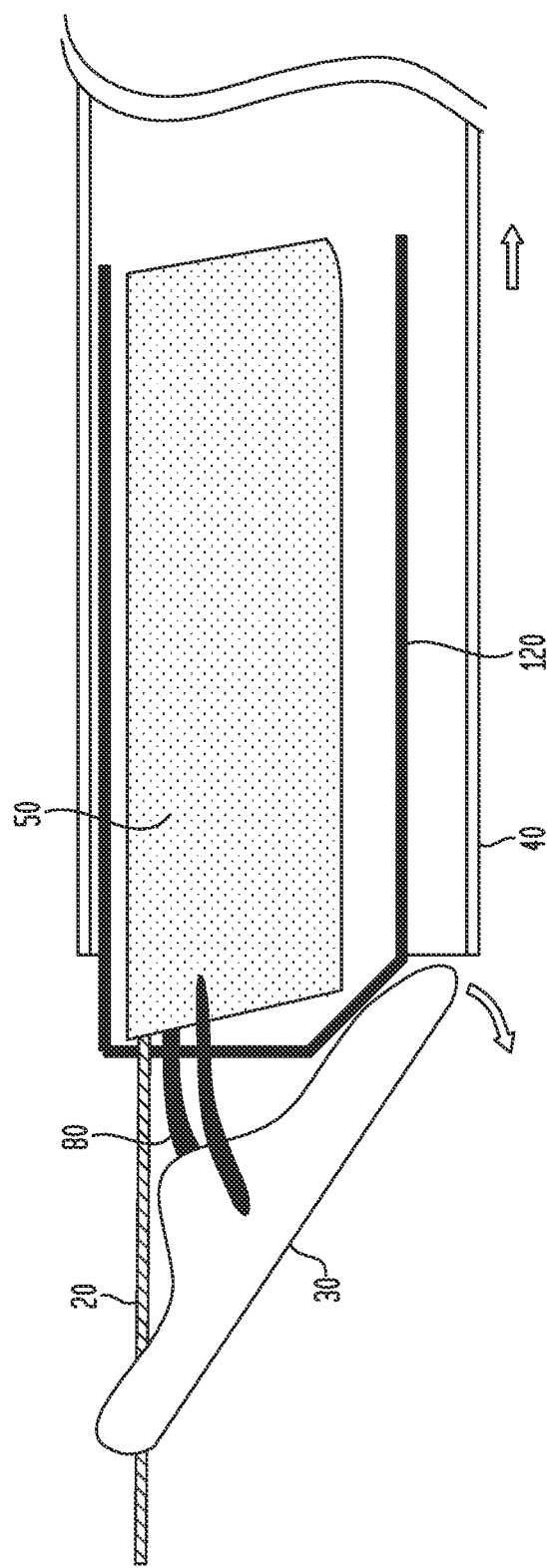

In operation, movement of lever 90 on the delivery handle 110 of the deployment instrument 100 in the direction of arrow 102 moves the release tube 40 in the proximal direction to about the location depicted in FIG. 3F (although the tube 40 may be moved to other locations in other embodiments, such as to a more distal location). As may be seen, the toggle 30 is now completely outside the release tube 40, and is thus "released."

In an exemplary embodiment, the deployment instrument 100 is a fully integrated system that includes the deployment device 85 and the guide wire 20. In an exemplary embodiment, it is packaged (in, by way of example, a sterilized manner). In an exemplary embodiment, it is packaged in a hermetically sealed package. The guide wire 20 may be wound in a winding with a relatively large radius to avoid kinking the guide wire. FIG. 3G depicts an exemplary closure device kit 1000, including deployment instrument 100, closure device 85 and guide wire 20 sterilized and hermetically sealed in package 900. In an exemplary embodiment, kit 1000 may further include an insertion sheath 10 in package 900 and/or in a separate package attached thereto.

It is noted that in an alternate embodiment, the guide wire 20 is not part of the kit and/or the delivery instrument 100. Instead, it is a separate component that is threaded through the toggle 30 and/or the plug 50 after access to the delivery instrument 100 (and thus the closure device 85) is obtained. Accordingly, an exemplary embodiment includes a method whereby a user, such as a physician or an operation room nurse or other professional passes an end of a guide wire through a hole in the toggle 30 or otherwise associates the toggle 30 with the guide wire, followed by deployment of the closure device 85.

Use of the deployment instrument 100 will now be detailed with respect to an exemplary deployment method of deploying the closure device 85.

With the sheath 10 in place as seen in FIG. 1, the deployment instrument 100 is inserted into a proximal end (not shown) of sheath 10, and moved through the sheath 10 until the distal end of the instrument 100 end extends out of the distal end of the sheath 10, approximately as shown in FIG. 4. In an exemplary embodiment, the guide wire 20 extends through the deployment instrument 100, and the deployment instrument 100 slides along the guide wire 20 (guide wire 20 and sheath 10 are generally held stationary, relative to artery 1026, while deployment instrument 100 is moved through the sheath 10). In an alternate embodiment, the guide wire 20 moves with the deployment instrument 100, at least to a certain extent.

More particularly, FIG. 4 depicts the relative locations of toggle 30, the end of the delivery tube 120, and the release tube 40 of the deployment instrument 100 with respect to the distal end of the sheath 10. This positioning is achieved by driving the deployment instrument 100 through sheath 10, over the guide wire 20 and/or with the guide wire 20, until the release tube 40, along with the closure device 85 in general and the toggle 30 in particular, as detailed herein and/or variations thereof (where toggle 30 and plug 50 and some of filament 80 is visible in FIG. 4), is positioned as shown. The positioning can be determined via the use of one or more radiopaque markers 44 and/or 45 on the release tube 40. The user, utilizing fluoroscopic methods, can determine the position of radiopaque marker 45, and thus the release tube 40, relative to the end of the sheath 10. In an exemplary embodiment, the user stops driving the deployment instrument 100 into the sheath 10 upon the marker 45 emerging from the sheath 10 (imaged using fluoroscopic methods). It is noted that other devices, systems and/or methods may be utilized to determine or otherwise estimate the position of the end of the release tube 40 relative to the insertion sheath 10. For example, a channel which permits blood to follow through/along the instrument 100 to a location that is visible by the user upon the instrument 100 being so positioned may be used in some embodiments. An exemplary embodiment utilizes some and/or all of the teachings associated with determining or otherwise positioning introducer sheath 28 and/or device 28 of U.S. Pat. No. 5,282,827, the contents of which associated with such teachings are incorporated herein by reference for use in some embodiments. Any device, system and/or method that will enable the position of the instrument 100 to be determined or otherwise estimated may be used in some embodiments. In an alternate embodiment, the sheath 10 is sized and dimensioned and/or the delivery instrument 100 is sized and dimensioned such that movement of the deployment instrument 100 through the sheath 10 stops at a certain point (e.g., a wall of the deployment instrument 10 abuts the sheath 10) such that the distal end of the deployment instrument 10 extends a distance past the distal end of the sheath 10 a distance having utilitarian value.

As may be seen in FIG. 4, the toggle 30, which in this exemplary embodiment, is smoothly shaped, is partially covered by the release tube 40 upon its emergence from the sheath 10. Because it is exposed, the smoothness has utility in that it can permit relatively smooth entry into the artery and can allow for rearward movement of the closure device within the artery without risk of the toggle 30 catching on any plaque or other obstruction. Given the anatomical nature of the access site and puncture, the release tube 40 (and the delivery tube 100, sheath 10 and guidewire 20 will be slightly curved as may be seen in FIG. 5. This curvature provides a biasing force on the toggle 30 for the release actions.

Upon positioning of the deployment instrument 100 at the desired position relative to the distal end of the sheath 10 (i.e., at the position depicted in FIG. 4), the lever 90 is rotated relative to the rest of the instrument 100 in a direction and by a sufficient amount to retract the release tube 40 a utilitarian distance relative to delivery tube 120, thereby entirely exposing the toggle 30. FIG. 5 depicts such an exemplary retraction. As may be seen, guide wire 20 extends through toggle 30 after retraction of the release tube 40.

Next, sheath 10 is withdrawn from the approximate position depicted in FIG. 5. However, prior to this, balloon 600 optionally can be inflated as shown in FIG. 5. Because the sheath 10 may exit the puncture 1024 when the sheath 10 is withdrawn from the artery, the balloon is inflated under a low pressure to block blood flow from a proximal position at least prior to fully withdrawing the distal end of the sheath 10 from the artery (where blood flow flows from left to right with respect to the frame of reference of FIG. 5).

As just noted the insertion sheath 10 is withdrawn from its previous position, either partially and/or fully out of the artery 1026. FIG. 6 depicts withdrawal of the insertion sheath 10. While the sheath 10 is withdrawn, the relative position of the deployment instrument 100 relative to the artery can change, either by the same amount or by a lesser or greater amount, although in other embodiments, its location relative to the artery may remain the same. Any movement or lack thereof of the instrument 100 relative to the artery may exist in some embodiments providing that it does not negate the utilitarian value of the embodiment. Some such movement may be seen by comparing FIG. 6 to FIG. 5. In this regard, FIG. 6 depicts the deployment instrument 100 in general, and the closure device 85 carried thereby, in a position relative to the puncture 1024 having utilitarian value.

It is noted that in an exemplary embodiment, plug 50 can be withdrawn from tube 120 without contacting the sheath 10 and/or at least without contacting the interior of the sheath 10. This may, in some embodiments, eliminate the possibility that the plug 30 might become stuck in the sheath 10—during the deployment procedure as it expands once leaving the tube 120.

In an exemplary embodiment, a contrast agent is injected distal to the balloon 600. Contrast agent can indicate any leakage at the puncture site and can additionally provide for an outline of the toggle 30 using fluoroscopic methods.

FIG. 4A shows the device including radiopaque marker 44 positioned near the puncture. Because the sheath 10 may exit the puncture during this step, balloon 60 is inflated under a low pressure to block blood flow from a proximal position. Contrast is injected distal to balloon 60, which indicates any leakage at the puncture site and additionally provides for an outline of toggle 30 on the fluoroscope. The sheath 10 and/or the tube 40, are retracted (moved in the direction that would withdraw them from the patient) until the distal radiopaque marker aligns with the puncture, as will be seen fluoroscopically. Given the anatomical nature of the access site and puncture, release tube 40 and sheath 10 will be curved slightly, as may be seen in FIG. 5. This curvature provides a biasing force on the toggle 30 for the release step, discussed with respect to FIG. 6.

Still referring to FIG. 6, FIG. 6 depicts how the toggle 30 will be released from the biased state with retraction of the release tube 40. The release orients the toggle 30 parallel to the vessel axis. Release is confirmed by the alignment of the distal radiopaque marker 44 with the end of the sheath 10 and/or markings on the handle (not shown). Note that vessel occlusion is maintained during this action, and an outline of the toggle will be visible to the user on the fluoroscope (as will be detailed below, the toggle 30 may include material that is readily apparent through fluoroscopy. Note further that, in an exemplary embodiment, the contact of the most distal portion of the toggle 30 with the artery wall forces the toggle 30 to rotate clockwise upon sufficient movement of the release tube 40, thus aligning the toggle 30 in a manner that will statistically improve the chances that the toggle 30 will be sufficiently aligned so as to statistically reduce the likelihood (at least in comparison to the absence of such alignment), if not substantially eliminate or completely eliminate the likelihood that it will be pulled out of the artery during subsequent actions. It is noted that in some embodiments, radiopaque marker(s) may be located on the sheath 10, such as, by way of example, at the distal end/tip of the sheath 10. Such may be used, in some exemplary embodiments, to determine the position of the sheath 10. For example, a sheath marker may be utilized to determine the position/estimate the position of the distal end of the sheath relative to the puncture. Such may have utility in determining whether or not to further retract the sheath 10 from the artery based on the location of the marker. Still further by example, such may be used to determine the location of certain components of the deployment instrument 100 (e.g., the release tube 40 and/or the deployment tube 120, such as, by way of example, based on radiopaque markers thereon, etc.), relative to the sheath 10.

Figure 7:
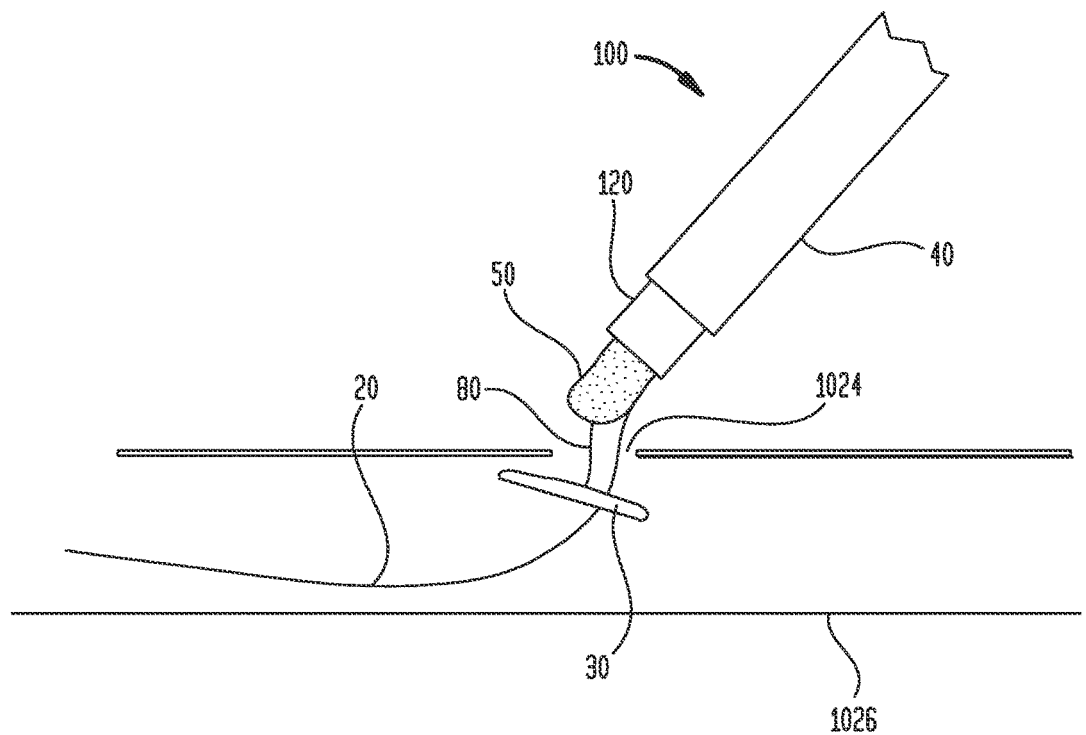
FIGS. 7-8B are diagrams showing how the device is deployed to seal the puncture.

Next, the delivery instrument 100 is moved proximally such that the distal tip thereof is moved from the location depicted in FIG. 6 to at least about the location depicted in the functional schematic of FIG. 7 (with sheath 10 not shown for clarity). This results in plug 50 being completely withdrawn from the artery and toggle 30 being drawn closer to the puncture 1024 and/or substantially or completely against the puncture 1024. Guide wire 20 may move along with delivery instrument 100 partially and/or fully, or may remain stationary while the delivery instrument 100 is moved to the location of FIG. 7 and locations thereabouts. Continued movement of the delivery instrument 100 away from the puncture, to a location such as that depicted by way of example in FIG. 8A, pulls toggle 30 closer to the puncture and/or completely against the puncture, and also pulls plug 50 out of the delivery tube 120 and, as a result of a pulley action/synching action/lassoing action between the filament 80, the toggle 30 and the plug 50, the plug is pulled towards the toggle 30 and thus the puncture 1024 (in some embodiments such that it contacts the artery wall), with guide wire 20 having the movements or lack of movements detailed above. Below, an exemplary device that has utilitarian value in moving the plug 50 relative to the toggle 30 is described.

Next, the delivery instrument 100 is moved further away from the puncture to expose some additional components therein, such as, for example, a tamper, the lock if not already exposed, and additional filament 80 (by exposed, it is meant that the delivery tube 120 (or other component of the delivery instrument 100) is pulled past these components such that the components emerge from the distal end of the tube 120 (or other component that carries these components)). It is noted that such exposure may be achieved by pulling the handle 110 of the delivery instrument 100, which results in pulling of the delivery tube 120 (and the release tube 40), and other components.

Figure 8A:
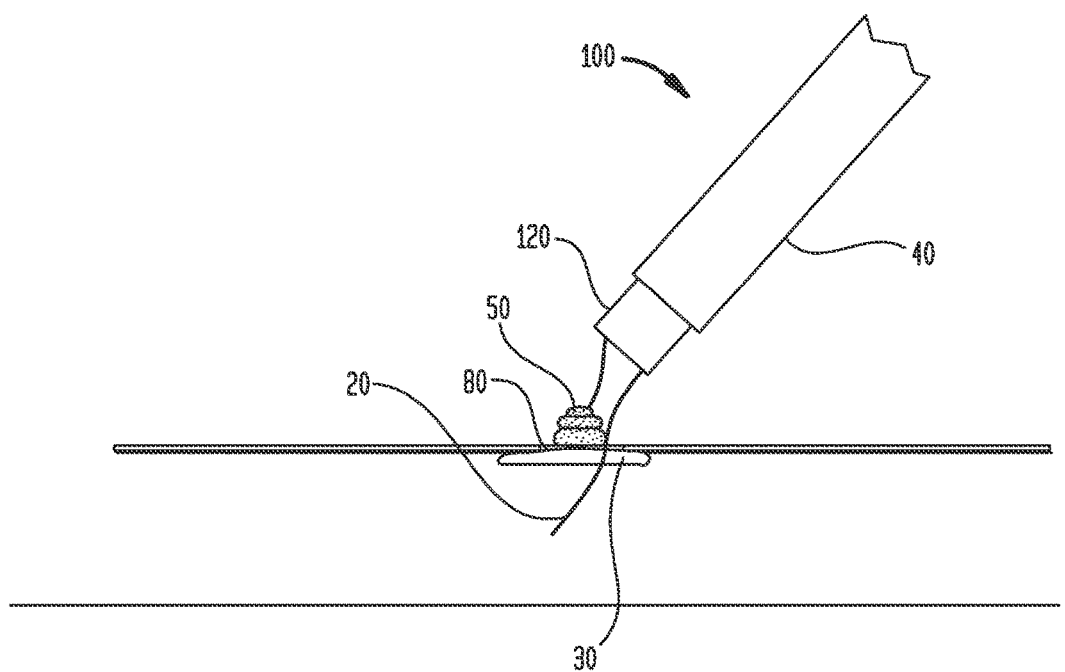
Figure 8B:
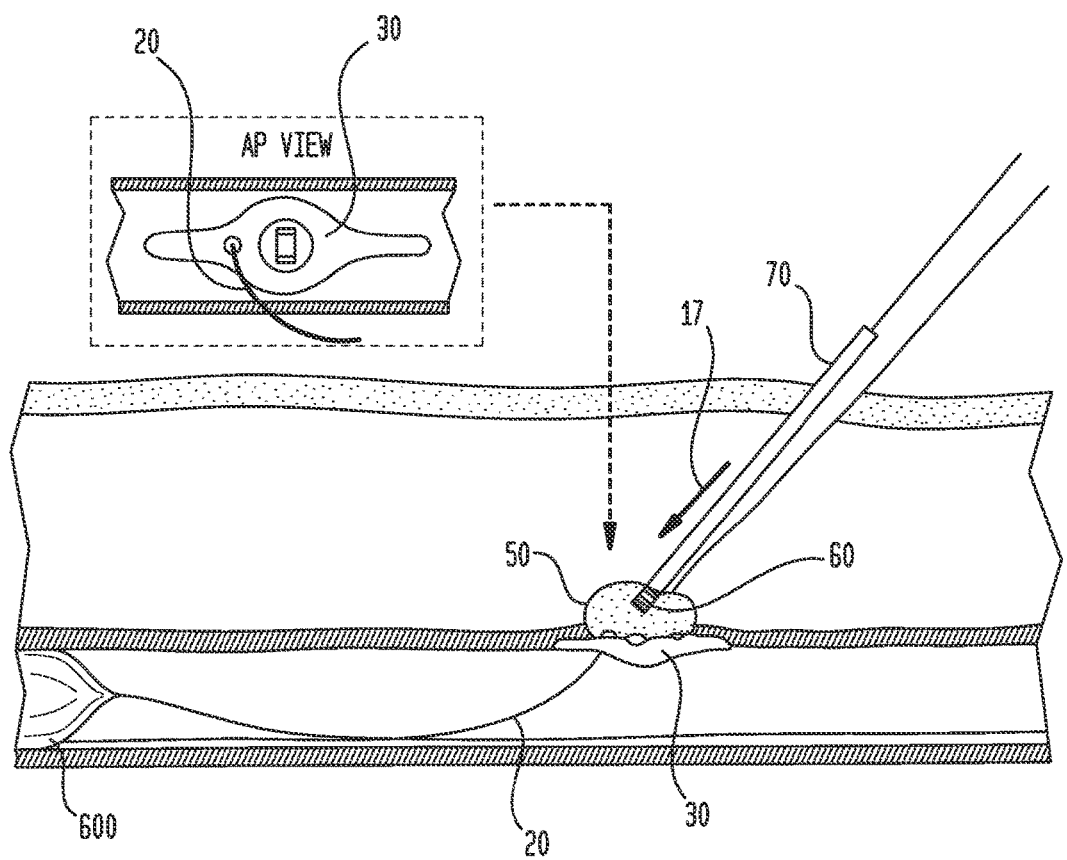

FIG. 8B depicts an exemplary result of such movement of delivery instrument 10, where tamper 70 has been exposed from the delivery tube 100 (not shown in FIG. 8B, as it is exemplary moved out of the field represented by FIG. 8B). It is noted that the procedure for exposing the tamper 70 and the tamper 70 itself may correspond to the teachings of such exposure and the tamper detailed in the '827 patent, the '681 patent and/or the '653 application, the contents of which related to such exposure and the tamper being incorporated by reference herein for use in some embodiments (although it is noted that below, an alternate tamper and an alternate method of exposure and an alternate device for achieving such exposure is detailed).

More particularly, FIG. 8A represents by way of example how the retracting the sheath 10 and deployment instrument 100 can position the toggle 30 to cover the interior of the puncture. FIG. 8B represents how further retraction of the deployment instrument 100 will deploy the contents of the delivery tube 100, namely the collagen 50, lock 60, and tamper tube 70, which will allow the user to compress the collagen 50 in place and deploy the lock 60 (in embodiments that utilize such a lock). In an exemplary embodiment, these components correspond to those disclosed in the '827 patent, the '681 patent and/or the '653 application, and variations thereof, as might be scaled for use to procedures disclosed herein. Moreover, the steps of achieving the results depicted in these FIGS. may include some and or all of the method steps disclosed in any of the '827 patent, the '681 patent and/or the '653. As noted above and is further detailed below, toggle 30 position can be confirmed fluoroscopically.

After utilitarian placement of the plug 50 relative to the toggle 30 and/or puncture 1024, the plug 50 is locked in place by tamping lock 60 with tamper 70 in the distal direction (as represented by arrow 17) as described by way of example in the '653 application. Again, an exemplary device that has utilitarian value in tamping lock 60 is described below.

It is noted that in an exemplary embodiment, some or all of the features associated with the methods of delivering the closure device 85 (including securing the closure device in place) can correspond to those variously taught in the '681 patent, the '827 patent and/or the '653 application as implemented utilizing the teachings detailed herein in general and/or the teachings applicable to the delivery instrument 100 and sheath 10 in particular, the applicable teachings of those patents and applications being incorporated by reference herein for use in some embodiments. By way of example, the teachings of the '653 application associated with pulling the plug towards the toggle prior to locking the plug in place may be used in some embodiments.

As detailed above, an exemplary embodiment utilizes a toggle that maintains an association with a guide wire. Some exemplary associations will now be described.

Figure 9A:
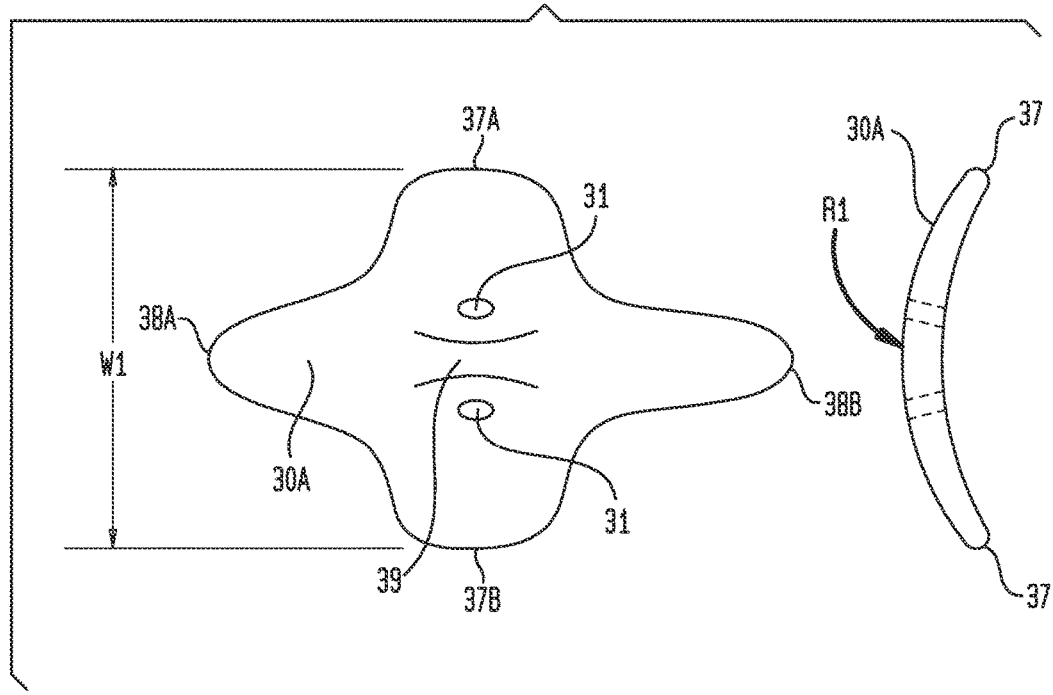
FIGS. 9A-9F depict exemplary toggle-guide wire associations.

FIG. 9A depicts an exemplary embodiment of a toggle 30A, which can be in some embodiments a large bore toggle, usable in at least some embodiments herein and methods herein. As may be seen, toggle 30A includes two holes 31 through which filament 80 may extend, as described in greater detail below. (Additional features of the structural arrangement of the toggle are also described below.) Toggle 30A may be utilized in an embodiment where there is no association between the toggle and the guide wire.

In an exemplary embodiment, toggle 30A and/or the other toggles detailed herein and/or variations thereof are configured to utilitarianly fit to a 10 mm diameter (interior) artery. The toggle 30A has a curved profile, as may be seen in FIG. 9A, which depicts both a top view and a side view of the toggle 30A. In an exemplary embodiment, the top profile of the toggle 30A has a generally circular profile having a radius of R1, which can be about 5 mm, in an unrestrained configuration, although in some embodiments, the profile may be a radius of about 4 mm, 5 mm, 6 mm, 7 mm, 8 mm, 9 mm, 10 mm, 11 mm and/or about 12 mm, or any value in between these values and/or any ranges encompassing some or all of these values (including ranges being bounded by the in between values). It is noted that in an exemplary embodiment, the aforementioned radii encompass a profile that is not exactly circular, but instead is elliptical (hence the use of the term "about", which, as used herein with respect to any teaching herein, unless otherwise noted, does not exclude exact values and the use of about also includes embodiments not so qualified (i.e., includes exact numbers, tolerance as would be understood in the art). In an exemplary embodiment, the toggle has an unrestrained width W1 of about 6 mm, although in some embodiments, the width W1 may be about 2 mm, 3, 4, 5, 6, 7, 8, 9 and/or about 10 mm, or any value in between these values and/or any ranges encompassing some or all of these values (including ranges being bounded by the in between values).

In an exemplary embodiment, the radius R1 and/or the width W1 and/or other pertinent dimensions are such that when applied to a given artery, the wing tips 37A and 37B, as opposed to the longitudinal tips 38A and 38B, which run parallel to the longitudinal axis of the artery) contact the artery wall prior to the center 39 of the toggle 30A. In an exemplary embodiment, the toggle 30A is made of elastomeric material and/or is of a material such that, when sized and dimensioned for use, allows the toggle 30A to flex (elastically and/or plastically) such that the radius R1 and/or width W1 decreases slightly (to about the interior diameter of the artery—with or without expansion of the artery (in some cases, the artery is about a zero elasticity tissue, such as may be the case for statistically very elderly patients for a population in the United States of America or Europe)) to conform to or about conform to the interior diameter, upon tensioning of the filament as detailed herein and/or variations thereof. In this regard, the upper surface may be characterized as being slightly less curved and/or slightly flatter than the interior surface of the artery (as taken on a plane normal to the longitudinal axis of the toggle and the artery, which in some embodiments, will be parallel or substantially parallel and/or effectively parallel during application).

In an exemplary embodiment, the longitudinal distance of the toggle 30A (tip 38A to tip 38B) is about 16 mm, although in some embodiments, this distance may be about 6 mm, 7, 8, 9 10, 11, 12, 13, 14, 15, 16, 17, 18, 19, 20, 21, 22, 23, 24, 25, 26 and/or about 27 mm, or any value in between these values and/or any ranges encompassing some or all of these values (including ranges being bounded by the in between values).

Figure 9B:
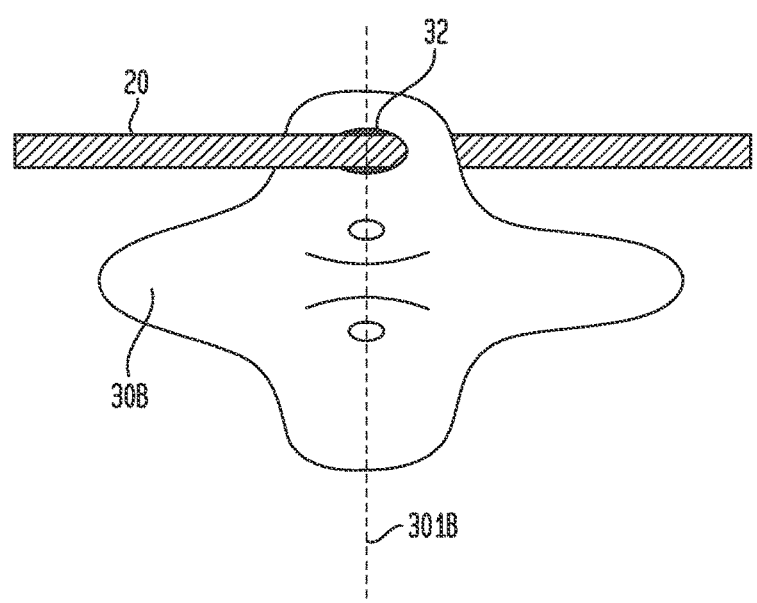

FIG. 9B depicts an alternate toggle, toggle 30B, which includes a hole 32, as may be seen, which accommodates the guide wire 20. Particularly, guide wire 20 extends through hold 32, and hole 32 permits guide wire 20 to slide or otherwise move therethrough. As may be seen, Hole 32 is located at about the lateral center of the toggle 30B (lateral center being on the lateral axis 301B, as may be seen) as well as or in the alternative, centered along the axis of the suture holes 31, which may be slightly offset from the lateral axis 301B.

Figure 9C:
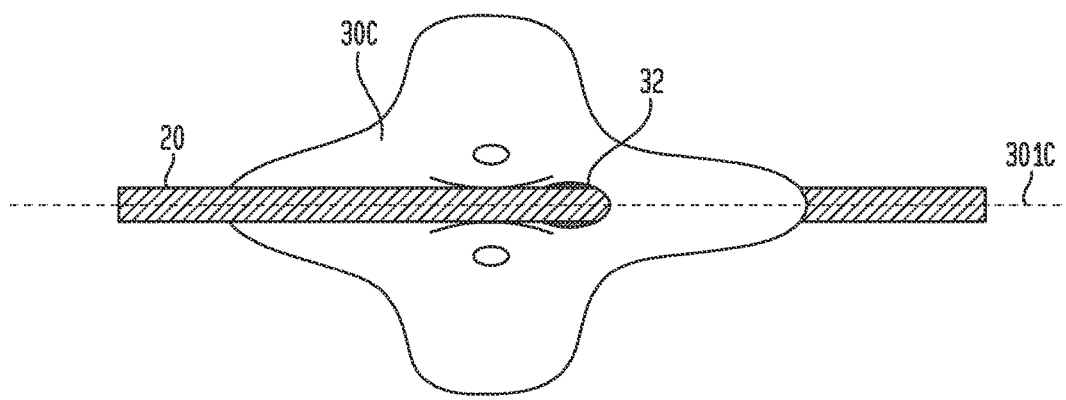
Figure 9D:
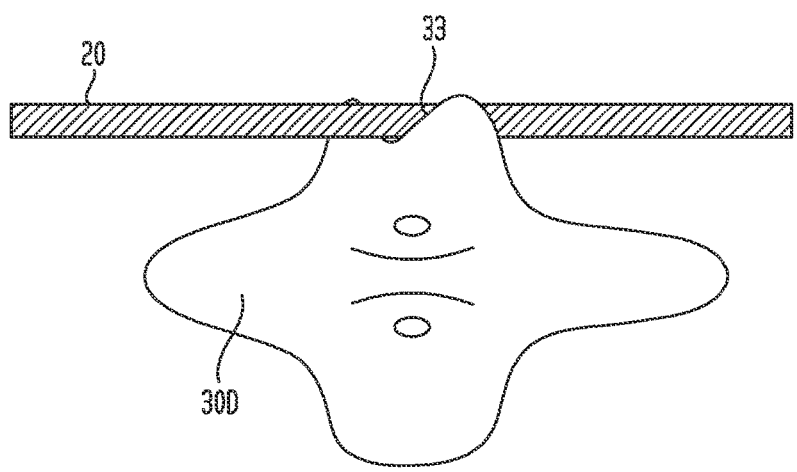

In an exemplary embodiment, the location of hole 32 is different than that depicted in FIG. 9B. For example, FIG. 9C depicts hole 32 located in the longitudinal center of the toggle 30C (longitudinal center being on the longitudinal axis 301C, as may be seen), and/or, the hole 32 is longitudinally in between the holes 31 in the toggle. Any placement of hole 32 in the toggle that will enable the teachings detailed herein and/or variations thereof to be practiced or otherwise to have utilitarian value may be implemented in some embodiments. Also, in some embodiments, association of the toggle with the guide wire is achieved not by a hole through the toggle, but via a notch on the edge of the toggle, as may be seen in FIG. 9D, where toggle 30D has a notch 33. Such an embodiment can further include one or more holes through which the guide wire extends. An exemplary embodiment that achieves association with the guide wire and the toggle via a notch that has a C-Shaped cross-section (or other equivalent cross-section that achieves the following functional result) such that the guide wire is "trapped" or otherwise retained therein. For example, if the C-shaped interior of the notch is such that the distance between the ends of the C is less than the maximum diameter of the guide wire 20, the guide wire should be retained therein. Alternatively, the notch exists, but the guide wire is not trapped or otherwise retained in the notch. Any device, system and or method of achieving and/or maintaining an association between the guide wire and the toggle may be practiced in some embodiments detailed herein and/or variations thereof.

Figure 9E:
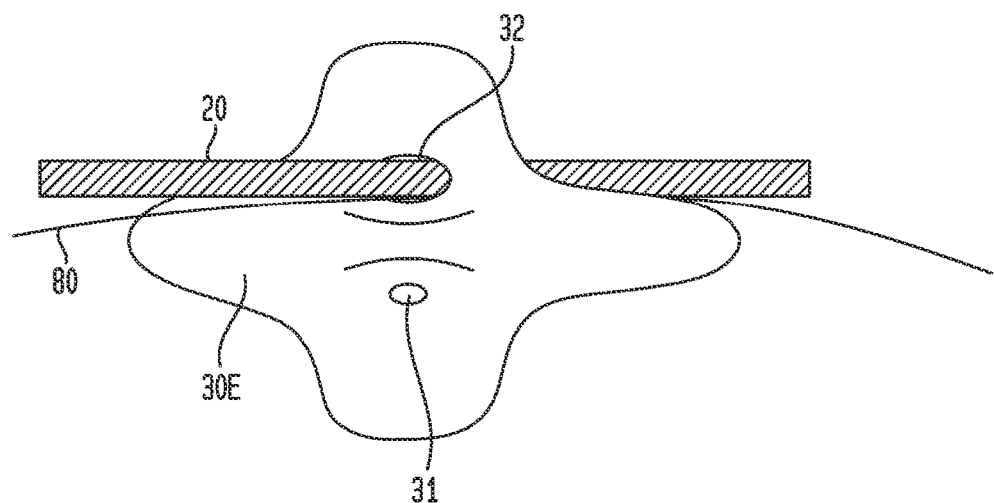

In an alternate embodiment, a suture hole may be utilized as a hole to achieve association between the toggle and the guide wire/a hole for the guide wire may be utilized to pass a filament 80 therethrough. FIG. 9E depicts such an exemplary toggle 30E. Such may be achieved by making a suture hole with a larger diameter than that which is would otherwise be the case for association with a suture alone.

Figure 9F:
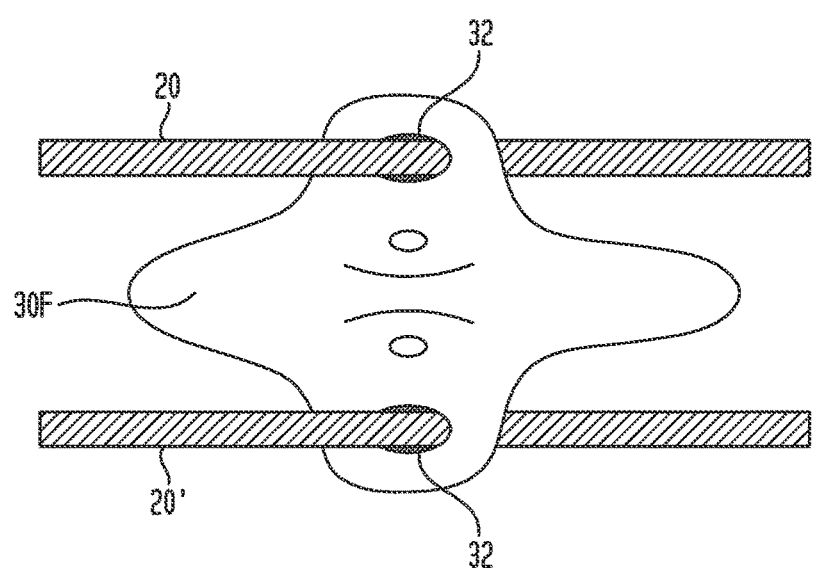

FIG. 9F depicts an alternate embodiment where two holes 32 are utilized to respectively associate two guide wires 20 with the toggle 30F. Accordingly, such an exemplary embodiment may utilize two guide wires. In some embodiments, three or more guide wires and a corresponding number or different number of association devices (e.g., holes, notches, etc.) are utilized.

Figure 10A:
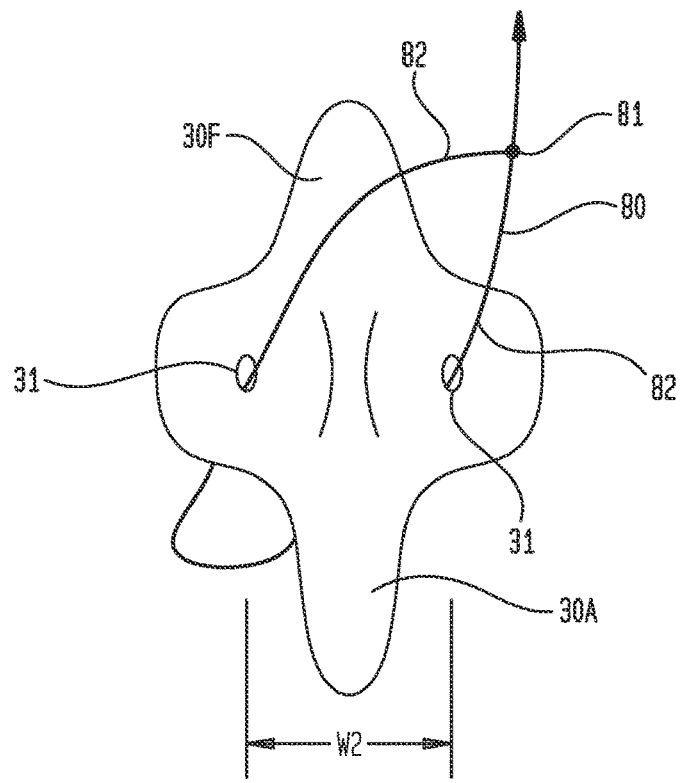
FIGS. 10A-C depict exemplary toggle-filament associations.

FIG. 10A depicts an exemplary filament 80 weave through holes 31 of an exemplary toggle 30F, with element 81 corresponding to, for example, loop 50A and winding 52 as detailed in the '653 application, the contents of which related to the loop and winding thereof being incorporated herein by reference in an exemplary embodiment. It is noted that the exemplary embodiment of FIG. 10A includes a suture hole 31 spacing width W2 that is wider than that depicted in the exemplary toggle of FIG. 9A. In an exemplary embodiment, the holes 31 are about 4 mm from one another (W2 equals about 4 mm), although in some embodiments, W2 is about 2 mm, 2.5, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm and/or about 10 mm or any value in between these values and/or any ranges encompassing some or all of these values (including ranges being bounded by the in between values). It is noted that the spacing between the holes 31 of the toggle of FIG. 9A correspond to about 1.5 mm. In an exemplary embodiment, the hole spacing is sized so as to provide sufficient structure that provides utilitarian value with respect to providing sufficient material to react against the tension applied to the filament (e.g., it will not break the toggle during tensioning).

It is noted that the weave depicted in FIG. 10A is applicable to the toggles detailed above and/or below. In exemplary embodiment, element 81 is a collar as detailed in the '653 application. Any device system and or method of achieving the utilitarian value of element 81 (e.g., its use as a collar), which can include permitting the loop 82 established by filament 80 to reduce in diameter (like a lasso or the like) can be used in some embodiments.

Figure 10B:
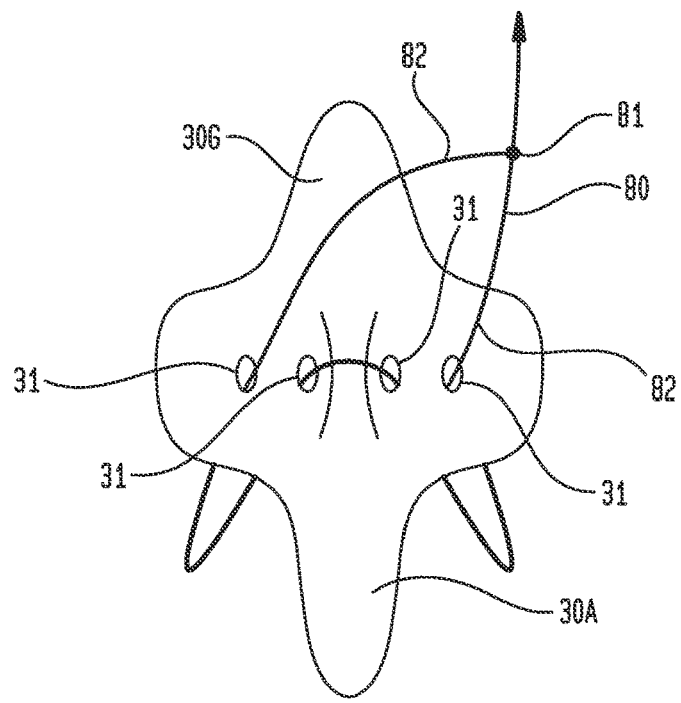

FIG. 10B depicts an alternate embodiment utilizing more than two toggle holes 31. As may be seen, four holes 31 are used, through which filament 80 is threaded. Such an exemplary embodiment can have utility by improving pulley action for compressing the plug 50 (not shown in FIGS. 10A and 10B), as compared to that resulting from the configuration of FIG. 10A and/or FIG. 9A.

Figure 10C:
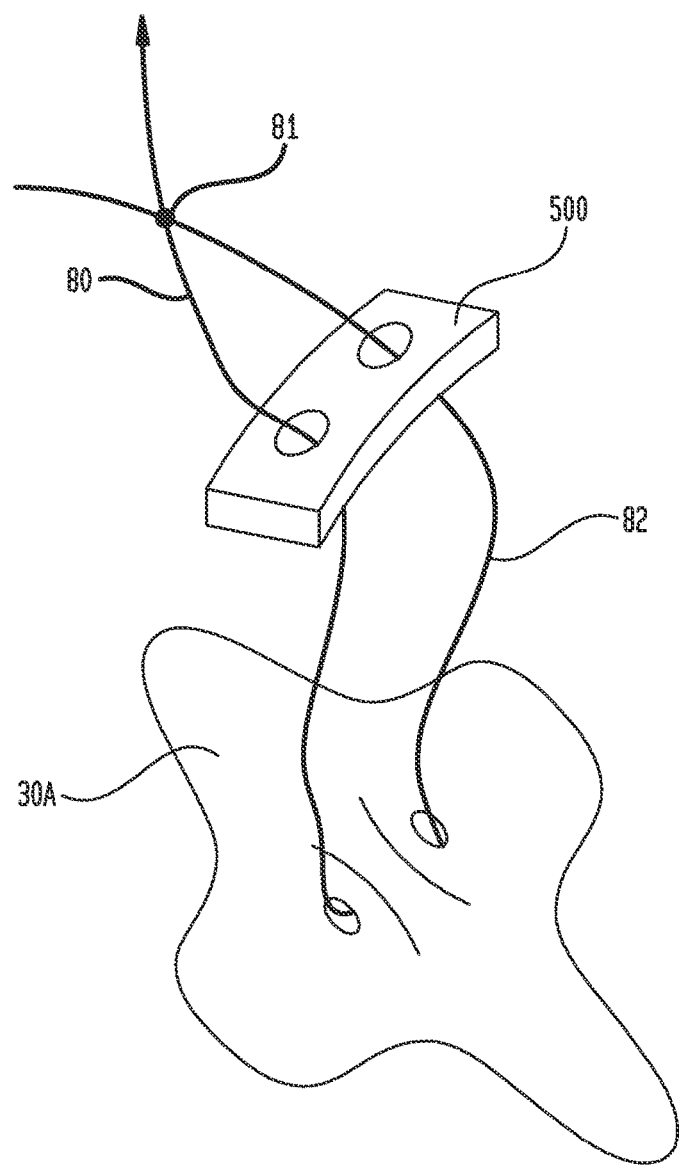

FIG. 10C depicts an alternate embodiment including a washer (resorbable and/or nonresorbable washer) 500 interposed as seen in the loop 82 formed with toggle 30A (or any other toggles described herein and/or variations thereof). Such may provide for utilitarian management of the wound/puncture at the access site. In an exemplary embodiment, washer 500, upon deployment of the closure device 85, becomes located between the vessel wall and the plug 50 (which is interposed in the loop between the toggle 30A and washer 500, but not shown in FIG. 10C), or, alternatively, proximally of the plug 50. In an exemplary embodiment, the distance between the holes of the washer 500 corresponds to the distance between the holes of the toggle 30A, although in an alternate embodiment, the holes have a different spacing than that of the toggle. (It is noted that the aforemementioned hole spacings for the toggle and/or the washer are centerline to centerline dimensions.)

In an exemplary embodiment, the holes of the washer are about 4 mm from one another (W2 equals about 4 mm), although in some embodiments, the distance is about 1 mm, about 2 mm, 2.5, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm and/or about 10 mm or any value in between these values and/or any ranges encompassing some or all of these values (including ranges being bounded by the in between values). It is noted that the spacing between the holes 31 of the toggle of FIG. 9A correspond to about 1.5 mm. In an exemplary embodiment, the hole spacing is sized so as to provide sufficient structure that provides utilitarian value with respect to providing sufficient material to react against the tension applied to the filament (e.g., it will not break the toggle during tensioning).

It is noted that an exemplary embodiment includes a toggle having three holes 81 or more holes. In an exemplary embodiment, the three holes are utilized with a threaded double suture.

As noted above, delivery instrument 100 includes a tamper 70 therein. While some embodiments include a tamper and are otherwise configured according to the tamper of the '827 patent, the '681 patent and/or the '653 application, an exemplary embodiment includes a tamper 71 that provides association between the tamper and the guide wire 20, as will now be described.

An exemplary embodiment of tamper 71 is depicted in FIG. 11, and includes a double-lumen. Specifically, tamper 71 includes lumen 80', through which filament 80 extends, and lumen 20', through which guide wire 20 extends. Lumen 80' is sized and dimensioned, relative to the guide wire 20 and the filament 80, to permit movement of the tamper 71 relative to the filament 80, and lumen 20', in some embodiments, is sized and dimensioned to permit movement of the tamper relative to the guide wire 20, while in other embodiments, it does not permit movement relative thereto.

Figure 11C:
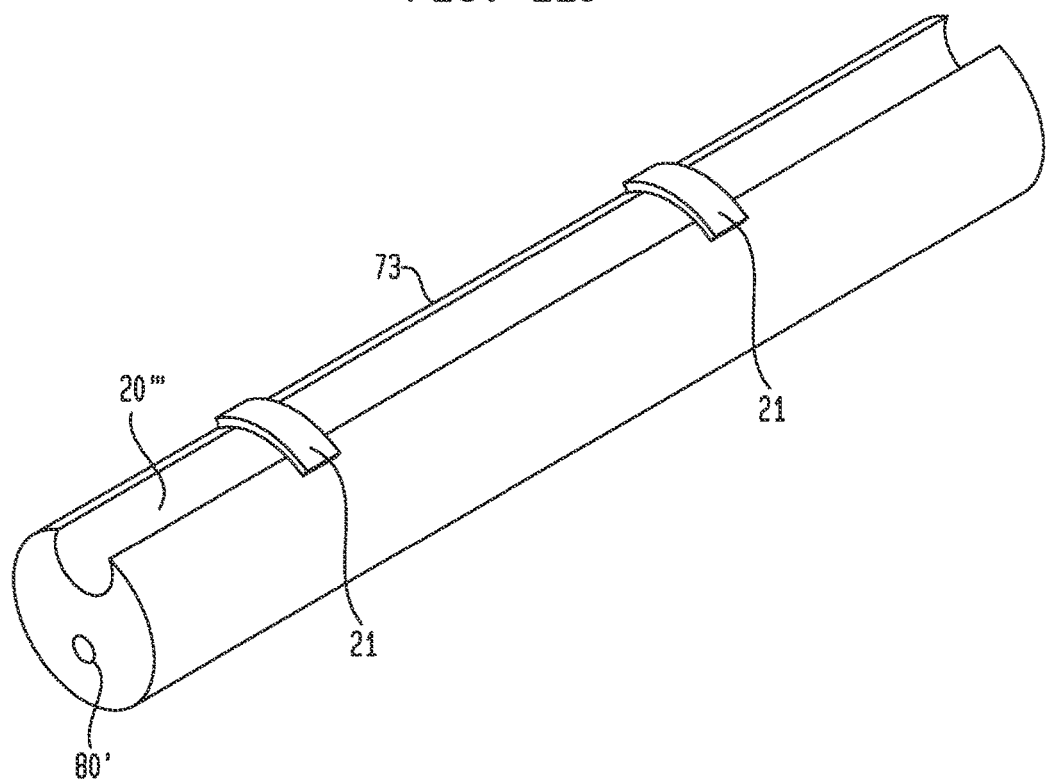

FIG. 11B depicts an alternate embodiment of a tamper, tamper 72, which achieves association with the guide wire via the use of guide wire carriers 20", through which guide wire 20 extends, the functional features of tamper 72 being the same as and/or similar to that of tamper 71. FIG. 11C depicts another alternate embodiment of a tamper, tamper 73, which includes guide wire slot 20''', through which guide wire 20 extends, and is retained therein (slidably or otherwise) via bridges 21 attached to the body of the tamper, the functional features of tamper 73 being the same as and/or similar to that of tamper 71. An exemplary embodiment that achieves association with the guide wire and the tamper does not include the bridges 21, while including the slot. The slot may have a C-shaped cross-section (or other equivalent cross-section that achieves the following functional result) such that the guide wire is "trapped" or otherwise retained therein even in the absence of the bridges 21. For example, if the C-shaped interior of the slot is such that the distance between the ends of the C is less than the maximum diameter of the guide wire 20, the guide wire should be retained therein. Alternatively, the slot exists, but the guide wire is not trapped or otherwise retained in the slot. Any device, system and or method of achieving and/or maintaining an association between the guide wire and the tamper may be practiced in some embodiments detailed herein and/or variations thereof. It is noted that the embodiment of FIG. 11A can have utility in that it provides a level of safeguard against a user inadvertently gripping the guide wire or the like during tamping, where in an exemplary embodiment, the tamper slides relative to the guidewire during tamping.

FIG. 12 functionally depicts the environment in which tamper 71 is utilized. More particularly, after the delivery instrument 100 is withdrawn as detailed above to expose the tamper and the other components, tamper 71 is exposed as depicted in FIG. 12A. In the exemplary embodiment depicted in FIG. 12, guide wire 20 and filament 80 extend through respective lumens 20' and 80'. (FIG. 12B depicts a cross-section of tamper 71 taken at line A-A- of FIG. 12B, where the guide wire 12 and the filament 80 have been removed for clarity.)

In an exemplary embodiment, the tamper 71 (or 72 or 73 or variations thereof) enables tamping action over/along the guide wire 20 and suture 80, running through separate lumens 20' and 80' in the double lumen tamper, until the tamper 71 contacts the lock 60. Upon contact, the user pushes down (continues to push down) on the lock 60 to compress the plug 50 in place/to lock the already compressed plug 50 in place (such as is done by way of example and not by way of limitation, as detailed in the '827 patent, the '681 patent, the '653 application, at least with respect to movement along the filament thereof), without affecting the placement of the guide wire 20. The double lumen tamper 71 enables utilitarian support of the guide wire 20, as compared to the absence of the lumen for the guide wire (or the absence of the alternate components to achieve association with the guide wire) during the deployment of the device and/or can statistically improve user experience when tamping as compared to tamping without such an association feature.

Figure 13:
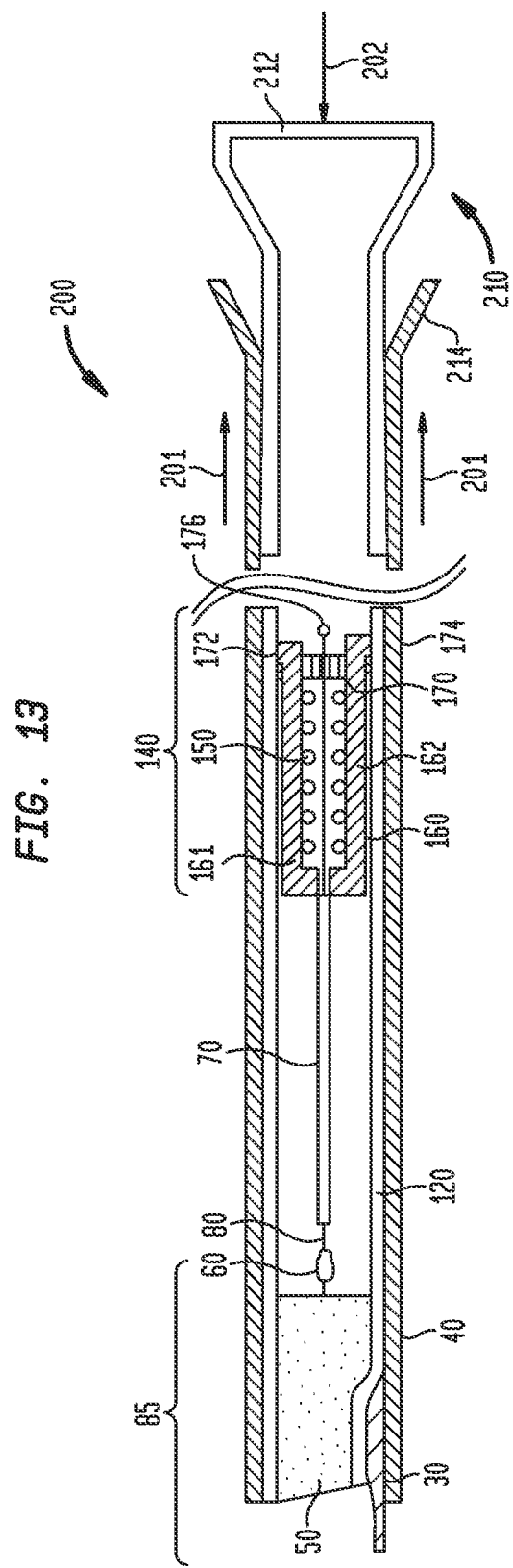
FIG. 13 depicts an alternate embodiment of a deployment instrument.

FIG. 13 functionally depicts an alternate embodiment of a delivery instrument 200. It is noted that some and/or all of the additional features (e.g., the tensioner apparatus, described below) described with respect to instrument 200 may be included in instrument 100. It is further noted that an exemplary embodiment of deployment instrument 200 includes some or all of the features of instrument 100 detailed above.

Briefly, movement of the release tube 40 relative to the delivery tube 120 is achieved by applying force to section 214 of the release tube 40 in the proximal direction of the deployment instrument 200, as indicated by arrow 201, while applying a reaction force to the delivery tube 120 at section 212 in the direction of arrow 202. Application of sufficient force thereto drives the release tube 40 towards the proximal end of the instrument 200, and moves it relative to the deployment tube 120, until section 214 abuts section 212 or until the force is reduced/eliminated. In this regard, the exemplary embodiment of FIG. 13 is such that there is a slight friction fit between the tubes 40 and 120, although in an alternate exemplary embodiment, the fit is a slip fit. Alternatively or in addition to this, additional components, such as an O ring or the like, may be interposed between the tubes to generate a modicum of friction. Any device system and/or method of moving the tubes relative to one another may be practiced in some embodiments.

In an exemplary embodiment, aside from the different mechanisms utilized to move the tubes relative to one another, the functionality of the deployment instrument 200 corresponds to that of the deployment instrument 100, as well as its use.

An exemplary embodiment includes a device, system and/or method of gauging or controlling the application of tension on filament 80 while deploying the closure device 85 described herein. Specifically, the application of high tension on filament 80 may result in the toggle pulling out.

Alternatively, insufficient tension will not compress the plug 50 onto the exterior vessel wall.

Prior to describing an exemplary embodiment of a tensioner assembly of the delivery instrument 100, some actions associated with deployment of the closure device 85 by the deployment instrument 100 will be briefly described (some of which includes redescription and/or variations of the description above) in the context of the function of the tensioner assembly.

As detailed above, movement of the deployment instrument 100 in the proximal direction causes toggle 30 to engage the artery wall. As the toggle 30 catches/engages, resistance will be felt by the user with increased movement of the deployment instrument 100 in the proximal direction.

With increased movement of the deployment instrument 100 away from the puncture, the plug 50 is deployed into the puncture tract with the toggle 30 engaging or catching the inner surface of the artery wall contiguous with the puncture. The instrument 100 is then pulled further outward. Inasmuch as the toggle 30 trapped against the interior of the artery wall, the continued retraction of the deployment instrument 100 causes the filament 80 to pull the plug 50 out of the delivery tube 120 of the deployment instrument 100 and into the puncture tract. As the deployment instrument comes out of and/or is moved further away from the puncture tract, continuous steady resistance will be felt as the tensioner assembly of the deployment instrument controls the force on the filament 80 during the retraction procedure.

Continued retraction of the instrument 100 brings the tamper 70 out of the distal end of the deployment instrument 100 (thus exposing the tamper 70).

The retraction of the deployment instrument 100 carries the plug 50 into engagement with the exterior of the artery wall immediately adjacent the puncture. Continued retraction causes the filament 80 to deform the plug 50, i.e., cause it to deform radially outward, in an exemplary embodiment, as detailed by way of example in the '827 patent, the '681 patent and/or the '653 application, the contents of which relating to such deployment/expansion/positioning of the plug incorporated by reference herein for use in embodiments associated with deployment of the closure device 85. In an embodiment, the plug 50 (which may be a collagen pad, as noted above) is forced to fold down after exiting the delivery tube 120 (in some embodiments, it begins to fold down immediately upon exiting the delivery tube 120). The existence of blood within the puncture tract can further contribute to the deformation of the plug 50, because, in some embodiments, it is collagen foam that expands and softens in the presence of blood. The retraction procedure continues to pull the deployment instrument 100 up the filament 80 until the user stops pulling. At this point the plug 50 should be located in the puncture tract contiguous with the opening in the artery, and the lock 60 (if utilized) located immediately proximally of the plug.

The plug 50 is now ready to be positioned in the tract. To achieve that end, the user compacts the plug 50 by gently tensioning the filament by, for example, pulling on the handle 110 of the delivery instrument 100 in the proximal direction with one hand. This moves loop element 81 down along the filament as a result of tension on filament. Here, toggle 30 acts in an analogous manner to a pulley as described in, for example, the '653 application, the contents of which associated with that pulley action being incorporated herein by reference for use in an exemplary embodiment utilizing such pulley action. This has the effect of tightening the loop 82. As element 81 moves down filament section to tighten loop 81, it compacts plug 50. This forces plug 50 to conform to the artery contiguous with the puncture in the artery.

Next, the tamper 71 is manually slid down the filament 80 by the user's other hand so that it enters the puncture tract and engages the proximal side of the lock 60, if present. A force is applied to tamper 71 sufficient to overcome the resistance to movement of the lock 71 relative to the filament, at least if the lock 60 corresponds to the lock of the '653 application. This causes the lock 60 to slide down filament section until it abuts element 81. An exemplary embodiment of the lock 60 is configured, when used in conjunction with filament 80, to provide a certain amount of resistance to movement along filament 80. This locks element 81 in place, as, for example, taught in the '653 application, thus preventing loop 82 from expanding. This feature causes the plug 50 to be secured in the compact position until hemostasis occurs (which happens relatively very quickly, thereby locking the closure device in place). That is, because the plug 50 is compressed between the toggle 30 and the lock 60, plug 50 is retained or locked in position within the puncture tract and cannot move away from the toggle, even before the blood clots in the plug.

In an exemplary instrument the deployment instruments detailed herein and/or variations thereof include a tensioner assembly. Such a tensioner assembly will be described in terms of deployment instrument 200, but are readily applicable to deployment instrument 100, as will now be described.

FIG. 13 depicts a cross-sectional view of deployment instrument 200, including tensioner assembly 140 in the form of a tensioner cartridge 160. Tensioner cartridge 160 configured to gauge/measure and/or to control the forces (e.g., tension in filament 80) resulting from deployment of closure device 85. The tensioner cartridge 160 provides the user with visual and/or tactile and/or auditory feedback during deployment. The construction of the tensioning cartridge includes a spring 150 located inside a retractable tube 162 that allows for the passage of filament 80 therethrough. The cartridge 160 includes a retractable member 170. In an exemplary embodiment, the retractable member 170 is fixedly attached to the filament 80, such that tension on the filament 80 imparts a force onto the retractable member 170, and thus spring 150. In an alternate embodiment, the filament 80 is attached to one or more of the coils of spring 150 (e.g., the most proximal coil/last coil), such that tension on the filament 80 imparts a force onto the spring 150. In an alternate embodiment, the retractable member 170 may include a soft tensioning member 172 through which the filament 80 extends. The tensioner assembly 140 one or more utilitarian functions. For example, it controls the force applied to the filament 80 (and thus the tension) by holding the filament taut during pull back of the instrument 200 (or 100) while providing a system for allowing the user to guard against the application of too much force. By utilizing the tensioner assembly 140 as detailed below, a user may apply adequate filament tension for compressing the plug 50 and/or during tamping the lock 60 or other component.

The tensioner assembly may also provide tactile and/or visual and/or auditory indication for the user to stop pulling back and/or to stop applying additional (increasing) force to the deployment instrument in the distal direction when the end of suture length has been reached through change in color, shape, etc., visible on the instrument. In an exemplary embodiment, this can prevent or otherwise enable safeguarding against excessive force being applied to the toggle, preventing the toggle from pulling out of the blood vessel.

During use, application of a force onto deployment instrument 100 that results in a first tension on the filament is sufficient to withdraw the cartridge 160 out of the delivery tube 120, exposing the cartridge 160 such that the user may handle the cartridge 160 with his or her hand. In particular, cartridge 160 is carried within delivery tube 120 such that there is a slight friction fit between the two components. This may be achieved, by way of example, via, elastomeric O-ring 174, as may be seen. Application of the first tension (by applying a sufficient withdrawal force on the instrument 200 in the proximal direction) is sufficient to overcome the friction forces and pull the cartridge 160 out of the tube 120. Alternatively or in addition to this, a snap fit is utilized to retain the cartridge, and a sufficient force applied to the instrument resulting in sufficient tension on the filament is sufficient to release the snap fit. In yet another alternative embodiment, a positive retention mechanism, such as an actuating cylinder or box beam, etc., that extends into the tube 120, and thus blocks the cartridge 160 until it is moved out of the tube 120, or at least from in front of the cartridge 160, may be utilized to retain and then release the cartridge. Any device, system and/or method that can provide the modicum of friction between the cartridge 160 and the delivery tube 120 and/or that provides the modicum of securement so as to releasably retain the cartridge 160 in the delivery tube 120 until it should be exposed can be utilized in some embodiments. In this regard, it is noted that the first tension may vary between embodiments. By way of example, the tension associated with overcoming the friction fit utilizing, for example, the O-ring, may be different from that associated with overcoming the snap-fit. Moreover, the tension may be variable or generally constant. For example, the tension during withdrawal of the cartridge 160 from the delivery tube 120 will be generally constant during the withdrawal process with respect to the friction fit utilizing the O-ring, whereas the tension may vary during withdrawal with respect to the snap-fit or the like. Embodiments where the tension is relatively constant, or at least moderately increases within a range that does not result in damage to the artery wall and/or dislodgement of the toggle, can have utility in that this results in a tension that generally maintains the toggle in place against the puncture on the interior of the artery.

Figure 14:
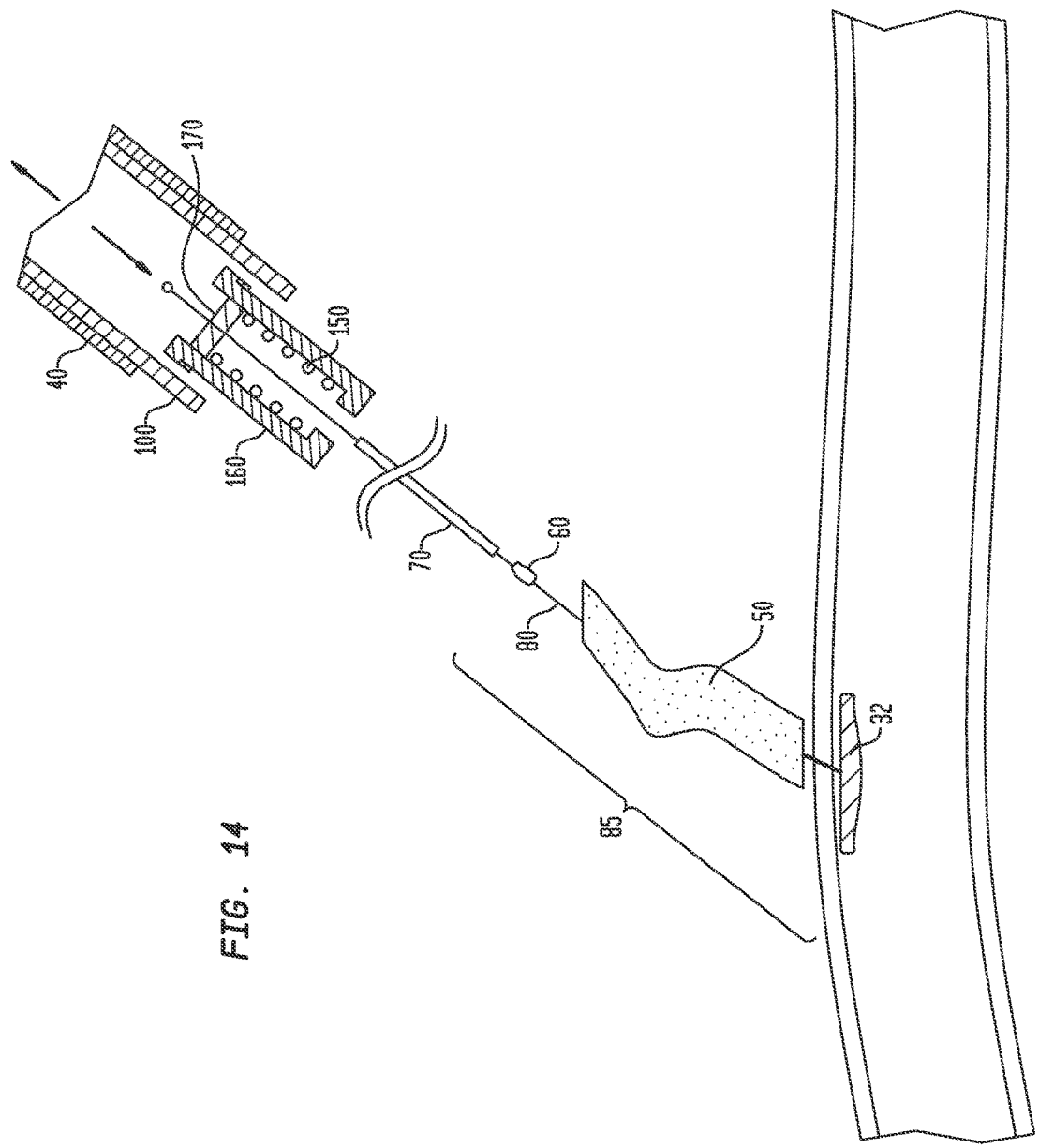
FIG. 14 depicts use of the embodiment of FIG. 13.

With respect to the embodiment of FIG. 13, where the O-ring results in a friction fit between the tube 120 and the cartridge 160, application of the first tension results in the ejectment/exposure of the cartridge 160. This is schematically represented by way of example in FIG. 14. Upon sufficient exposure of the cartridge 160, the user grips the cartridge 160 with a free hand and gradually or abruptly begins to apply force to the cartridge in the proximal direction at a level that is in equilibrium, in an exemplary embodiment, to that applied to the instrument 200, until the cartridge 160 is completely free of the delivery tube 120, at which point the tension in the filament 80 is a result of force applied to the cartridge 160 in the proximal direction.

Figure 15:
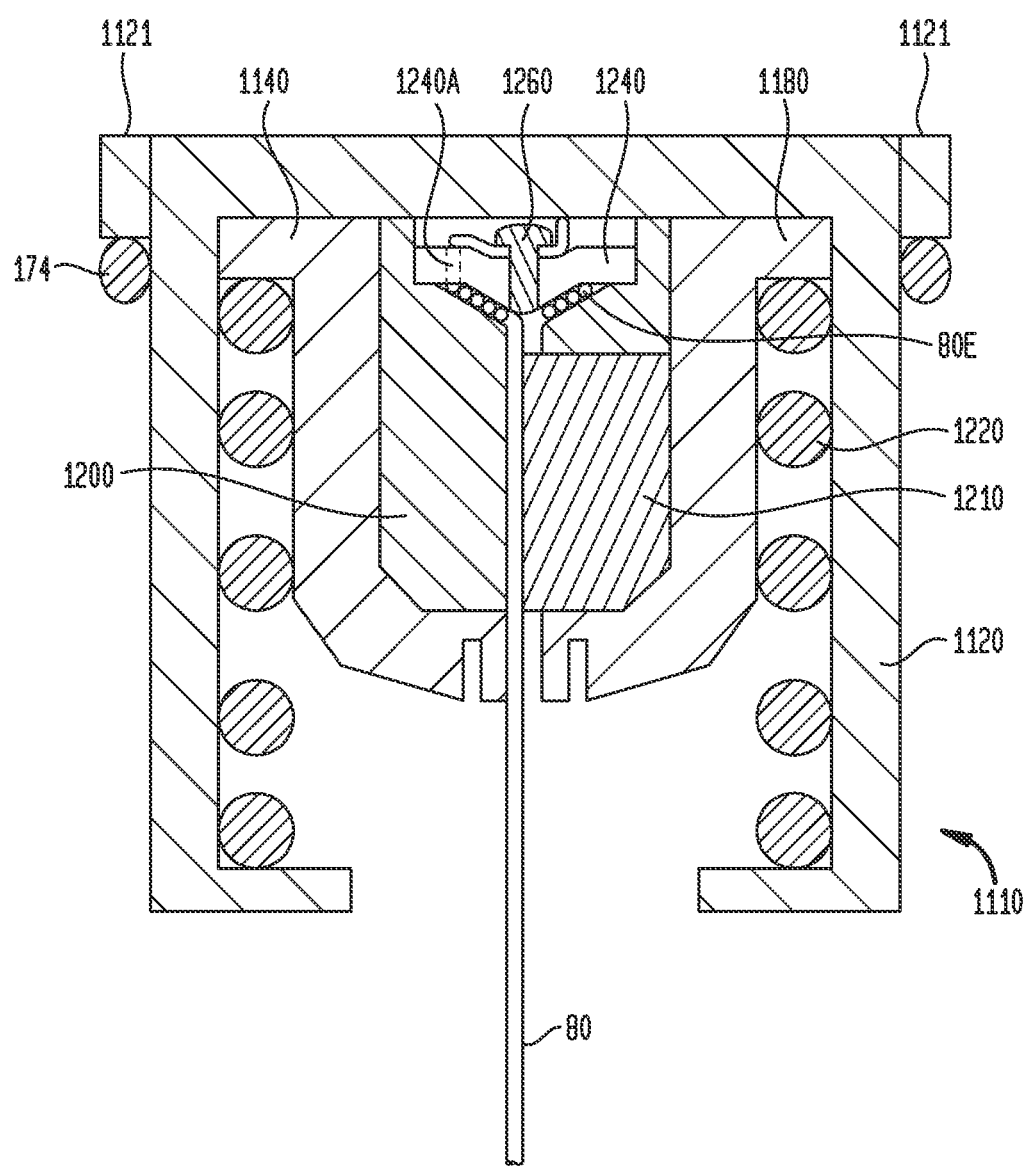
FIGS. 15-18 depict features of an exemplary tensioner according to an embodiment.

An exemplary embodiment of the present invention includes a deployment instrument 100 including an exemplary tensioner assembly 1110 as may be seen conceptually in FIG. 15. In an exemplary embodiment, the tensioner assembly 1110 conceptually corresponds to the cartridge 160 detailed above, although as will be detailed below, in an exemplary embodiment of the cartridge 160, there are different features between the two.

A portion of the procedure involving deployment of the closure device 80 in a recipient using the exemplary tensioner assembly 1110 of FIG. 15 will now be described. As may be seen in FIGS. 15 and 16, the tensioner assembly 1110 includes a frame 1120 in which a hub assembly 1140 is slidably retained. Frame 1120 includes protrusions 1121 that interact with O-ring 174. In this regard, frame 1120 corresponds to element 161 of FIG. 13. The frame 1120 serves as a handle that the user may grasp during application of the closure device 85 to the recipient. In some embodiments, the handle is provided with knurling or tread grips or the like to facilitate grasping by the user. The hub assembly 1140 includes a hub 1180 and a tensioner insert 1200 (and silicone tension block 1210, which provides friction to the filament as it uncoils). The hub assembly is spring loaded by spring 1220 (which corresponds to spring 150 of the device of FIG. 13) in the proximal direction of the deployment instrument 200. That is, with respect to FIG. 15, the spring 1220 forces the hub assembly 1140 upward, relative to the frame 1120. Another way of describing this is that the spring 1220 forces the frame 1120 downward, relative to the hub assembly 1140.

It is noted that alternate embodiments include structure that is different from that detailed herein. Indeed, a visual comparison between the embodiment of FIG. 13 and that of FIG. 15 reveals that there are differences. It is thus again noted that the structure detailed herein is exemplary and conceptual, and can and/or will vary in implementation. In this regard, while the embodiment of FIG. 15 depicts a hub 1140 that extends into the interior of spring 1220, the embodiment of FIG. 13. Hub 1140 corresponds to retractable member 170 of FIG. 13. However, retractable member 170 does not so extend into the spring 150, as may be seen.

In an exemplary embodiment, the spring 1220 permits the tension on filament 80 to be controlled/ensures that sufficient tensioning and not too much tensioning is applied to the filament during deployment of the closure device 85, as will now be detailed.

Referring to FIG. 15, the tensioner assembly 1110 includes a filament recess between the tensioner insert 1200 and a filament cap 1240 in which filament 85 is wound in a coil section 80E, from which the filament 80 travels to the closure device 85. The end of the filament 80E is threaded through a hole 1240A in the filament cap 1240 and is trapped between the filament cap 1240 and a filament lock 1260 to hold the end of the filament 80 in place. Filament lock 1260 may be held to filament cap 1240 via a screw fit or a snap fit or through the use of an adhesive or a weld, etc. That said, in an alternate embodiment, the filament 80 extends completely from one side of the hub 1140 (or the retractable member 170) to the other side thereof, and further proximally out of the frame 1120 (or element 161).

As may be seen in FIG. 15, a friction block 1210 is located in a cut-out section of the tensioner insert 1200. In an exemplary embodiment, the friction block 1210 is a silicon block that is dimensioned such that when inserted in the hub 1180 along with tensioner insert 1200, a compressive force on filament 80 is applied by the friction block 1210 and the hub 1140. In some exemplary embodiments, as will be described in greater detail below, as the filament 80 (filament from section 80E) is drawn from the spool of the tensioner assembly 1110, the user feels a relatively constant resistance and/or a relatively consistent resistance as compared to other deployment instruments 100 (i.e., the resistance felt with one deployment instrument 100 used during a given procedure will be about the same as that felt during a prior procedure with another deployment instrument 100). That is, the friction block 1210 in combination with the tensioner insert 1200 and hub 1140 function to control the force required to at least initially withdraw the filament 80 from the spool.

In an exemplary embodiment, friction block 1210 corresponds to soft tensioning member 172 detailed above with respect to FIG. 13. As has been noted above, the specific structure of various embodiments can vary, while utilizing the principles detailed herein.

Figure 16:
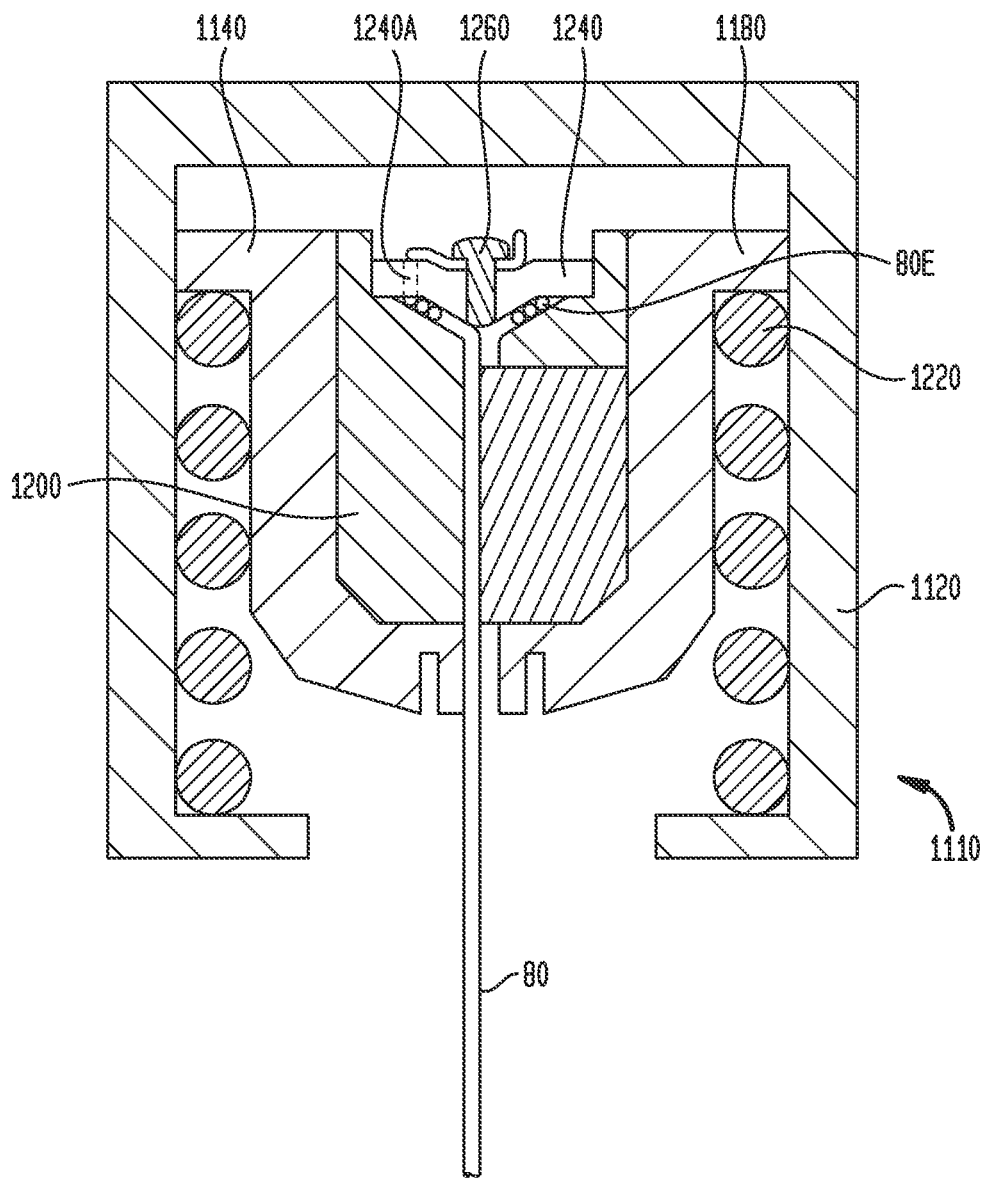
Figure 17:
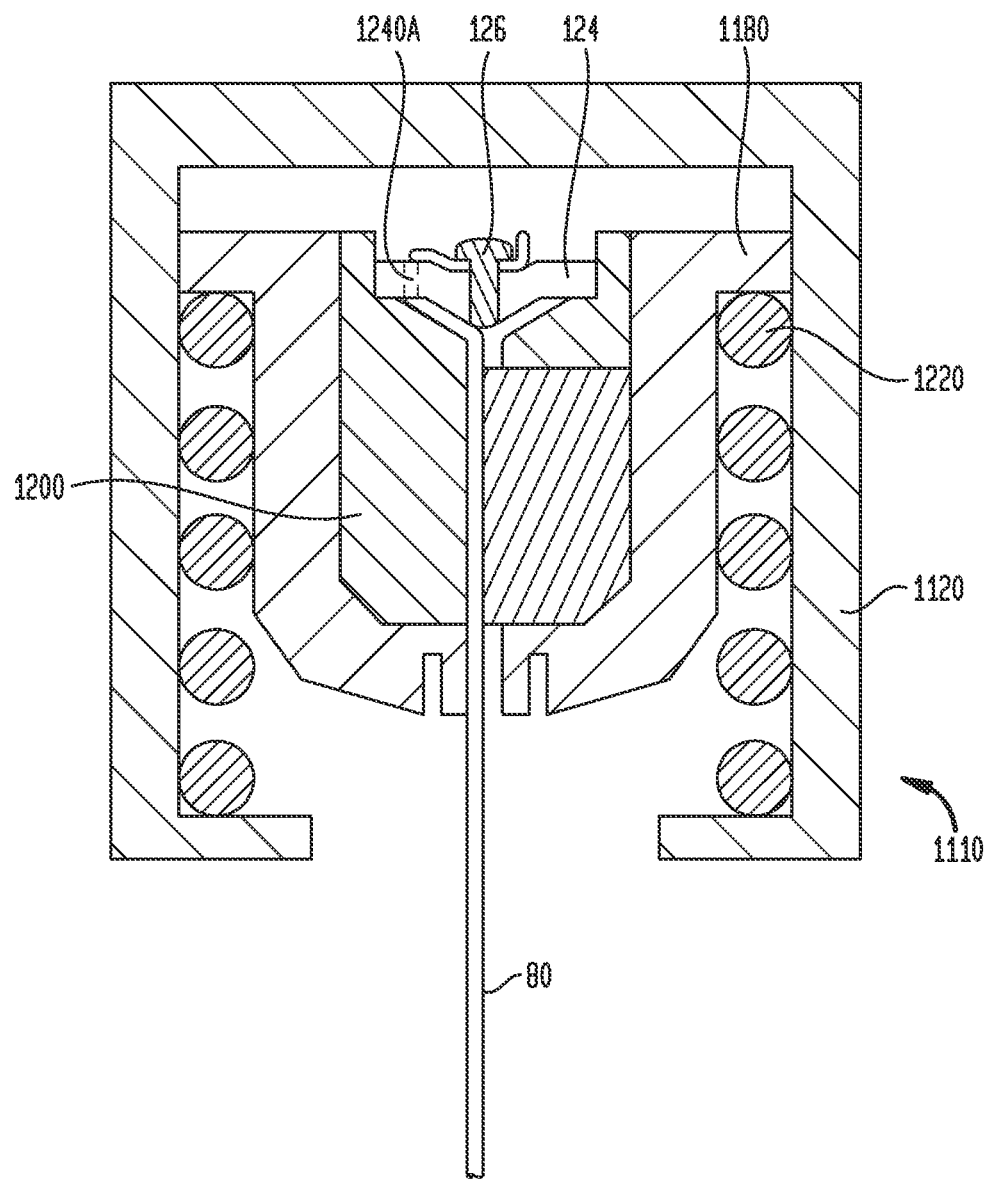

As noted above, a force applied to deployment instrument 200 sufficient to result in a first tension in the filament can result in the cartridge 160 (or tensioner assembly 1110) being exposed (withdrawn/released from inside delivery tube 120). As noted above, inasmuch as the toggle 30 is trapped (anchored) against the interior of the artery wall, the continued retraction of the deployment instrument 200 causes the filament 80 to pull the plug 50 out of the deployment tube 120 of the deployment instrument 200. Also, once the toggle 30 catches on the wall of the artery, the filament 80 (filament from section 80E or other location where the filament is stored) will be drawn from the spool of the tensioner assembly 1110. Some resistance will be felt, at least in embodiments utilizing the friction block 1210 (or its corresponding structure 172) described above (as opposed to other embodiments where no drag force is applied to the filament as a result of compression of the filament by the friction block, such as in the case where no friction block 1210/structure 172 is used and a bore or other space of the tension insert 1200 through which the filament 80 passes is oversized relative to the filament 80). This resistance may require the user to apply about ¾ths of a pound of force to the deployment instrument 200 to pull the filament 80 out of/through hub 1180/structure 170. The user continues to pull the deployment instrument 200 away from the recipient with a force sufficient to overcome the friction resulting from the compressive force applied to the filament 80 by the friction block 1210. At a given distance of the deployment instrument 200 from the recipient/from the puncture, the filament 80 will be completely unwound from the spool (or otherwise withdrawn through structure 172 until stop 176 strikes structure 172 in the case of cartridge 160). FIG. 16 depicts the tensioner assembly 1110 in the state where the filament 80 is about ½ way unwound from the spool and FIG. 17 depicts the tensioner assembly 1110 in the state where all of the filament 80 has been unwound from the spool. The tension on filament 80 is high enough to unwind the filament from the spool, and potentially compresses spring 1220 by a corresponding amount.

At this point, with increasing force applied to the deployment instrument 200, the tension in filament 80 reaches a high enough value (the first amount detailed above) to overcome the friction forces between the O-ring and delivery tube 120, and thus the cartridge 160 (or tensioner assembly 1110) becomes exposed exposed (withdrawn/released from inside delivery tube 120).

At this point, the user grips the cartridge 160 or frame 1120, and continues to withdraw the cartridge 160 or frame 1120 away from the recipient with a steady or increasing force. When the tensioner assembly 140 1110 is located a first linear distance from the vessel wall, because the end of the filament 80 (or other part of the filament 80) is trapped between filament cap 1240 and the filament lock 1260 (or element 176 abuts structure 172), continued pulling of the tensioner assembly away from the recipient (past the first distance), when the user holds the frame 1120 (or element 162) causes the filament 80 to become more tensioned because the "unwinding" of the filament 80 from the spool has stopped (there is no more filament from section 80E to be unwound) and the end of the filament 80 is held in place as it is attached to the tensioner assembly. Accordingly, this increase in tension as the user moves the deployment tensioner assembly from the first distance from the vessel wall causes frame 1120 (or element 162) to move relative to hub assembly 1140 and thus causes spring 1220 (or spring 150) to compress or further compress. The force compressing the spring is substantially equal to the tension in the filament 80. As the tension of the filament 80 progressively increases as the user continues to pull the tensioner assembly 200 away from the recipient (via pulling on the frame 1120 or element 162), the spring 1220 continues to be compressed, thus resulting in a gradual increase in the tension of the filament 80 as the tensioner assembly is continued to be pulled away from the recipient. This as compared to the relatively sudden increase in tension that would exist if the hub assembly 1140 were instead rigidly fixed to the tensioner assembly 1110 and/or the spring 1220 were not present (or if structure 170 were instead rigidly fixed to the tensioner assembly 140 and/or the spring 150 were not present. In this regard, the spring 1220/spring 150 provides a dampening or cushioning effect with respect to the force applied to the inner wall of the blood vessel or other body passageway which reacts against the toggle 30 at the time that the filament 80 is fully unwound from the spool. Thus, there should be no sudden increase in the force/pressure on the wall at the location of the toggle 30. Instead, there should be a gradual increase in the force/pressure on the wall at the location of the toggle 30. In an exemplary embodiment, the hub assembly 1140 may travel about eight (8) millimeters upon the application of about two (2) pounds of tension force in the filament 80 before bottoming out (i.e., the hub assembly 1140 cannot move further downward/frame 1120 cannot move further to the upward with respect to FIG. 15). Thus, an embodiment provides a mechanically induced increasing tension force applied to the filament that increases with increasing distance of the tensioner assembly away from the puncture at a rate of less than about 1.5 pounds per 4 mm of increased distance of the deployment instrument away from the puncture. Accordingly, in an exemplary embodiment, pulling the tensioner assembly away from the puncture while the filament is connected thereto results in an initial contact of the anchor to the wall of the body passageway followed by a gradual increase in pressure applied to the wall by the anchor while tension in the filament is less than about two (2) pounds. Thus, via a mechanical device of the deployment instrument 200, a sudden increase in pressure applied to the wall of a body passageway by the toggle 30 is avoided.

Figure 18:
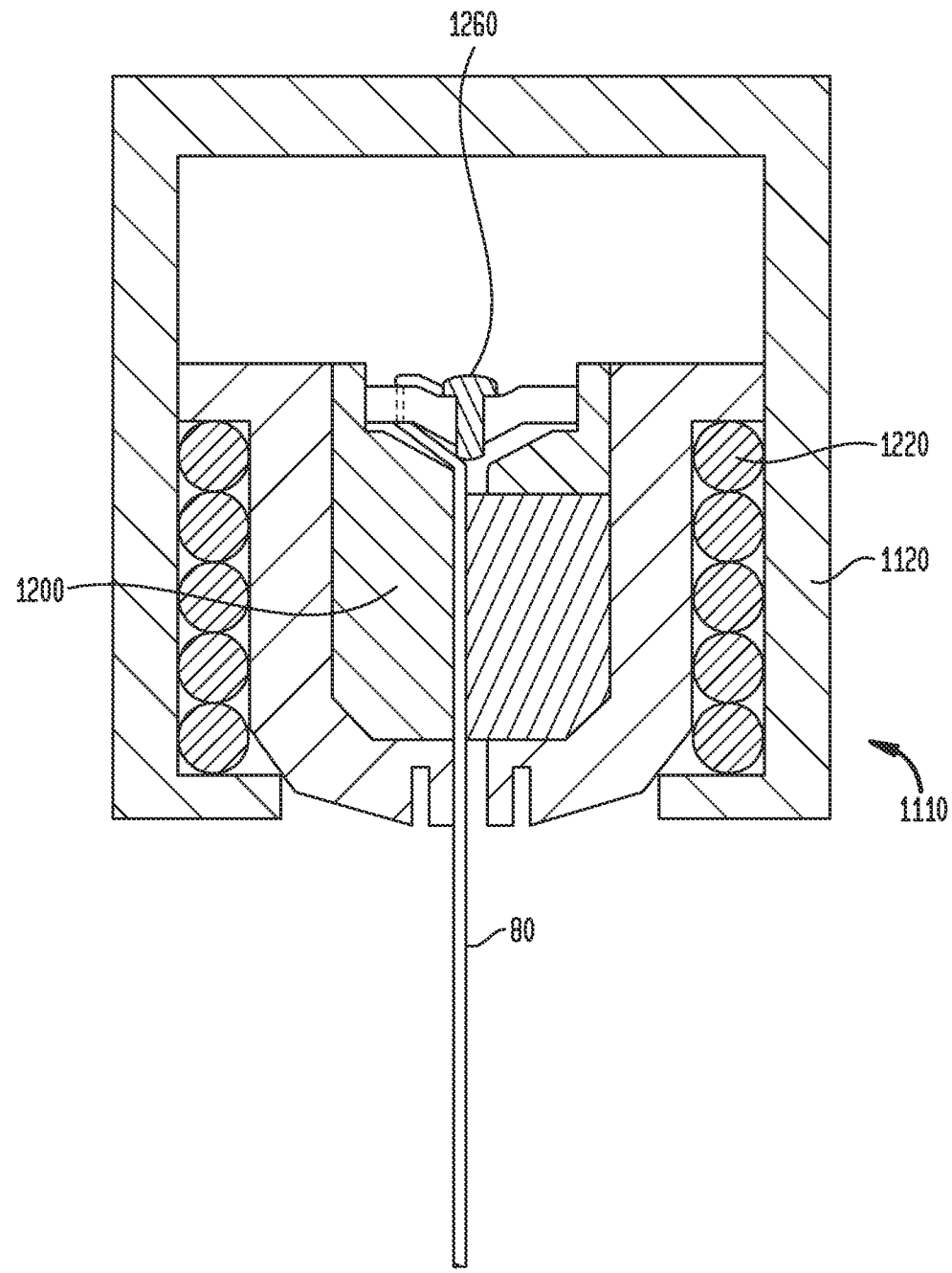

FIG. 18 depicts spring 1120 fully compressed upon the application of two (2) pounds of tension force in the filament 80 by the user while filament 80 is connected to toggle 30 (which, as noted above, is lodged in the artery). By bottoming out the hub assembly 1140, and not pulling on the tensioner assembly too much more after that, the user can ensure that he or she has applied about two (2) pounds of tension force on the filament 80, and not too much more. This ensures that sufficient tension has been applied to the filament to properly deploy the closure device 85, and not too much more. Also, the spring 1220/spring 150 at least partially reduces what otherwise might be a spike in the force applied to the wall of the artery upon the filament 80 becoming completely unwound from the spool and becoming unslackened due to movement of the tensioner assembly away from the recipient.

In an exemplary embodiment, the user feels/senses the gradual increase in tension as the spring 1220/spring 150 is compressed (as compared to the relatively static tension resulting from friction block 1210/element 174), and thus is provided an indication that the tensioner assembly will soon reach the mechanical limits of its withdrawal away from the recipient, after which any further withdrawal will be due to the plastic and/or elastic nature of the filament and the recipient. In some embodiments, the spring 1220 is a linearly compressible spring, and thus the gradual increase in tension as the spring 1220 is compressed is linear. Non-linear compressible springs may also be used, in which case the gradual progressive increase in tension is not linear. In an exemplary scenario of use, the user continues pulling the tensioner assembly away from the recipient until the spring 1220/spring 150 bottoms out, and then halts further movement of the tensioner assembly away from the recipient. Alternatively, the user can continue to pull the tensioner assembly away from the recipient, thereby further increasing the tension in the filament 80. Even with respect to this latter scenario, the indication afforded to the user by the spring 1220/spring 150 provides the user with an opportunity to adjust the deployment procedure to avoid injury to the recipient and/or damage to the closure device, etc.

It is noted that as the tensioner assembly 100 is pulled away from the recipient, and by the time that the spring 1220 has bottomed out, the pulley arrangement of the filament 80 connecting toggle 30 and the plug 50 causes the plug 50 to be moved into engagement with the exterior of the artery wall contiguous with the puncture. The tension in the filament 80 resulting from pulling the tensioner assembly away from the recipient causes the filament 80 to somewhat deform the plug, i.e., cause it to deform radially outward and, in some embodiments, twist. Because the spring 1220/spring 150 permits the tension on filament 80 to be controlled/ensures that sufficient tensioning and not too much tensioning is applied to the filament during deployment of the closure device 20, the user is provided with some reassurance that the proper amount of tensioning has been applied to the filament 80 to deform the plug and properly deploy the closure device 20.

It is noted that in an exemplary embodiment, plug 50 can be withdrawn from tube 120 without contacting the sheath 10 and/or at least without contacting the interior of the sheath 10. This may, in some embodiments, eliminate the possibility that the plug 30 might become stuck in the sheath 10—during the deployment procedure as it expands once leaving the tube 120.

It is noted that an exemplary embodiment includes an indicator that provides an indication to the user that the hub assembly 1140 has bottomed out within the frame 1120 (or corresponding structure). In an exemplary embodiment, the indicator corresponds to, at least conceptually and/or functionally, to the indicator taught in the '653 application, the contents of which pertaining to the indicator being incorporated herein by reference in their entirety for use in an embodiment.

Figure 19:
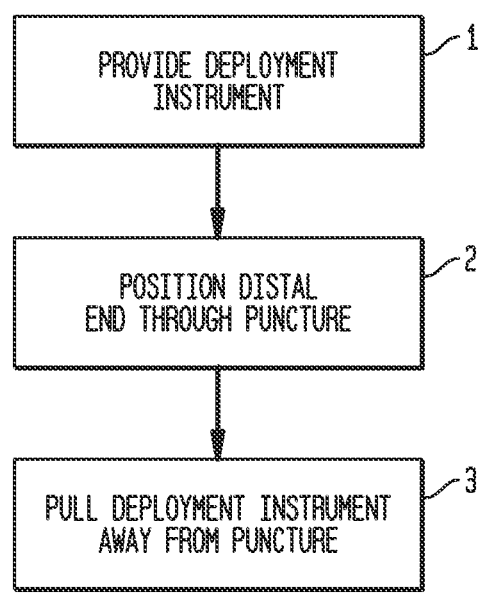
FIG. 19 is a flowchart of an exemplary method.

Accordingly, in an exemplary embodiment, referring to the flowchart of FIG. 19, there is a method of sealing a percutaneous puncture in a wall of a body passageway, comprising, at step 1, providing a deployment instrument 100 including a tensioner assembly 1110/140 and carrying a closure device 80, the closure device 80 including a toggle, a plug 50 and a contiguous elongate filament 80 configured to draw the plug 50 towards the toggle 30 upon the application of tension to the filament 80 in a direction away from the toggle 30. At step 2, the distal end of the deployment instrument 100 is positioned through the puncture into the body passageway such that the toggle 30 is located in the body passageway. At step 3 the deployment instrument 100 is pulled away from the puncture while the filament 80 is connected to the deployment instrument. This results in the application of a mechanically induced increasing tension force to the filament 80 that increases with increasing distance of the deployment instrument 100 away from the puncture, thereby drawing the toggle 30 and the plug 50 towards each other and into engagement with the wall of the body passageway at respectively opposite sides of the wall. In an exemplary embodiment, the mechanically induced increasing tension force is a result of spring, as detailed above.

FIG. 20A depicts an embodiment that utilizes two plugs 50 and 50', each located on a portion of loop 82, with a single toggle 30. An exemplary embodiment of such a configuration provides utility in that two plugs may better seal a relatively large puncture. In this regard, some punctures will extend a relatively great distance about the artery wall in a direction normal to the longitudinal axis thereof. For example, the puncture may extend over an arc that extends about 20, 25, 30, 35, 40, 45, 50, 55, 60, 65, 70, 80, 90, 100, 110, 120, 130, 140, 150, 160 170 and/or about 180 degrees or more and/or angles in between these in one degree increments. A single plug may bunch at the apex of the puncture, thus leaving portions of the large puncture exposed on either side of the plug. The use of two plugs covers more area, and thus can cover more of the puncture. By way of example, a single plug may cover a puncture extending over an arc of 10 or 20 degrees, whereas two plugs may cover a puncture extending over an arc of about 25, or or 35 or 40 or more degrees. Along these lines, the use of two holes 31 for the filament spread relatively far apart can space the plugs over the full area of the puncture.

It is noted that the washer 500 detailed above can be used to spread out the filament 80 so as to avoid or otherwise reduce the tendency of the plug to bunch at the apex of the puncture in a manner the same as or similar to the manner by which the more widely spaced holes 31 prevents or otherwise reduces the bunching tendency.

FIG. 20B depicts a cross-sectional view of a closure device according to the embodiment of FIG. 20A after delivery.

As can be seen in FIG. 20A, the exemplary embodiment utilizing two plugs 50 and 50' can include two tampers 70 and 70' to tamp locks 60 and 60'. Use of these additional components may correspond to the teachings detailed above, albeit sequentially (tamping lock 60 first with tamper 70, and then tamping lock 60' with tamper 70').

Still referring to FIG. 20A, an exemplary embodiment includes an alternate embodiment of a tensioner apparatus. Specifically, FIG. 20A depicts a tensioning apparatus 400. In an exemplary embodiment, tensioning apparatus 400 corresponds to a spring that is biased such that the ends 401 and 402 of the spring are separated as shown in FIG. 20A. Specifically, ends 401 and 402 can be wrapped about filament 80 as conceptually shown, or otherwise may include devices at the ends that permits the filament 80 to slide relative therethrough while holding the filament 80. Upon tensioning the filament 80 as detailed herein, the two portions of filament 80 between element 81 and the toggle 30 will tend to move towards each other. The tensioning apparatus 400 will resist this movement owing to the spring bias just mentioned. The more tension applied to the filament 80, the greater the tendency for these portions of filament 80 to move towards each other, thus compressing the spring/moving the ends 401 and 402 closer together. Accordingly, a user can view the degree of closure of the spring/movement of ends 401 and 402 closer to one another, and thereby determine or otherwise estimate/gauge how much tension is being applied. In an exemplary embodiment, a gauge may be included with tensioning apparatus 400 that permits the user to read the tension on the filament 80 owing to the location of the ends 401 and 402 (or the arms that support the ends) relative to the gauge. In yet an alternate embodiment, a spacer element may be present between the ends (or arms) that functionally permits the spring to bottom out in a manner akin to that detailed above with respect to spring 1120/150, and thus having the functionality/utilitarian value of that configuration.

Figure 21:
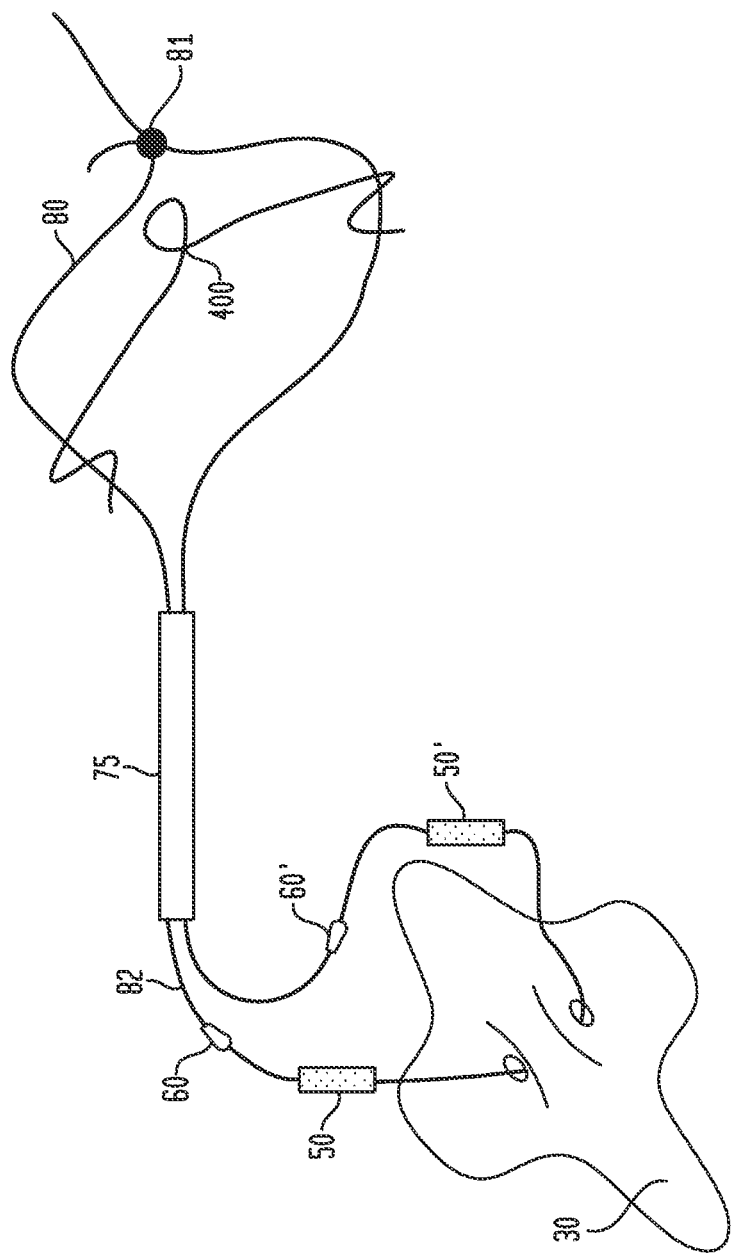
FIG. 21 depicts an embodiment utilizing a dual-lumen tamper.

FIG. 21 depicts a variation of the embodiment of FIG. 20A, where instead of two separate tampers, a single tamper 75 is present that includes two lumens through which the two sides of the filament that forms loop 82 extends the same embodiment with a double lumen tamper used to include the double sutures.

Figure 22:
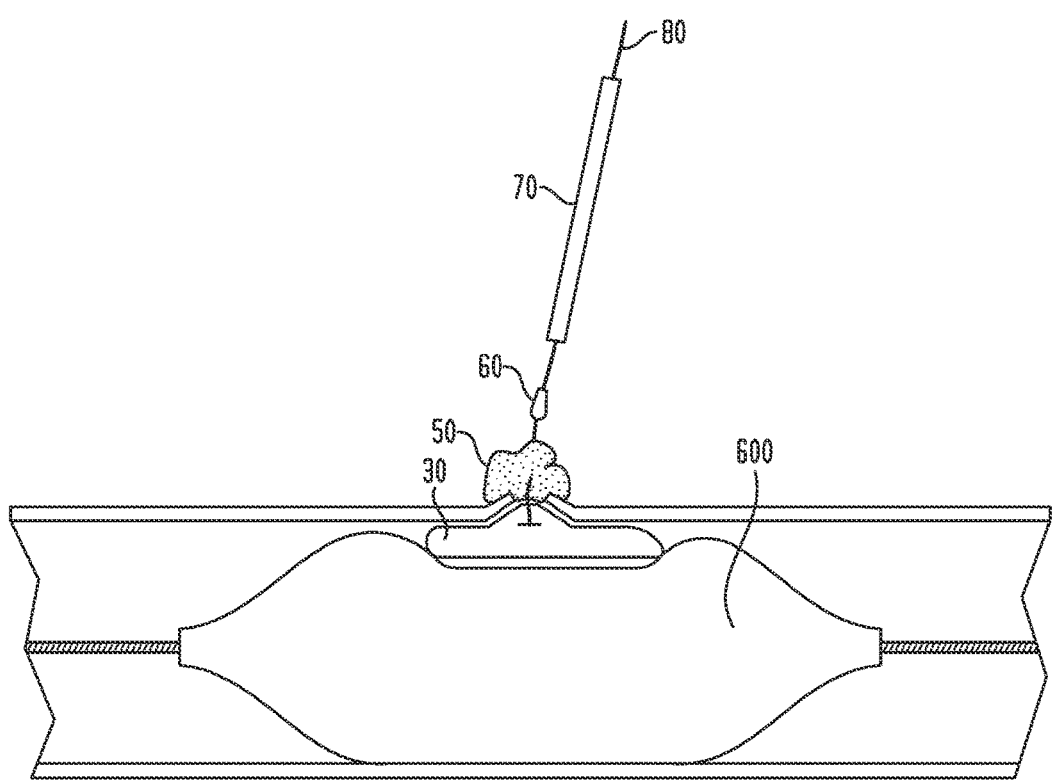

In another embodiment, the occlusion balloon 600 is moved distally from the occlusive position to the puncture site, whereby the occlusive balloon 600 is utilized to assist with positioning the toggle 30 and/or the plug 50 and sealing the puncture. Such is depicted by way of example and not by way of limitation in FIG. 22. Exemplary actions associated with such a procedure can include first position toggle intra-arterially as detailed herein and/or variations thereof in general, and, in particular, with respect to FIG. 6. Once the toggle 30 is positioned proximate the puncture, the occlusion balloon is deflated. Next, the occlusion balloon 600 is moved from its occlusion position to a location corresponding to a longitudinally proximate position of the puncture. After this, the occlusion balloon 600 is re-inflated to occluding pressure and/or another pressure that will enable the teachings detailed herein and/or variations thereof to be practiced. This can push the toggle 30 against the interior of the artery as shown in FIG. 22. The user can then double check the final position of the toggle 30 (using fluoroscopy or the like) and/or make adjustments to the tension or positioning of the plug 50 before deflating the balloon 600. (Before deflating the balloon, the closure device 20 may be secured in place according to the teachings detailed herein and/or variations thereof, or such may be done after deflating the balloon.) FIG. 22 depicts an action of this method, where it can be seen how the balloon 600 covers the toggle 30 and puncture site. This action associated with FIG. 22 can allow for full compaction of the plug 50 without any risk of or otherwise significantly statistically reducing the chances of reinsertion of the plug within the artery as compared to that which would exist without use of the balloon 600.

An exemplary embodiment includes the use of a double balloon catheter, where the proximal balloon serves to occlude flow, while the second, and moveable (slideable) balloon is utilized to assist with toggle and collagen placement as above. FIG. 23 depicts an action associated with a method of such an embodiment, where balloon 600' is the occluding balloon and balloon 600 is the balloon that is used to position the toggle 30.

FIGS. 24A, 24B and 24C depict an alternate embodiment of a toggle. Specifically, these FIGS. depict a toggle 135 having hinged wings or flaps 136 and 137 via hinge features 136A and 137A. Hinge features may be barrel hinges or may be areas of relative weakness that enables the wings to hingedly move (or flap). Toggle 135 has a width W1 that is larger than the maximum internal diameter of the sheath 10 on a plane normal to the longitudinal axis thereof. In this regard, wings 136 and 137 of the toggle 135 (e.g., portions outboard of the dashed lines seen in FIGS. 24A-24C), are located outboard of the inboard portion of the toggle represented by main body 138. In an exemplary embodiment, the outboard portions are flexibly connected or otherwise hingedly connected to the rest of the toggle 135.

In an exemplary embodiment, the toggle 135 is configured to elastically deform at the areas of the hinges and/or thereabouts. By way of example, width W1 of FIG. 24A is a first value, corresponding to any of the values detailed above with respect to the tip to tip distance and/or variations thereof, and this value corresponds to the value when the toggle 135 is in the relaxed state. Upon the application of a force to the wings, the value of W1 increases, by about 4 mm (about 2 mm for each wing), although in alternate embodiments, the value W1 increases by about 0.5 mm, 0.75, 1, 1.25, 1.5, 1.75, 2, 2.25, 2.5, 2.75, 3, 3.25, 3.5, 3.75, 4, 4.25, 2.4, 4.75, 5, 5.25, 5.5, 5.75, 6, 6.25, 6.5, 6.75 and/or any value in between these values and/or any ranges encompassing some or all of these values (including ranges being bounded by the in between values).

This increase in value of W1, or at least a portion thereof, elastically deforms the toggle 135, such that it retains the new value of W1 or something close to that or something in between, depending on the elastic properties that come into play associated with the plastic properties.

Figure 24D:
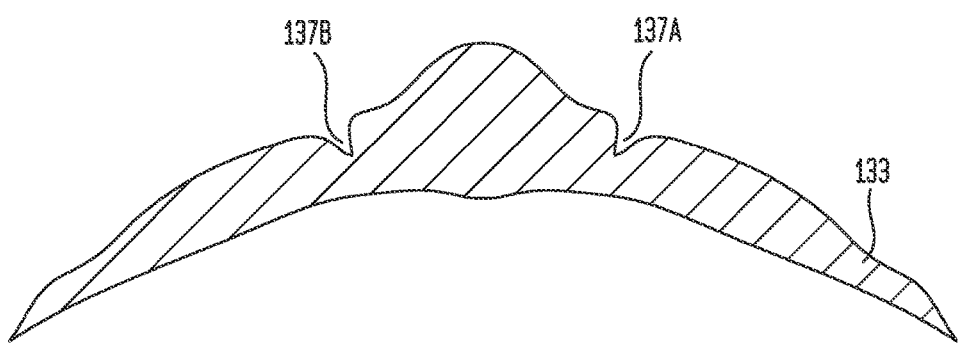

FIG. 24D depicts a cross-sectional view of toggle 135 through section A-A of FIG. 24C. As can be seen, hinge features 136A and 137A are notched sections in the top surface of the toggle 135. In an alternate embodiment, the notches are located in the bottom surface. In an alternative embodiment, the notches are located both above and below. In an exemplary embodiment, hinge feature 136A is a notch located on the top and hinge feature 137A is a notch located on the bottom, or visa-versa. (The holes 31 are not depicted in the cross-sectional view of FIG. 24D.)

Any device, system and/or method that enables the folding functions detailed herein and/or variations thereof with respect to the wings may be utilized in some embodiments.

In an exemplary embodiment, the toggle 135 is such that the resistance to flexure of the toggle along lines 136A and/or 137A is substantially and/or effectively less than resistance to flexure of the toggle at locations generally proximately inboard and outboard thereof. In an exemplary embodiment, the toggle 135 is such that the elastic modulus of the toggle along lines 136A and/or 137A is substantially and/or effectively less than that of the toggle at locations generally proximately inboard and outboard thereof.

As noted above, the wings may expand upon the application of sufficient force thereto. In this regard, an exemplary embodiment of the toggle 135 is utilized in conjunction with a balloon 600 in a manner similar to and/or the same as that detailed above with respect to FIG. 22. More particularly, FIGS. 25A, 25B and 25C schematically illustrate a sequence according to an exemplary embodiment combining the above teachings. FIG. 25A depicts the toggle 135 positioned at the puncture, with the wings 136 and 137 drooping downward prior to applying tension to the filament beyond about that which is used to hold the toggle 135 against the puncture (e.g., prior to cinching the loop 80, etc.) Balloon 600 is depicted in a deflated or semi-deflated state, and is located longitudinally proximally to the puncture (and toggle 135).

FIG. 25B depicts inflation of the balloon 600. As the balloon expands outward, wings 136 and 137 are forced outward towards the wall of the artery 1026. FIG. 25C depicts the balloon 600 inflated to at least about its maximum inflation dimensions. As can be seen, the wings 136 and 137 are trapped against the wall of the artery between the wall and the balloon 600. At this time, additional tension is applied to the filament 80 to move the plug 50 (not shown) towards the toggle 135, etc. More particularly, FIG. 25C depicts how balloon 600 (single or double embodiment) may be used to orient the wings 136 and 137 of the toggle 135 to assist with internal closure.

Exemplary embodiments of FIGS. 24A-D and/or 25A-C can be used to substantially and/or effectively statistically reduce the chances of the toggle 135 dislodging and/or passing through the puncture and into the tract relative to the other embodiments detailed herein and/or variations thereof. This statistical phenomenon may be, for example, because the additional area of the toggle 135 owing to the wings because the wings can be folded for insertion into the sheath 10. This as compared to a toggle without folding wings, where the maximum size of the toggle is limited by the internal diameter of the sheath 10.

Exemplary embodiments of FIGS. 24A-D and/or 25A-C can be used in applications where the puncture extends over a larger arcuate distance as compared to toggles having smaller widths. For example, the puncture may extend over an arc that extends about 20, 25, 30, 35, 40, 45, 50, 55, 60, 65, 70, 80, 90, 100, 110, 120, 130, 140, 150, 160 170 and/or about 180 degrees or more and/or angles in between these in one degree increments. The embodiments of FIGS. 24A-C and/or 25A-C can substantially and/or effectively statistically reduce the chances of the toggle 135 dislodging and/or passing through such punctures puncture and into the tract relative to the other embodiments detailed herein and/or variations thereof.

Figure 26B:
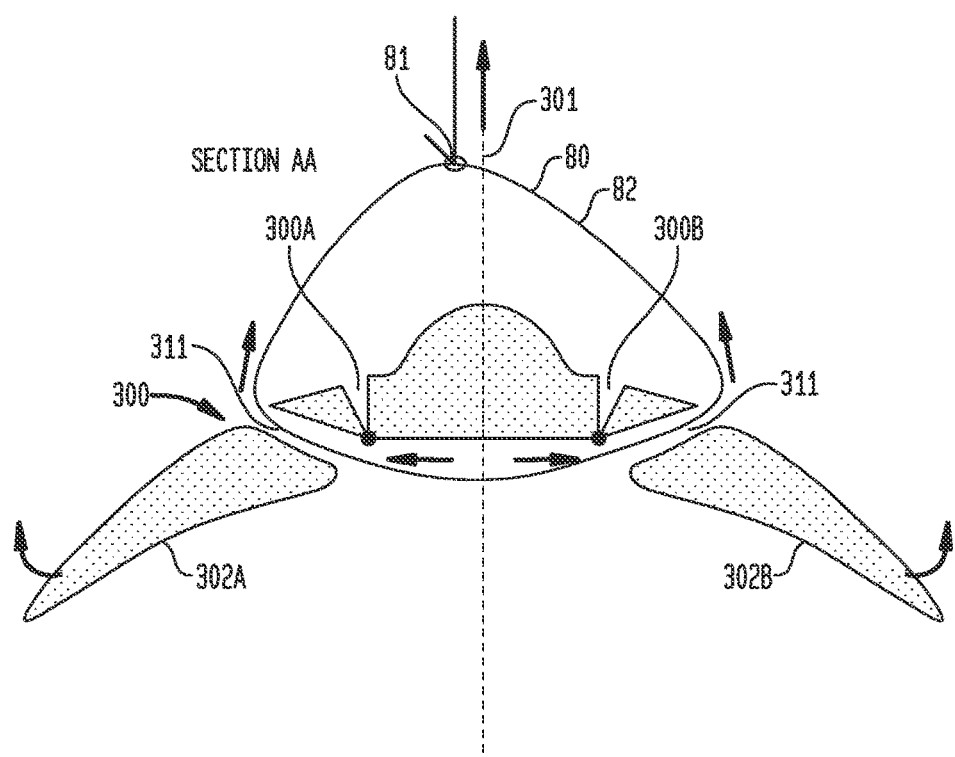

FIGS. 26A and 26B depict another embodiment, where the filament is utilized to apply the above-mentioned force to the wings to expand the wings. In this regard, FIG. 26B is a cross-sectional view of section AA of the toggle 300 depicted in FIG. 26A. In this embodiment, the holes 311 of the toggle 300 for the filament 80 are angled relative to the lateral axis 301 or positioned so as to aid in the support of the widened portion, or 'wings'. In an exemplary embodiment, this can aid in opening the toggle 300, which has hinge sections 300A and 300B extending along the midline. In an exemplary embodiment, loop 82 extends through holes 311 as may be seen. The angle of the holes relative to axis 301 has utility in that as the loop 82 is closed due to the tensioning of filament 80, the filament 80 applies a force onto wings 302A and 302B, lifting the wings upward and against the artery. It is noted that such utility can also be achieved without the angling of the holes 311 relative to axis 301. In this regard, because the holes 311 are outboard of the hinge sections 300A and 300B, the force resulting from the tensioning of the filament 80 is applied to the wings, thus forcing the wings upward and against the artery.

In addition to radiopaque marking schemes mentioned above, some embodiments detailed herein and/or variations thereof may include additional markers to ensure or otherwise substantially and/or effectively statistically improve the chances of utilitarianly deploying the toggles. Radiopaque markings on the tubes can aid in enabling the user to estimate the amount of delivery tube and/or release tube that has been pushed into the vessel. This can help the user avoid unutilitarian advancement of the toggle into the vessel (e.g., too much advancement), thereby obviating any adverse situations during deployment such as catching of the toggle on the inner wall downstream. The delivery tube and/or the release tube may have radiopaque strips or rings at fixed distances. It may also have rings with increasing thicknesses. The gradient may be designed in proportion to a qualitative assessment of distance advanced. The tube(s) may also have dots in place of rings to differentiate between the radiopaque sheath tip and the delivery tube.

Figure 27D:
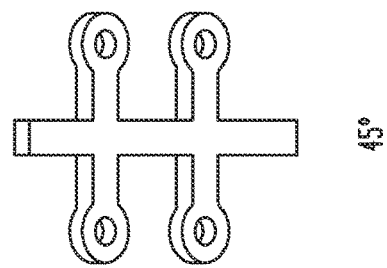
FIG. 27A-D depict an exemplary embodiment of a marker.
Figure 27C:
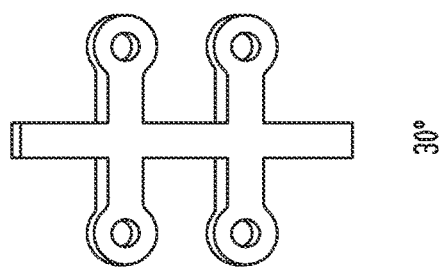
Figure 27B:
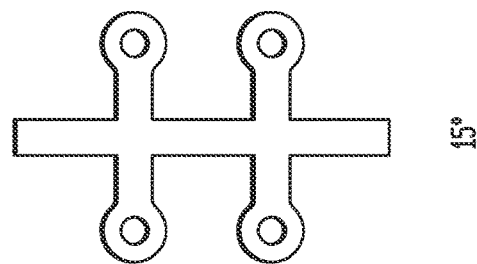
Figure 27A:
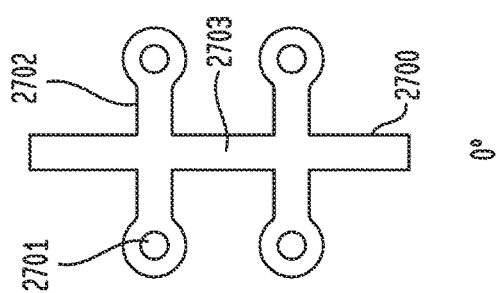

In a similar vein, an exemplary embodiment includes a toggle or other degradable intraluminal sealing member that includes a radiopaque marker. In an exemplary embodiment, one or more or all of the embodiments of toggles detailed herein and/or variations thereof may include therein a relatively thin stainless steel radiopaque marker (thickness of 0.005"-0.010"). In some exemplary embodiments, the marker may have hollow features. FIGS. 27A-D depict such an exemplary embodiment of a marker 2700, having hollow holes 2701 in arms 2702 extending from a core 2703. Embedded in or otherwise attached to a toggle, the hollow features can be utilized to indicate toggle orientation during deployment. By way of example, depending on the orientation of the toggle relative to a viewing perspective, the holes will appear anywhere from circular to highly elliptical. More particularly, under fluoroscopic guidance, the holes appear circular at 0° relative to the viewing perspective (FIG. 27A), elliptical at 15° relative to the viewing perspective (FIG. 27B), more elliptical at 30° relative to the viewing perspective (FIG. 27C) and highly-elliptical and/or closed off completely (i.e., one cannot see through the hole as the wall of the hole blocks the view) at 45° (FIG. 27D). Accordingly, there is a method of fluoroscopically confirming the orientation of the toggle relative to a viewing perspective based on how the holes look relative to a viewing perspective prior to initiating any of the actions detailed herein and/or variations thereof associated with deployment of the toggle.

More particularly, in an exemplary embodiment, during deployment of the toggle, the holes may appear closed (or highly elliptical) as the toggle is released from the delivery instrument and hangs in the intraluminal space. As the toggle is brought closer to the vessel wall as detailed herein, the varying degrees of circularity of the holes relative to a viewing perspective via fluoroscopy can provide the user with a visual confirmation of accurate positioning and/or utilitarian positioning of the toggle.

In an exemplary embodiment, the marker can also be used as a reinforcing element that reinforces the toggle and improves resistance to the tensioning of the filament as detailed above. This can have utilitarian value in that it can substantially and/or effectively statistically increase the likelihood that the toggle stays in contact with the inner wall of the vessel throughout the period of resorption. This as compared to that which would be the case in a similarly situated toggle without the marker. In an exemplary embodiment, the "marker" need never be used as a marker, but instead simply only as a reinforcing device.

Figure 29:
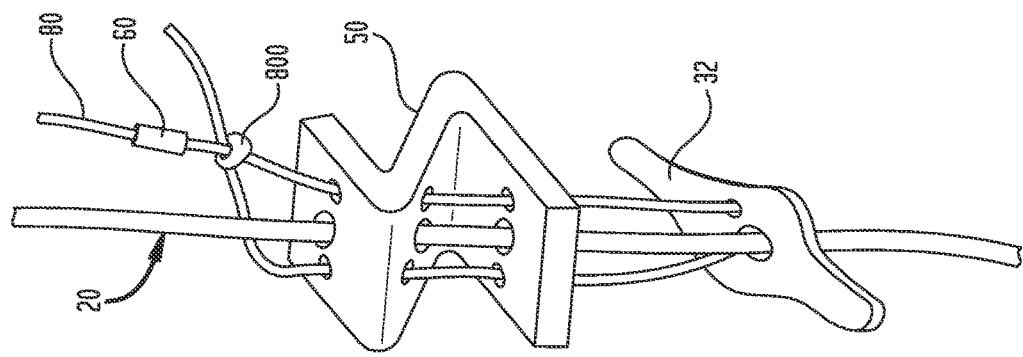
FIGS. 28-30 depict exemplary embodiments of guide wire-plug association.
Figure 28:
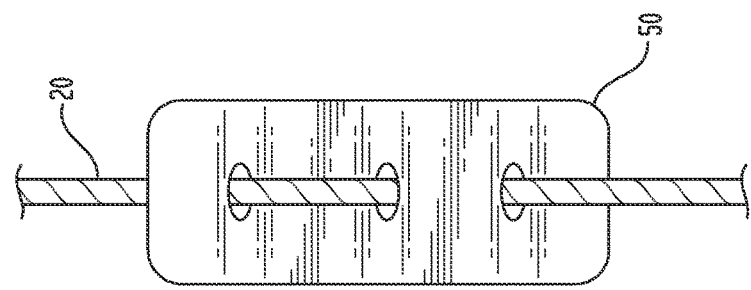
Figure 30:
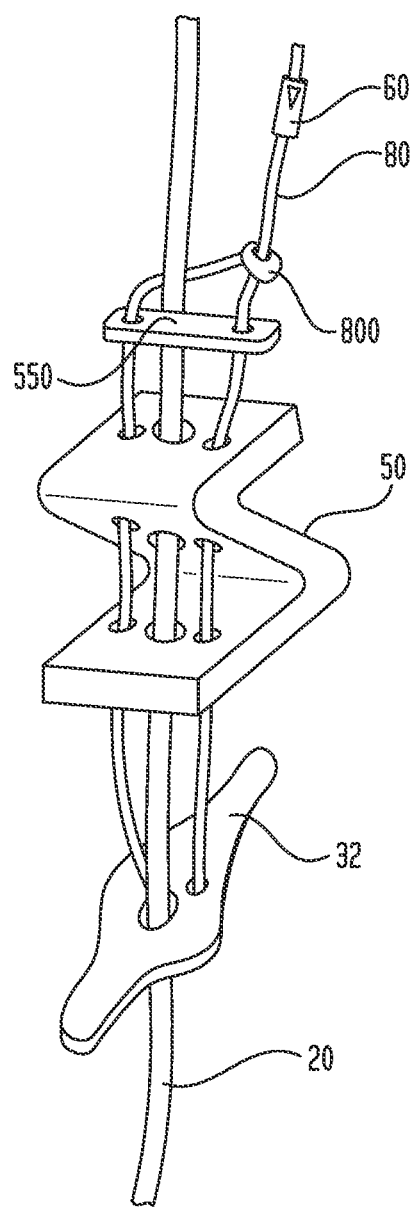

As noted above, an exemplary embodiment includes a guide wire 20 that passes through holes in the plug 50. FIGS. 28, 29 and 30 depict exemplary embodiments, of such a configuration. In a further embodiment, there is an extra luminal sealing component 550, as depicted in FIG. 30, that is in the form of a stainless steel plate or bar about 0.5" long or less and about 0.010" thick or less placed between the hemostatic pad 50 and the lock 60. The plate 550 can have utilitarian value in that it can increase or otherwise result in utilitarian distribution of compression forces on the plug 50 more evenly in order to achieve statistically and/or effective reliable hemostasis.

Embodiments disclosed herein and variations thereof include various interventional cardiology procedures which utilize large access sheaths to accommodate large devices. Non-exhaustive examples may include methods that include steps of balloon aortic valvuloplasty (BAV) and percutaneous aortic valve replacement (PAVR), both of which are utilized with sheaths ranging from 12-24F. Closure of access sites involving sheaths this large are accomplished with the closure devices and deployment instruments disclosed herein and variations thereof, as well as methods for closing such access sites disclosed herein (which includes those disclosed in the above referenced applications, scaled for such closure) instead of and/or in addition to surgical closure procedures and/or the use of multiple traditional vascular closure devices. In an exemplary embodiment, the devices and methods disclosed herein and variations thereof reduce by 50%, 75%, 90%, 95%, and/or 99% or more the failure rates associated with closure of access sites of the just-mentioned procedures (i) such as those disclosed by, for example, Herrmann et al, discusses the successful use of multiple 8F Angio-Seal devices (St Jude Medical, Minnetonka, Minn.) to close the arterial access site from BAV procedures, combating historical vascular complication rates from various studies ranging from 11-23%, (ii) and/or such as those disclosed by the Ramy et a12 report on the use three Perclose devices utilized for the closure of PAVR arterial access sites, suggesting deployment of the devices at 60 degree offsets to completely close the arteriotomy around the periphery.

It is noted that some embodiments include methods of utilizing the devices and/or systems and/or components detailed herein and/or variations thereof. Such methods can include individual method actions associated with/corresponding to the movement, positioning, use, etc., of the devices and systems and components detailed herein and/or variations thereof.

In an exemplary embodiment, there is a closure device for sealing a percutaneous puncture in a wall of a body passageway, the closure device comprising:
  at least one of an:
    anchor configured to engage an interior surface of the body passageway, and
    a plug configured to engage an exterior surface of the body passageway; and
  a guide wire configured to extend from an outside of the body to inside the body passageway,
  wherein the at least one of the anchor and the plug is associated with the guide wire.

In an exemplary embodiment, there is a closure device as described above and/or below, wherein the anchor is associated with the guide wire such that the anchor is slidingly coupled to the guide wire.

In an exemplary embodiment, there is a closure device as described above and/or below, wherein the anchor includes a cavity, and the guide wire extends through the cavity.

In an exemplary embodiment, there is a closure device as described above and/or below, wherein the cavity is an orifice through the anchor.

In an exemplary embodiment, there is a closure device as described above and/or below, wherein the cavity is a notch on a periphery of the anchor.

In an exemplary embodiment, there is a closure device as described above and/or below, wherein the plug is associated with the guide wire such that the plug is slidingly coupled to the guide wire.

In an exemplary embodiment, there is a deployment instrument for deploying a closure device for sealing a percutaneous puncture in a wall of a body passageway, the deployment instrument comprising:
  the closure device;
  a carrier device, wherein the carrier device is configured to hold the closure device in a pre-deployment state; and
  a guide wire, the guide wire passing through at least a portion of the closure device.

In an exemplary embodiment, there is a deployment instrument as described above and/or below, wherein the closure device includes a toggle, wherein the guide wire passes through the toggle.

In an exemplary embodiment, there is a deployment instrument as described above and/or below, wherein the closure device includes a plug, wherein the guide wire passes through the plug.

In an exemplary embodiment, there is a deployment instrument as described above and/or below, further comprising:
  a tamper, wherein the guide wire is associated with the tamper.

In an exemplary embodiment, there is a deployment instrument as described above and/or below, wherein the tamper includes a plurality of lumens, wherein the guide wire extends through one of the lumens.

In an exemplary embodiment, there is a deployment instrument for deploying a closure device for sealing a percutaneous puncture in a wall of an artery, the deployment instrument comprising:
  the closure device, wherein the closure device includes a toggle and a plug connected to the toggle; and
  an actuatable assembly having an actuatable portion configured to extend into the artery such that the toggle is located in the artery while, in a first state, effectively maintaining a relative position of the toggle with respect to the actuatable portion.

In an exemplary embodiment, there is a deployment instrument as described above and/or below, wherein the actuatable assembly is configured to, upon actuation from the first state to a second state, permit the toggle to move relatively freely relative to the actuatable portion while connected to the plug and while the toggle is in the artery.

In an exemplary embodiment, there is a deployment instrument as described above and/or below, wherein the actuatable assembly is configured to extend into the artery such that at least a portion of the plug is located in the artery; and
  the actuatable assembly is configured to, upon actuation from the first state to a second state, permit the toggle to move relatively freely relative to the plug while connected to the plug and while the toggle and at least a portion of the plug is in the artery.

In an exemplary embodiment, there is a deployment instrument as described above and/or below, wherein the actuatable assembly includes a first lumened component in which the plug is located and a second lumened component in which the first lumened component is located; and
  wherein the instrument is configured to, upon actuation of the actuatable assembly, move the second lumened component relative to the first lumened component and/or visa-versa, thereby actuating from the first state to the second state and thereby permitting the toggle to move relatively freely relative to the actuatable portion while connected to the plug.

In an exemplary embodiment, there is a deployment instrument as described above and/or below, wherein at least a portion of the toggle is located within the lumen of the second lumened component; and
  wherein movement of the second lumened component relative to the first lumened component and/or visa-versa, upon actuation from the first state to the second state, results in the toggle being fully exposed outside the second lumen component.

In an exemplary embodiment, there is a deployment instrument as described above and/or below, further comprising:

a knob configured to turn relative to at least one of the first lumened component or the second lumened component to actuate the actuatable assembly.

In an exemplary embodiment, there is a deployment instrument for deploying a closure device for sealing a percutaneous puncture in a wall of a body passageway, the closure device including an anchor, a plug and a contiguous elongate filament configured to draw the plug towards the anchor upon the application of tension to the filament in a direction away from the anchor, the deployment instrument comprising:

a carrier assembly, wherein the carrier assembly is configured to hold the closure device in a pre-deployment state; and a tensioner assembly located inside the carrier assembly.

In an exemplary embodiment, there is a deployment instrument as described above and/or below, wherein the carrier assembly includes a first lumened component, wherein the first lumened component is configured to hold the closure device in a lumen thereof; and wherein the tensioner assembly is located in the lumen.

In an exemplary embodiment, there is a deployment instrument as described above and/or below, wherein the tensioner assembly includes a cartridge comprising a handle, a spring, and a suture interface that moves relative to the handle, movement relative to the handle causing at least one of compression or extension of the spring; and wherein the handle, the spring and the suture interface are located within the lumen.

In an exemplary embodiment, there is a deployment instrument as described above and/or below, wherein the tensioner assembly is configured to increase the tension in the filament upon linear movement of the tensioner assembly away from the wall of the body passageway when the closure device is anchored to the wall via the anchor such that the tension is gradually increased as the tensioner assembly is moved between a first linear distance and a second linear distance greater than the first linear distance from the wall of the body passageway.

In an exemplary embodiment, there is a deployment instrument as described above and/or below, wherein the deployment instrument is configured such that movement of the carrier assembly away from the wall of the body passageway when the closure device is anchored to the wall via the anchor with the cartridge in the carrier assembly while the filament is under tension withdraws the cartridge from the carrier assembly; and wherein the deployment instrument is configured such that the movement withdrawing the carrier assembly results in movement of the tensioner assembly from a first location that is a linear distance from the wall of the body passageway less than the first linear distance to a second location that is greater than the linear distance from the wall to the first location and less than or about equal to the first linear distance from the wall of the body passageway.

In an exemplary embodiment, there is a deployment instrument as described above and/or below, wherein the deployment instrument is configured such that movement of the carrier assembly away from the wall of the body passageway when the closure device is anchored to the wall via the anchor between a first linear distance from the wall to a second linear distance from the wall greater than the first linear distance while the filament is under tension results in withdrawal of the cartridge out of the first lumen; and wherein the tensioner assembly is configured to increase the tension in the filament upon linear movement of the handle away from the wall of the body passageway when the closure device is anchored to the wall via the anchor such that the tension is gradually increased as the tensioner assembly is moved between a third linear distance and a fourth linear distance greater than the third linear distance from the wall of the body passageway, wherein the third linear distance is greater than or about equal to the second linear distance.

A closure device for sealing a percutaneous puncture in a wall of a body passageway, the closure device comprising:

a toggle configured to engage an interior surface of the body passageway; and a filament threaded through three or more orifices in the toggle.

In an exemplary embodiment, there is a closure device as described above and/or below, wherein the filament is threaded through four orifices in the toggle.

In an exemplary embodiment, there is a deployment instrument as described above and/or below, wherein in the following order:

the filament enters a first orifice at a first side of the toggle and exits the first orifice at a second side opposite the first side of the toggle;

the filament enters a second orifice at a second side of the toggle and exits the second orifice at the first side of the toggle;

the filament enters a third orifice at the first side of the toggle and exits the third orifice at the second side opposite the first side of the toggle; and the filament enters a fourth orifice at the second side of the toggle and exits the fourth orifice at the first side of the toggle.

In an exemplary embodiment, there is a deployment instrument as described above and/or below, wherein the four orifices are generally linearly arranged across the toggle in an order of the first orifice, the second orifice, the third orifice and the fourth orifice.

In an exemplary embodiment, there is a closure device for sealing a percutaneous puncture in a wall of a body passageway, the closure device comprising:

a toggle configured to engage an interior surface of the body passageway;

a looped filament extending through the toggle; and a washer spanning across the loop and associated with the filament at two locations such that the filament of the look cannot constrict on itself proximate the washer.

In an exemplary embodiment, there is a closure device as described above and/or below, further comprising:

a first plug, wherein the filament is threaded through the first plug between the washer and the toggle on a first side of the loop; and a second plug, wherein the filament is threaded through the second plug between the washer and the toggle on a second side of the loop opposite the first side.

In an exemplary embodiment, there is a closure device for sealing a percutaneous puncture in a wall of a body passageway, the closure device comprising:

a toggle configured to engage an interior surface of the body passageway;

a looped filament extending through the toggle;

a first plug, wherein the filament is threaded through the first plug on a first side of the loop; and a second plug, wherein the filament is threaded through the second plug on a second side of the loop opposite the first side.

In an exemplary embodiment, there is a deployment instrument for deploying a closure device for sealing a percutaneous puncture in a wall of a body passageway, the closure device including an anchor, a plug and a contiguous elongate filament configured to draw the plug towards the anchor upon the application of tension to the filament in a direction away from the anchor, the deployment instrument comprising:

a closure device including an anchor and a pad connected to the anchor via a looped filament;

a first tamper lumen, the filament extending through the first tamper lumen on a first side of the loop; and a second tamper lumen, the filament extending through the second tamper lumen on a second side of the loop.

In an exemplary embodiment, there is a deployment instrument as described above and/or below, further comprising:

a first tamper, the first tamper including the first tamper lumen; and a second tamper, the second tamper including the second tamper lumen.

In an exemplary embodiment, there is a deployment instrument as described above and/or below, further comprising:

a tamper, wherein the first and second tamper lumens extend through the tamper.

In an exemplary embodiment, there is a deployment instrument for deploying a closure device for sealing a percutaneous puncture in a wall of a body passageway, the closure device including an anchor, a plug and a contiguous elongate filament configured to draw the plug towards the anchor upon the application of tension to the filament in a direction away from the anchor, the deployment instrument comprising:

a closure device, the closure device including a toggle and a plug connected to the toggle via a looped filament; and a tensioner assembly, the tensioner assembly spanning the loop and being spring biased to resist closure of the loop.

In an exemplary embodiment, there is a deployment instrument as described above and/or below wherein the tensioner assembly includes a first and second arm, the arms being spring biased away from one another, the arms being respectively connected to sides of the loop, such that closure of the loop imparts a force onto the arms that drives the arms towards one another.

In an exemplary embodiment, there is a method of closing a puncture in an artery wall, comprising:

inserting an anchor through the puncture into the artery;

moving an expandable device along the longitudinal direction of the artery to a location longitudinally proximate the puncture and longitudinally proximate the anchor; and expanding the expandable device, thereby applying a compressive force to the anchor.

In an exemplary embodiment, there is a method as described above and/or below, wherein the compressive force compresses the anchor against the artery wall.

In an exemplary embodiment, there is a method as described above and/or below, wherein the expandable device is an occlusion balloon.

In an exemplary embodiment, there is a method as described above and/or below, further comprising:

moving a second occlusion balloon along the longitudinal direction of the artery; and occluding the artery.

In an exemplary embodiment, there is a method as described above and/or below, further comprising:

while the expandable device is applying the compressive force, moving a plug against the artery wall proximate the anchor.

In an exemplary embodiment, there is a closure device for sealing a percutaneous puncture in a wall of a body passageway, the closure device comprising:

an anchor configured to engage an interior surface of the body passageway, wherein the anchor includes a first portion and a second portion, the first portion extending away from the second portion, and wherein at least one of the first portion and the second portion is hinged.

In an exemplary embodiment, there is a closure device as described above and/or below, wherein the anchor includes a main body between the first portion and the second portion, wherein the hinge is between the first portion and the main body.

In an exemplary embodiment, there is a closure device as described above and/or below, wherein the anchor includes a main body between the first portion and the second portion; the first portion and the second portion are hinged; the hinge of the first portion is between the first portion and the main body; and wherein the hinge of the second portion is between the second portion and the main body.

In an exemplary embodiment, there is a closure device as described above and/or below, wherein the hinge comprises a notch in the anchor.

In an exemplary embodiment, there is a closure device as described above and/or below, wherein the anchor includes a plurality of orifices through which a filament is looped, one side of the loop extending through one orifice and the other side of the loop extending through the other orifice; and wherein the hinge is between the orifices.

In an exemplary embodiment, there is a closure device for sealing a percutaneous puncture in a wall of a body passageway, the closure device comprising:

an anchor configured to engage an interior surface of the body passageway, wherein the anchor includes a fluoroscopic marker, the marker including a hole having a circular cross-sectional area extending therethrough.

In an exemplary embodiment, there is a closure device as described above and/or below, wherein the marker includes a plurality of holes having respective circular cross-sectional areas extending therethrough.

In an exemplary embodiment, there is a closure device as described above and/or below, wherein the marker includes arms extending from one another, the respective arms having respective holes.

In an exemplary embodiment, there is a method of sealing a percutaneous puncture in a body passageway of a living being, the method comprising:

inserting an anchor into the body passageway;

inserting at least a portion of a plug coupled to the anchor into the body passageway; and closing the puncture by moving the plug towards the anchor.

In an exemplary embodiment, there is a method as described above and/or below, further comprising:

inserting in its entirety the plug into the body passageway.

In an exemplary embodiment, there is a method as described above and/or below, wherein:

the anchor is held effectively rigidly relative to the plug while inserting at least a portion of the plug into the body passageway.

In an exemplary embodiment, there is a method as described above and/or below, wherein:

at least a portion of the anchor is enclosed within a delivery apparatus while inserting at least a portion of the plug into the body passageway.

In an exemplary embodiment, there is a method as described above and/or below, wherein:

the delivery apparatus is a delivery tube.

In an exemplary embodiment, there is a method as described above and/or below, further comprising:

releasing the anchor after it is held effectively rigidly relative to the plug such that the anchor is effectively movably connected to the plug while at least a portion of the plug is in the body passageway.

In an exemplary embodiment, there is a method as described above and/or below, wherein:

the action of inserting the anchor into the body passageway is executed while the anchor is associated with a guidewire extending into the body passageway through the puncture from outside the body passageway.

In an exemplary embodiment, there is a method as described above and/or below, further comprising:

passing the anchor completely through an insertion sheath while at least a portion of the anchor is enclosed within the delivery apparatus.

In an exemplary embodiment, there is a method of sealing a percutaneous puncture in a body passageway of a living being, the method comprising:

inserting a guidewire into the body passageway such that the guidewire extends from outside the body passageway, through the puncture and into the body passageway; and inserting an anchor into the body passageway while the anchor is associated with the guidewire extending from outside the body passageway, through the puncture and into the body passageway.

In an exemplary embodiment, there is a method as described above and/or below, wherein:

the guidewire extends through the anchor, and the anchor slides along the guidewire while inserting the anchor into the body passageway.

In an exemplary embodiment, there is a method as described above and/or below, wherein:

the guidewire extends through a plug that is coupled to the anchor, and the plug slides along the guidewire while inserting the anchor into the body passageway.

In an exemplary embodiment, there is a method as described above and/or below, further comprising:

associating the guidewire with the anchor prior to inserting the anchor into the body passageway.

In an exemplary embodiment, there is a method as described above and/or below, wherein:

the action of associating the guidewire is executed while the puncture is open.

In an exemplary embodiment, there is a method as described above and/or below, wherein:

the action of associating the guidewire is executed in relatively close temporal proximity to at least one of forming the puncture and closing the puncture.

In an exemplary embodiment, there is a method as described above and/or below, further comprising:

obtaining access to a deployment instrument including a closure device including the anchor and the guidewire while the anchor is associated with the guidewire.

In an exemplary embodiment, there is a method as described above and/or below, wherein:

the action of obtaining access includes opening a package containing the deployment instrument including the closure device including the anchor and the guidewire while the anchor is associated with the guidewire.

In an exemplary embodiment, there is a method as described above and/or below, wherein:

the package is at least one of a hermetically sealed.

In an exemplary embodiment, there is method of sealing a percutaneous puncture in a body passageway of a living being, the method comprising:

inserting a distal end section of a deployment instrument into the puncture from outside of the passageway, wherein the distal end section of the deployment instrument rigidly supports an anchor, the distal end section including a first component and a second component being in actuatable relationship to one another.

In an exemplary embodiment, there is a method as described above and/or below, further comprising:

actuating the deployment instrument to move the first component relative to the second component and/or visa-versa, wherein the actuation relieves the rigid support of the anchor, thereby enabling the anchor to effectively move relative to the distal end section.

In an exemplary embodiment, there is a method as described above and/or below, further comprising:

inserting the distal end section into an insertion sheath extending through the puncture from outside of the passageway to inside of the passageway while the distal end section of the deployment instrument rigidly supports the anchor.

In an exemplary embodiment, there is a method as described above and/or below, further comprising:

inserting the insertion sheath into the puncture.

In an exemplary embodiment, there is a method as described above and/or below, wherein:

the insertion sheath is inserted into the puncture such that the insertion sheath substantially deforms from a linear configuration.

In an exemplary embodiment, there is a method as described above and/or below, further comprising:

after inserting the insertion sheath into the puncture such that the insertion sheath substantially deforms from the linear configuration, moving the insertion sheath relative to the deployment instrument and/or visa-versa so that the anchor is exposed from the insertion sheath and in the passageway.

In an exemplary embodiment, there is a method as described above and/or below, further comprising:

actuating the deployment instrument to move the first component relative to the second component and/or visa-versa, wherein the actuation relieves the rigid support of the anchor, thereby enabling the anchor to effectively move relative to the distal end section.

In an exemplary embodiment, there is a method as described above and/or below, further comprising:

after actuating the deployment instrument, moving the deployment instrument in a distal direction so that the anchor abuts a wall of the passageway proximate the puncture.

In an exemplary embodiment, there is a method as described above and/or below, further comprising:

after actuating the deployment instrument, moving the deployment instrument in a distal direction so that the anchor abuts a wall of the passageway proximate the puncture and so that a plug contained in the deployment instrument moves towards the anchor and towards the puncture.

In an exemplary embodiment, there is method of sealing a percutaneous puncture in a wall of a body passageway, comprising:

providing a deployment instrument carrying a tensioner assembly and a closure device within the deployment instrument, the closure device including an anchor, a plug and a contiguous elongate filament configured to draw the plug towards the anchor upon the application of tension to the filament in a direction away from the anchor;

positioning a distal end of the deployment instrument through the puncture into the body passageway such that the anchor is positioned in the body passageway;

pulling the deployment instrument away from the puncture while the filament is connected to the tensioner assembly such that a mechanically induced tension force is applied to the filament causing the tensioner assembly to be withdrawn from an interior of the deployment instrument; and pulling the tensioner assembly away from the puncture while the filament is connected to the tensioner assembly such that the mechanically induced tension force is applied to the filament such that the tension force increases with increasing distance of the tensioner assembly away from the puncture to draw the anchor and the seal towards each other and into engagement with the wall of the body passageway at respectively opposite sides of the wall.

In an exemplary embodiment, there is a method as described above and/or below, wherein pulling the tensioner assembly away from the puncture while the filament is connected to the tensioner assembly results in the application of a linearly increasing mechanically induced tension force to the filament.

In an exemplary embodiment, there is a method as described above and/or below, wherein the mechanically induced increasing tension force is produced via compression of a spring.

In an exemplary embodiment, there is a method as described above and/or below, wherein the tensioner assembly includes a handle that is movable relative to a first location on the tensioner assembly to which the filament is connected, the method further comprising continuing to pull the tensioner assembly away from the puncture by pulling on the handle until the handle no longer moves relative to the first location on the tensioner assembly.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with any future claims and their equivalents.

What is claimed is:

1. A deployment instrument configured to be inserted along a guidewire to seal a percutaneous puncture in a wall of an artery, the deployment instrument comprising:
   a guidewire;
   an inserter sheath elongated along a longitudinal axis, the inserter sheath defining a proximal end, a distal end spaced from the proximal end in a distal direction that is aligned with longitudinal axis, and a inserter sheath lumen that extends from the proximal end of the inserter sheath to the distal end of the inserter sheath, the inserter sheath defining an inner diameter of the inserter sheath lumen that is at least 3.0 mm, wherein the inner diameter is perpendicular to the longitudinal axis; and
   an assembly that is insertable into the inserter sheath lumen of the inserter sheath in the distal direction, the assembly being elongate along the longitudinal axis, the assembly including:
   a) a closure device configured to slide along the guide wire as the assembly is inserted into the lumen, the closure device comprising a toggle having a first end and a second end opposite the first end;
   b) a suture coupled to the toggle and to the assembly such that the suture extends through the assembly along the longitudinal axis;
   c) a delivery component having a proximal end, a distal end spaced from the proximal end along the longitudinal axis, and a first lumen that extends from the distal end to the proximal end; and
   d) a release component that extends along the delivery component, the release component having a rear end, a front end spaced from the rear end along the longitudinal axis, and a second lumen that extends from the front end to the rear end, and the delivery component is disposed in the second lumen of the release component, wherein the distal end of the delivery component and the front end of release component hold the toggle in a pre-deployment state such that the first end of the toggle is fixed between the distal end of the delivery component and the front end of the release component, and
   e) a tamper in the delivery component, the tamper including a body that extends along the longitudinal axis, a first channel that extends through the body, and a second channel that extends through the body, wherein the suture extends through the first channel and the first channel is configured to receive the guidewire as the assembly is inserted into the inserter sheath;
   whereby the assembly is sized and configured to be seated in the inserter sheath lumen and coupled to the inserter sheath such that the second end of the toggle protrudes from the distal end of the inserter sheath in the pre-deployment state.

2. The deployment instrument of claim 1, wherein the toggle includes a cavity configured to receive therethrough the guidewire.

3. The deployment instrument of claim 1, wherein the closure device includes a plug having a first aperture that receives the suture therethrough, and at least a second aperture.

4. The deployment instrument of claim 1, wherein the release component is configured to hold at least a portion of the toggle up to and until the toggle is released into the artery.

5. The deployment instrument of claim 1, wherein the release component is configured to hold the toggle in its entirety.

6. The deployment instrument of claim 1, wherein the delivery component is inside the release component such that the toggle is held in the pre-deployment state between the release component and the delivery component, wherein movement of the release component relative to the delivery component releases the toggle from between the delivery component and the release component.

7. The deployment instrument of claim 1, wherein the release component and the delivery component have a cylindrical shape and are substantially symmetric around the same longitudinal axis.

8. The deployment instrument of claim 1, further comprising an actuator that is configured to translate the release component with respect to the delivery component in a proximal direction toward the proximal end of the inserter sheath to release the first end of the toggle from between the distal end of the delivery component and the front end of the release component.

9. The deployment instrument of claim 8, wherein the closure device includes a plug having a first aperture and at least a second aperture, wherein the suture extends through the first aperture.

10. The deployment instrument of claim 9, further comprising a locking member disposed along the suture in the proximal direction with respect to the plug, wherein the proximal direction is opposite the distal direction, wherein the tamper is configured to slide along the suture in the distal direction so as to urge the locking member toward the plug.

11. The deployment instrument of claim 1, wherein the closure device includes a plug connected to the toggle with the suture, wherein the plug is contained within the a distal end of the delivery component, wherein when the assembly is fully seated in the lumen the inserter sheath, an entirety of the toggle and the distal end of the delivery component that contains the plug protrudes out of the distal end of the inserter sheath the distal direction.

12. The deployment instrument of claim 1, further comprising an actuator configured to move at least one of the delivery component and the release component with respect to each the other in the inserter sheath to transition the toggle from the pre-deployment state into a deployed state where the release component does not hold the at least a portion of the toggle.

13. The deployment instrument of claim 1, wherein the inserter sheath defines a first length that extends from the proximal end to the distal end, and wherein the assembly defines a second length that extends from the rearward end to the forward end and that is greater than the first length.

14. The deployment instrument of claim 1, wherein when the assembly is seated in the lumen of the inserter sheath, the distal end of the delivery component and the front end of the release component protrude from the distal end of the inserter sheath in the pre-deployment state.

15. The deployment instrument of claim 1, wherein the toggle has a length between 10 mm and 27 mm and a width that perpendicular to the length that is between 3 mm and 10 mm.

16. A deployment instrument configured to seal a percutaneous puncture in a wall of an artery, the deployment instrument comprising:
an inserter sheath defining a proximal end, a distal end spaced from the proximal end of in a distal direction, a lumen that extends from the proximal end to the distal end, and a first length that extends from the proximal end to the distal end, wherein the distal end is configured to be inserted through the puncture;
a closure device that includes a toggle and a plug connected to the toggle; and
an actuatable assembly that is elongate along a longitudinal direction, the actuatable assembly including a rearward end and a forward end spaced from the rearward end along the longitudinal direction, and a second length that extends from the rearward end to the forward end, the actuatable assembly further including
a) a first lumened component including a first lumen that contains the plug, and
b) a second lumened component that includes a second lumen with the second lumen including the first lumened component and at least a portion of the toggle, and at least one of the first lumened component and the second lumened component is movable with respect to each other;
c) an actuator configured to transition the actuatable assembly from a first state, where the toggle is fixed between the first lumened component and the second lumened component at the forward end of the actuatable assembly, into a second state, where the toggle is moveable with respect to the actuatable assembly,
wherein the second length of the actuatable assembly is greater than the first length of the inserter sheath when the actuatable assembly is fully seated in the inserter sheath, and wherein the forward end extends out of the distal end of the inserter sheath such that the toggle is located completely outside of the inserter sheath while in the first state.

17. The instrument of claim 16, wherein the actuatable assembly is configured to, upon actuation from the first state to a second state, permit the toggle to move while connected to the plug and while the toggle disposed at a location out of the distal end of the inserter sheath is in the artery.

18. The instrument of claim 16, wherein the forward end of the actuatable assembly is configured to extend into the artery such that at least a portion of the plug is located in the artery; and the actuatable assembly is configured to, upon actuation from the first state to the second state, permit the toggle to move relative to the plug while connected to the plug and while the toggle and at least a portion of the plug is in the artery.

19. The instrument of claim 16, wherein movement of the second lumened component relative to the first lumened component and/or visa-versa, upon actuation from the first state to the second state, ejects an entirety of the toggle from the second lumen component.

20. The instrument of claim 19, further comprising an actuator that is a knob configured to turn relative to at least one of the first lumened component or the second lumened component to actuate the actuatable assembly.

21. The instrument of claim 16, wherein the first lumened component is a delivery tube and the second lumened component is a release tube.

22. The deployment instrument of claim 16, wherein the closure device includes a suture coupled to the toggle and to the plug, wherein the plug defines at least a first aperture and at least a second aperture, wherein the suture extends through the first aperture, and the second aperture is sized to receive the guidewire therethrough as the actuatable assembly is inserted into the lumen of the inserter sheath.

23. The deployment instrument of claim 22, further comprising a tamper that is slidable along the suture, the tamper including a first lumen and a second lumen, wherein the suture extends through the first lumen so that the tamper is slidable along the suture, and the second lumen is configured to receive the guidewire as the assembly is inserted into the lumen of the inserter sheath.

24. The deployment instrument of claim 23, further comprising a locking member disposed along the suture in a proximal direction with respect to the plug, wherein the proximal is opposite the distal direction, wherein the tamper configured to slide along the suture and the received guidewire in the distal direction so as to urge the locking member toward the plug.

25. The deployment instrument of claim 24, wherein the actuator that is a lever coupled to the second lumened component, wherein rotation of the lever translates the second lumened component with respect to the first lumened component in a proximal direction toward the proximal end of the inserter sheath to release the toggle.

26. The deployment instrument of claim 16, wherein a distal end of the first lumened component and a front end of the second lumened component define the forward end of actuatable assembly.

27. The deployment instrument of claim 16, wherein the toggle has a length between 10 mm and 27 mm and a width that perpendicular to the length that is between 3 mm and 10 mm.

* * * * *